US007824680B2

(12) United States Patent
Varner

(10) Patent No.: US 7,824,680 B2
(45) Date of Patent: Nov. 2, 2010

(54) METHODS FOR INHIBITING ANGIOGENESIS

(75) Inventor: Judith A. Varner, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 914 days.

(21) Appl. No.: 10/485,758

(22) PCT Filed: Aug. 1, 2002

(86) PCT No.: PCT/US02/24573

§ 371 (c)(1),
(2), (4) Date: Oct. 18, 2004

(87) PCT Pub. No.: WO03/019136

PCT Pub. Date: Mar. 6, 2003

(65) Prior Publication Data

US 2005/0129681 A1    Jun. 16, 2005

Related U.S. Application Data

(60) Provisional application No. 60/310,645, filed on Aug. 6, 2001.

(51) Int. Cl.
*A61K 39/395* (2006.01)
*A61K 38/10* (2006.01)
(52) U.S. Cl. .............. 424/143.1; 424/130.1; 424/141.1; 424/152.1; 424/156.1; 424/172.1; 514/2
(58) Field of Classification Search .............. 424/130.1, 424/143.1, 145.1, 141.1, 152.1, 156.1, 172.1; 514/2
See application file for complete search history.

(56) References Cited

U.S. PATENT DOCUMENTS

| | | | | |
|---|---|---|---|---|
| 4,894,326 A * | 1/1990 | Matsuura et al. | ............ | 435/7.21 |
| 5,192,746 A | 3/1993 | Lobl et al. | .................... | 514/11 |
| 5,523,229 A * | 6/1996 | Feinberg et al. | ............. | 435/337 |
| 5,688,913 A | 11/1997 | Arrhenius et al. | ........... | 530/330 |
| 5,730,978 A * | 3/1998 | Wayner | .................... | 424/144.1 |
| 5,780,426 A | 7/1998 | Palladino et al. | ................ | 514/9 |
| 5,869,448 A | 2/1999 | Arrhenius et al. | ............. | 514/11 |
| 5,980,887 A | 11/1999 | Isner et al. | .................. | 424/93.7 |
| 5,981,478 A | 11/1999 | Ruoslahti et al. | ............... | 514/10 |
| 6,034,056 A | 3/2000 | Dutta | ............................ | 514/9 |
| 6,034,057 A | 3/2000 | Dutta | ............................ | 514/9 |
| 6,252,043 B1 | 6/2001 | Hession et al. | .............. | 530/350 |
| 6,306,840 B1 | 10/2001 | Adams et al. | ................ | 514/109 |
| 6,376,538 B1 | 4/2002 | Adams et al. | ................ | 514/466 |
| 6,713,604 B1 | 3/2004 | Kogan et al. | .................. | 530/317 |
| 6,818,617 B1 * | 11/2004 | Niewiarowski et al. | ........ | 514/12 |
| 2002/0172675 A1 | 11/2002 | Varner | ...................... | 424/131.1 |
| 2004/0220148 A1 | 11/2004 | Stilz et al. | ..................... | 514/80 |

FOREIGN PATENT DOCUMENTS

| WO | WO 96/01644 | 1/1996 |
|---|---|---|
| WO | WO 97/18838 | 5/1997 |
| WO | WO 00/15247 | 3/2000 |

OTHER PUBLICATIONS

Saiki, I., et al, Jpn. J. Cancer Res., 81: 668-675, 1990.*
Sanchez-Aparicio, P. et al., The Journal of Cell Biology, 126(1): 271-279, 1994.*
Koch, A.E., et al. Nature, 376: 517-519, 1995.*
Maurer, C.A. et al., Int. J. Cancer (Pred. Oncol.), 79: 76-81, 1998.*
Vanderslice, P. et al., Angiogenesis, 2: 265-275, 1998.*
Massia, S.P., et al, J. Biol. Chemistry, 267(20): 14019-14026, 1992.*
Sheppard, A.M., et al. Cell Adhesion and Communication, 2: 27-43, 1994.*
Detmar, M. et al. J. Invest. Dermatol. 111: 1-6, 1998).*
Saiki et al. (1990) "Inhibition of tumor angiogenesis by a synthetic cell-adhesive polypeptide containing the Arg-Gly-Asp (RGD) sequence of fibronectin, poly(RGD)," Jpn. J. Cancer Res. 81:668-675.
Sanchez-Aparicio et al. (1994) "Activation of the α4β1 integrin through the β1 subunit induces recognition of the RGDS sequence in fibronectin," J. Cell Biol. 126:271-279.
Yednock et al. (1995), "α4β1 integrin-dependent cell adhesion is regulated by a low affinity receptor pool that is conformationally responsive to ligand," J. Biol. Chem. 270:28740-28750.
Koch et al. (1995) "Angiogenesis mediated by soluble forms of E-selectin and vascular cell adhesion molecule-1," Nature 376:517-519.
Maurer et al. (1998) "Over-expression of ICAM-1, VCAM-1 and ELAM-1 might influence tumor progression in colorectal cancer," Int. J. Cancer (Pred. Oncol.) 79:76-81.
Clements JM et al. (1994) "Identification of a key integrin-binding sequence in VCAM-1 homologous to the LDV active site in fibronectin," J. Cell. Sci. 107:2127-2135.
Komoriya A et al. (1991) "The minimal essential sequence for a major cell type-specific adhesion site (CS1) within the alternatively spliced type III connecting segment domain of fibronectin is leucine-aspartic acid-valine (LDV)," J. Biol. Chem. 266:15075-15079.

(Continued)

*Primary Examiner*—Alana M. Harris
*Assistant Examiner*—Anne L Holleran
(74) *Attorney, Agent, or Firm*—Medlen & Carroll, LLP

(57) ABSTRACT

The invention provides methods for detecting and inhibiting angiogenesis, endothelial cell adhesion, and endothelial cell migration using agents which inhibit the specific binding of integrin α4β1 to one or more of its ligands. The invention further provides methods for screening test compounds for their ability to inhibit angiogenesis, endothelial cell adhesion, or endothelial cell migration by employing agents which inhibit the specific binding of integrin α4β1 to one or more of its ligands. The invention additionally relates to methods for isolating endothelial progenitor cells which express integrin α4β1. The methods of the invention are useful in, for example, diagnosing and inhibiting pathological conditions that are associated with angiogenesis, endothelial cell adhesion, and/or endothelial cell migration. The invention's methods are also useful in isolating endothelial progenitor cells, and in determining the mechanisms that underlie angiogenesis, development, wound healing, and the function of the female reproductive system.

12 Claims, 27 Drawing Sheets

OTHER PUBLICATIONS

Cardarelli PM et al. (1994) "Cyclic RGD peptide inhibits alpha 4 beta 1 interaction with connecting segment 1 and vascular cell adhesion molecule," J. Biol. Chem. 269:18668-18673.

Marcinkiewicz et al. (1999) "EC3, A novel heterodimeric disintegrin from *Echis carinatus* venom, inhibits α4 and α5 integrins in an RGD-independent manner," J. Biol. Chem. 274:12468-12473.

Marcinkiewicz et al. (2000) "Inhibitory effects of MLDG-containing heterodimeric disintegrins reveal distinct structural requirements for interaction of the integrin α9β1 with VCAM-1, tenascin-C, and osteopontin," J. Biol. Chem. 275:31930-31937.

Kim et al. (2000) "Regulation of Angiogenesis in vivo by ligation of integrin α5β1 with the central cell-binding domain of fibronectin," Amer. J. Path. 156:1345-1362.

Garmy-Susini et al. (2005) "Integrin alpha4beta1-VCAM-1-mediated adhesion between endothelial and mural cells is required for blood vessel maturation," J. Clin. Invest. 115(6):1542-1551.

Ausprunk et al., "Vascularization of normal and neoplastic tissues grafted to the chick chorioallantois. Role of host and preexisting graft blood vessels," Amer J Pathol, 79:597-628 (1975) abstract.

Bochner et al., "Adhesion of human basophils, eosinophils, and neutrophils to interleukin 1-activated human vascular endothelial cells: contributions of endothelial cell adhesion molecules," J Exp Med, 173:1553-1556 (1991).

Brando et al., "EC3, a heterodimeric disintegrin from *Echis carinatus*, inhibits human and murine alpha-4 integrin and attenuates lymphocyte infiltration of langerhans islets in pancreas and salivary glands in nonobese diabetic mice," Biochem Biophys Res Commun, 267:413-417 (2000).

Cardarelli et al., "Cyclic RGD peptide inhibits alpha-4/beta-1 interaction with connecting segment 1 and vascular cell adhesion molecule," J Biol Chem, 269:18668-18673 (1994).

Chisholm et al., "Monoclonal antibodies to the integrin alpha-4 subunit inhibit the murine contact hypersensitivity response," Eur J Immunol, 23:682-688 (1993) abstract.

Clements et al., "Identification of a key integrin-binding sequence in VCAM-1 homologous to the LDV active site in fibronectin," J Cell Sci, 107:2127-2135 (1994).

Curley et al., "Integrin antagonists," Cell Mol Life Sci, 56:427-441 (1999).

Dittel et al., "Regulation of human B-cell precursor adhesion to bone marrow stromal cells by cytokines that exert opposing effects on the expression of vascular cell adhesion molecule-I (VCAM-1)," Blood, 81:2272-2282 (1993).

Dudgeon et al., "Expression and characterization of a very-late antigen-4 (alpha-4/beta-1) integrin-binding fragment of vascular cell-adhesion molecule-1," Eur J Biochem, 226:517-523 (1994) abstract.

Garcia-Pardo et al., "Two novel monoclonal antibodies to fibronectin that recognize the Hep II and CS-1 regions respectively: their differential effect on lymphocyte adhesion," Biochem Biophys Res Commun, 186:135-42 (1992) abstract.

Grant et al., "Two different laminin domains mediate the differentiation of human endothelial cells into capillary-like structures in vitro," Cell, 58:933-943 (1989) abstract.

Hemler et al., "Characterization of five distinct cell surface heterodimers each with a common 130,000 molecular weight beta subunit," J Biol Chem, 262:3300-3309 (1987).

Hemler et al., "Characterization of the cell surface heterodimer VLA-4 and related peptides," J Biol Chem, 262:11478-11485 (1987).

Holzmann et al., "Identification of a murine Peyer's patch—specific lymphocyte homing receptor as an integrin molecule with an alpha chain homologous to human VLA-4 alpha," Cell, 56:37-46 (1989).

Humphries et al., A synthetic peptide from fibronectin inhibits experimental metastasis of murine melanoma cells, Science, 233:467-470 (1986).

Humphries et al., "Investigation of the biological effects of anti-cell adhesive synthetic peptides that inhibit experimental metastasis of B16-F10 murine melanoma cells," J Clin Invest, 81:782-790 (1988).

Isner and Asahara, "Angiogenesis and vasculogenesis as therapeutic strategies for postnatal neovascularization," J Clin Invest, 103:1231-1236 (1999).

Issekutz, "Inhibition of in vivo lymphocyte migration to inflammation and homing to lymphoid tissues by the TA-2 monoclonal antibody—a likely role for VLA-4 in vivo," J Immunol, 147:4178-4184 (1991).

Jackson et al., "Potent alpha-4/beta-1 peptide antagonists as potential anti-inflammatory agents," J Med Chem, 40:3359-3368 (1997).

Kim et al., "Regulation of angiogenesis in vivo by ligation of integrin alpha-5/beta-1 with the central cell-binding domain of fibronection," Am J Pathol, 156:1345-1362 (2000).

Kim et al., "Regulation of integrin alpha-5/beta-3-mediated endothelial cell migration and angiogenesis by integrin alpha-5/beta-1 and protein kinase A," J Biol Chem, 275:33920-33928 (2000).

Kinashi et al., "Adhesion molecules in hematopoietic cells," Blood Cells, 20:25-44 (1994) abstract.

Koivunen et al., "Isolation of a highly specific ligand for the alpha-5/beta-1 integrin from a phage display library," J Cell Biol, 124:373-380 (1994).

Lin et al., "Very late antigen 4 (VLA4) antagonists as anti-inflammatory agents," Curr Opin Chem Biol, 2:453-457 (1998) abstract.

Lin et al., "Selective, right-binding inhibitors of integrin alpha-4/beta-1 that inhibit allergic airway responses," J Med Chem, 42:920-934 (1999).

Marcinkiewicz et al., "EC3, a novel heterodimeric disintegrin from *Echis carinatus* venom, inhibits alpha-4 and alpha-5 integrins in an RGD-independent manner," J Biol Chem, 274:12468-12473 (1999).

Miyake et al., "Requirement for VLA-4 and VLA-5 integrins in lymphoma cells binding to and migration beneath stromal cells in culture," J Cell Biol, 119:653-662 (1992).

Mostafavi-Pour et al., "Identification of a novel heparin-binding site in the alternatively spliced IIICS region of fibronectin: roles of integrins and proteoglycans in cell adhesion to fibronectin splice variants," Matrix Biol, 20:63-73 (2001).

Munoz et al., "A novel region of the alpha-4 integrin subunit with a modulatory role in VLA-4-mediated cell adhesion to fibronectin," Biochem J, 327:727-733 (1997).

Needham et al., "Activation dependent and independent VLA-4 binding sites on vascular cell adhesion molecule-1," Cell Adhes Commun, 2:87-99 (1994) abstract.

Nowlin et al., "A novel cyclic pentapeptide inhibits alpha-4/beta-1 and alpha-5/beta-1 integrin-mediated cell adhesion," J Biol Chem, 268:20352-20359 (1993).

Ossowski and Reich, "Experimental model for quantitative study of metastasis," Cancer Res, 40:2300-2309 (1980).

Quackenbush et al., "Identification of several cell surface proteins of non-T, non-B acute lymphoblastic leukemia by using monoclonal antibodies," J Immunol, 134:1276-1285 (1985).

Rose et al., "Soluble VCAM-1 binding to alpha-4 integrins is cell-type specific and activation dependent and is disrupted during apoptosis in T cells," Blood, 95:602-609 (2000).

Sanchez-Madrid et al., "VLA-3: a novel polypeptide association within the VLA molecular complex: cell distribution and biochemical characterization," Eur J Immunol, 16:1343-1349 (1986) abstract.

Sheremata et al., "A safety and pharmacokinetic study of intravenous natalizumab in patients with MS," Neurology, 52:1072-1074 (1999).

Souers et al., "Novel inhibitors of alpha-4/beta-1 integrin receptor interactions through library synthesis and screening," Bioorg Med Chem Lett, 8:2297-2302 (1998).

Takahashi et al., "Ischemia- and cytokine-induced mobilization of bone marrow-derived endothelial progenitor cells for neovascularization," Nat Med, 5:434-438 (1999).

Tubridy et al., "The effect of anti-alpha4 integrin antibody on brain lesion activity in MS," Neurology, 53:466-72 (1999).

Varner et al., "Inhibition of angiogenesis and tumor growth by murine 7E3, the parent antibody of C7E3 fab (abciximab; ReoPro)," Angiogenesis, 3:53-60 (1999) abstract.

Yednock et al., "alpha-4/beta-1 integrin-dependent cell adhesion is regulated by a low affinity receptor pool that is conformationally responsive to ligand," J Biol Chem, 270:28740-28750 (1995).

Wayner et al., "Identification and characterization of the T lymphocyte adhesion receptor for an alternative cell attachment domain (CS-1) in plasma fibronectin," J Cell Biol, 109:1321-1330 (1989).

Wayner and Kovach, "Activation-dependent recognition by hematopoietic cells of the LDV sequence in the V region of fibronectin," J Cell Biol, 116:489-497 (1992).

Genbank Accession No. X02761, Apr. 18, 2005.

Genbank Accession No. X07979, Apr. 12, 1999.

Genbank Accession No. X53051, Mar. 31, 1995.

Genbank Accession No. XM_039012, Oct. 16, 2001.

Kumar et al., "Targeting integrins alpha-5/beta-3 and alpha-5/beta-5 for blocking tumor-induced angiogenesis" in Maragoudakis (ed.), *Advances in Experimental Medicine and Biology*, (Angiogenesis: From the Molecular to Integrative Pharmacology), Kluwer Academic / Plenum Publishers: New York, 476:169-180 (2000).

Fukushi et al., "The activity of soluble VCAM-1 in angiogenesis stimulated by IL-4 and IL-13," J Immunol, 165:2818-2823 (2000).

* cited by examiner

Figure 1
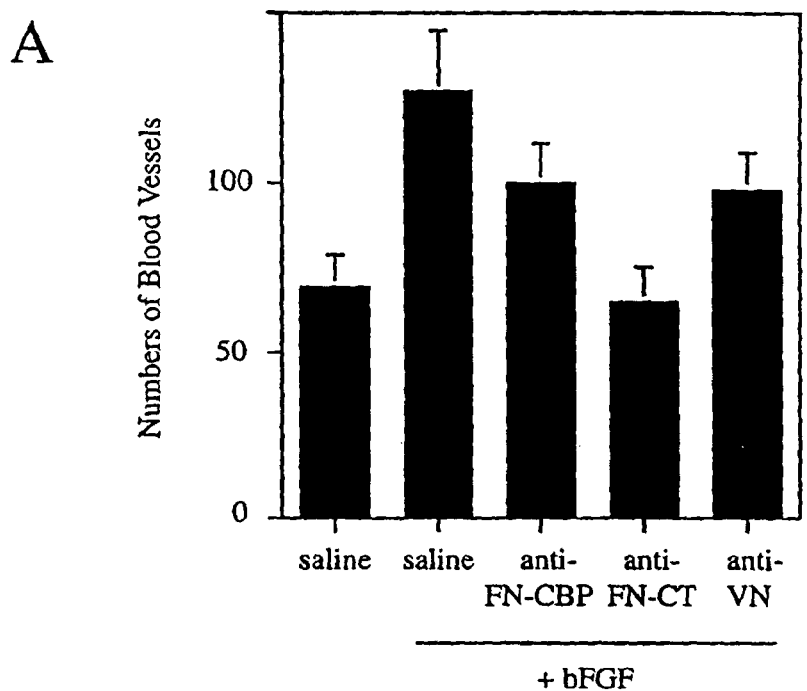
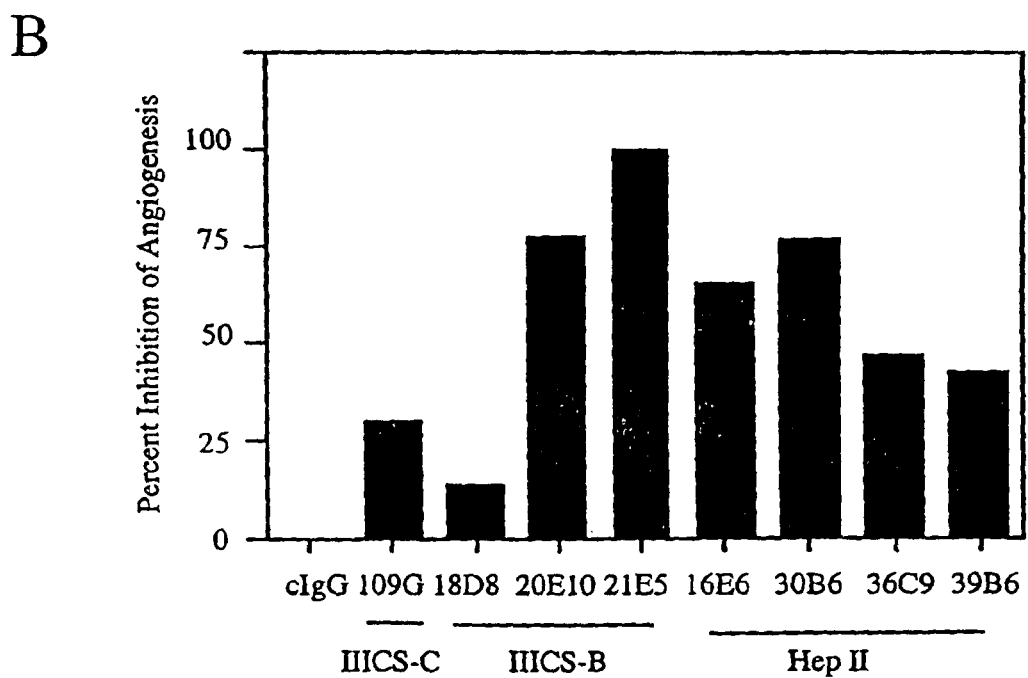

Figure 3
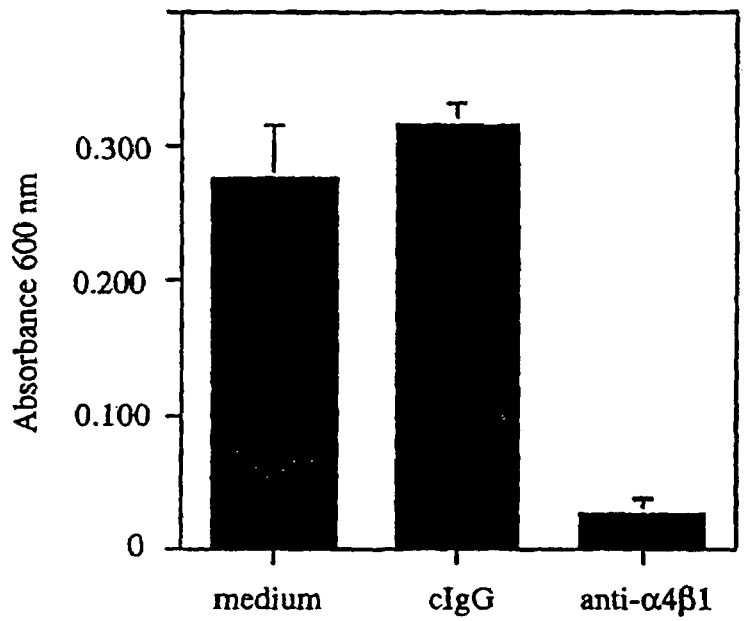
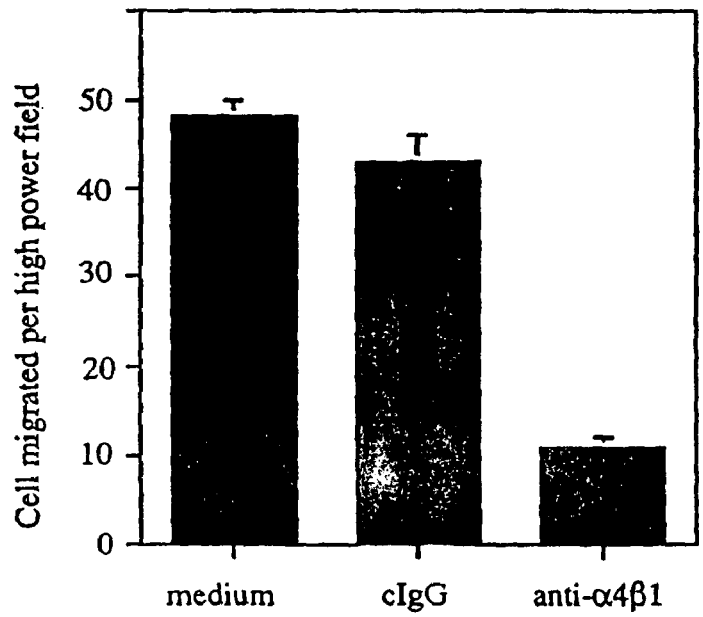

Figure 5
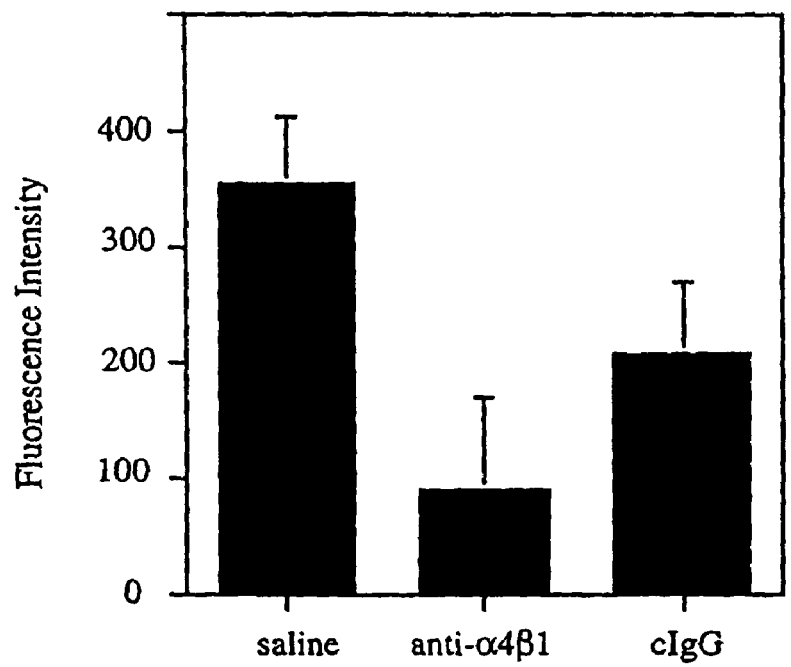
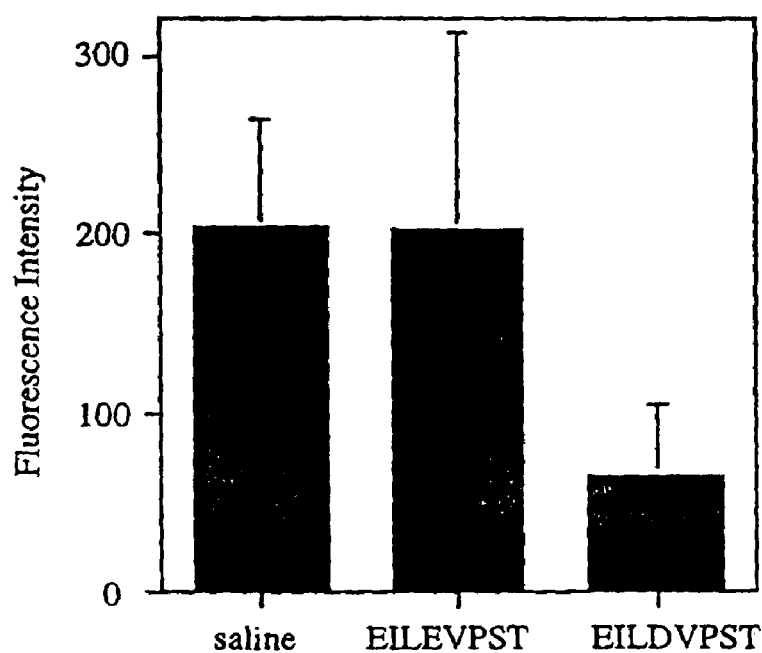

FIGURE 6

```
   1 mawearrepg prraavretv mlllclgvpt grpynvdtes allyqgphnt lfgysvvlhs
  61 hganrwllvg aptanwlana svinpgaiyr crigknpgqt ceqlqlgspn gepcgktcle
 121 erdnqwlgvt lsrqpgengs ivtcghrwkn ifyiknenkl ptggcygvpp dlrtelskri
 181 apcyqdyvkk fgenfascqa gissfytkdl ivmgapgssy wtgslfvyni ttnkykafld
 241 kqnqvkfgsy lgysvgaghf rsqhttevvg gapqheqigk ayifsideke lnilhemkgk
 301 klgsyfgasv cavdlnadgf sdllvgapmq stireegrvf vyinsgsgav mnametnlvg
 361 sdkyaarfge sivnlgdidn dgfedvaiga pqeddlqgai yiyngradgi sstfsqrieg
 421 lqiskslsmf gqsisgqida dnngyvdvav gafrsdsavl lrtrpvvivd aslshpesvn
 481 rtkfdcveng wpsvcidltl cfsykgkevp gyivlfynms ldvnrkaesp prfyfssngt
 541 sdvitgsiqv ssreancrth qafmrkdvrd iltpiqieaa yhlgphvisk rsteefpplq
 601 pilqqkkekd imkktinfar fcahencsad lqvsakigfl kphenktyla vgsmktlmln
 661 vslfnagdda yettlhvklp vglyfikile leekqincev tdnsgvvqld csigyiyvdh
 721 lsridisfll dvsslsraee dlsitvhatc eneeemdnlk hsrvtvaipl kyevkltvhg
 781 fvnptsfvyg sndenepetc mvekmnltfh vintgnsmap nvsveimvpn sfspqtdklf
 841 nildvqtttg echfenyqrv caleqqksam qtlkgivrfl sktdkrllyc ikadphclnf
 901 lcnfgkmesg keasvhiqle grpsilemde tsalkfeira tgfpepnprv ielnkdenva
 961 hvlleglhhq rpkryftivi issslllgli vlllisyvmw kagffkrqyk silqeenrrd
1021 swsyinsksn dd
```

FIGURE 7

```
  1 mnlqpifwig lissvccvfa qtdenrclka nakscgeciq agpncgwctn stflqegmpt
 61 sarcddleal kkkgcppddi enprgskdik knknvtnrsk gtaeklkped ihqiqpqqlv
121 lrlrsgepqt ftlkfkraed ypidlyylmd lsysmkddle nvkslgtdlm nemrritsdf
181 rigfgsfvek tvmpyisttp aklrnpctse qncttpfsyk nvlsltnkge vfnelvgkqr
241 isgnldspeg gfdaimqvav cgsligwrnv trllvfstda gfhfagdgkl ggivlpndgq
301 chlennmytm shyydypsia hlvqklsenn iqtifavtee fqpvykelkn lipksavgtl
361 sanssnviql iidaynslss evilengkls egvtisyksy ckngvngtge ngrkcsnisi
421 gdevqfeisi tsnkcpkkds dsfkirplgf teevevilqy icececqseg ipespkcheg
481 ngtfecgacr cnegrvgrhc ecstdevnse dmdaycrken sseicsnnge cvcgqcvcrk
541 rdntneiysg kfcecdnfnc drsnglicgg ngvckcrvce cnpnytgsac dcsldtstce
601 asngqicngr gicecgvckc tdpkfqgqtc emcqtclgvc aehkecvqcr afnkgekkdt
661 ctqecsyfni tkvesrdklp qpvqpdpvsh ckekdvddcw fyftysvngn nevmvhvven
721 pecptgpdii pivagvvagi vliglallli wkllmiihdr refakfekek mnakwdtgen
781 piyksavttv vnpkyegk
```

FIGURE 8A

```
  1 mpgkmvvilg asnilwimfa asqafkiett pesrylaqig dsvsltcstt gcespffswr
 61 tqidsplngk vtnegttstl tmnpvsfgne hsylctatce srklekgiqv eiysfpkdpe
121 ihlsgpleag kpitvkcsva dvypfdrlei dllkgdhlmk sqefledadr ksletkslev
181 tftpviedig kvlvcraklh idemdsvptv rqavkelqvy ispkntvisv npstklqegg
241 svtmtcsseg lpapeifwsk kldngnlqhl sgnatltlia mrmedsgiyv cegvnligkn
301 rkevelivqe kpftveispg priaaqigds vmltcsvmgc espsfswrtq idsplsgkvr
361 segtnstltl spvsfenehs ylctvtcghk klekgiqvel ysfprdpeie msgglvngss
421 vtvsckvpsv ypldrleiel lkgetileni efledtdmks lenkslemtf iptiedtgka
481 lvcqaklhid dmefepkqrq stqtlyvnva prdttvlvsp ssileegssv nmtclsqgfp
541 apkilwsrql pngelqplse natltlistk medsgvylce ginqagrsrk eveliiqvtp
601 kdikltafps esvkegdtvi isctcgnvpe twiilkkkae tgdtvlksid gaytirkaql
661 kdagvyeces knkvgsqlrs ltldvqgren nkdyfspell vlyfasslii paigmiiyfa
721 rkanmkgsys lveaqkskv
```

FIGURE 8B

```
  1 mpgkmvvilg asnilwimfa asqafkiett pesrylaqig dsvsltcstt gcespffswr
 61 tqidsplngk vtnegttstl tmnpvsfgne hsylctatce srklekgiqv eiysfpkdpe
121 ihlsgpleag kpitvkcsva dvypfdrlei dllkgdhlmk sqefledadr ksletkslev
181 tftpviedig kvlvcraklh idemdsvptv rqavkelqvy ispkntvisv npstklqegg
241 svtmtcsseg lpapeifwsk kldngnlqhl sgnatltlia mrmedsgiyv cegvnligkn
301 rkevelivqa fprdpeiems gglvngssvt vsckvpsvyp ldrleiellk getilenief
361 ledtdmksle nkslemtfip tiedtgkalv cqaklhiddm efepkqrqst qtlyvnvapr
421 dttvlvspss ileegssvnm tclsqgfpap kilwsrqlpn gelqplsena tltlistkme
481 dsgvylcegi nqagrsrkev eliiqvtpkd ikltafpses vkegdtviis ctcgnvpetw
541 iilkkkaetg dtvlksidga ytirkaqlkd agvyeceskn kvgsqlrslt ldvqgrennk
601 dyfspellvl yfassliipa igmiiyfark anmkgsyslv eaqkskv
```

FIGURE 9

```
   1 mlrgpgpgll llavqclgta vpstgasksk rqaqqmvqpq spvavsqskp gcydngkhyq
  61 inqqwertyl gnalvctcyg gsrgfncesk peaeetcfdk ytgntyrvgd tyerpkdsmi
 121 wdctcigagr grisctianr cheggqsyki gdtwrrphet ggymlecvcl gngkgewtck
 181 piaekcfdha agtsyvvget wekpyqgwmm vdctclgegs gritctsrnr cndqdtrtsy
 241 rigdtwskkd nrgnllqcic tgngrgewkc erhtsvqtts sgsgpftdvr aavyqpqphp
 301 qpppyghcvt dsgvvysvgm qwlktqgnkq mlctclgngv scqetavtqt yggnsngepc
 361 vlpftyngrt fyscttegrq dghlwcstts nyeqdqkysf ctdhtvlvqt qggnsngalc
 421 hfpflynnhn ytdctsegrr dnmkwcgttq nydadqkfgf cpmaaheeic ttnegvmyri
 481 gdqwdkqhdm ghmmrctcvg ngrgewtcia ysqlrdqciv ddityvndt fhkrheeghm
 541 lnctcfgqgr grwkcdpvdq cqdsetgtfy qigdswekyv hgvryqcycy grgigewhcq
 601 plqtypsssg pvevfitetp sqpnshpiqw napqpshisk yilrwrpkns vgrwkeatip
 661 ghlnsytikg lkpgvvyegq lisiqqyghq evtrfdfttt ststpvtsnt vtgettpfsp
 721 lvatsesvte itassfvvsw vsasdtvsgf rveyelseeg depqyldlps tatsvnipdl
 781 lpgrkyivnv yqisedgeqs lilstsqtta pdappdptvd qvddtsivvr wsrpqapitg
 841 yrivyspsve gsstelnlpe tansvtlsdl qpgvqyniti yaveenqest pvviqqettg
 901 tprsdtvpsp rdlqfvevtd vkvtimwtpp esavtgyrvd vipvnlpgeh gqrlpisrnt
 961 faevtglspg vtyyfkvfav shgreskplt aqqttkldap tnlqfvnetd stvlvrwtpp
1021 raqitgyrlt vgltrrgqpr qynvgpsvsk yplrnlqpas eytvslvaik gnqespkatg
1081 vfttlqpgss ippyntevte ttivitwtpa prigfklgvr psqggeapre vtsdsgsivv
1141 sgltpgveyv ytiqvlrdgq erdapivnkv vtplspptnl hleanpdtgv ltvswerstt
1201 pditgyritt tptngqqgns leevvhadqs sctfdnlspg leynvsvytv kddkesvpis
1261 dtiipavppp tdlrftnigp dtmrvtwapp psidltnflv ryspvkneed vaelsispsd
1321 navvltnllp gteyvvsvss vyeqhestpl rgrqktglds ptgidfsdit ansftvhwia
1381 pratitgyri rhhpehfsgr predrvphsr nsitltnltp gteyvvsiva lngreespll
1441 igqqstvsdv prdlevvaat ptslliswda pavtvryyri tygetggnsp vqeftvpgsk
1501 statisglkp gvdytitvya vtgrgdspas skpisinyrt eidkpsqmqv tdvqdnsisv
1561 kwlpssspvt gyrvttttpkn gpgptktkta gpdqtemtie glqptveyvv svyaqnpsge
1621 sqplvqtavt nidrpkglaf tdvdvdsiki awespqgqvs ryrvtysspe dgihelfpap
1681 dgeedtaelq glrpgseytv svvalhddme sqpligtqst aipaptdlkf tqvtptslsa
1741 qwtppnvqlt gyrvrvtpke ktgpmkeinl apdsssvvvs glmvatkyev svyalkdtlt
1801 srpaqgvvtt lenvspprra rvtdatetti tiswrtktet itgfqvdavp angqtpiqrt
1861 ikpdvrsyti tglqpgtdyk iylytlndna rsspvvidas taidapsnlr flattpnsll
1921 vswqpprari tgyiikyekp gsppprevvpr prpgvteati tglepgteyt iyvialknnq
1981 ksepligrkk tdelpqlvtl phpnlhgpei ldvpstvqkt pfvthpgydt gngiqlpgts
2041 gqqpsvgqqm ifeehgfrrt tppttatpir hrprpyppnv geeiqighip redvdyhlyp
2101 hgpglnpnas tgqealsqtt iswapfqdts eyiischpvg tdeeplqfrv pgtstsatlt
2161 gltrgatyni ivealkdqqr hkvreevvtv gnsvneglnq ptddscfdpy tvshyavgde
2221 wermsesgfk llcqclgfgs ghfrcdssrw chdngvnyki gekwdrqgen gqmmsctclg
2281 ngkgefkcdp heatcyddgk tyhvgeqwqk eylgaicsct cfggqrgwrc dncrrpggep
2341 spegttgqsy nqysqryhqr tntnvncpie cfmpldvqad redsre
```

FIGURE 13 (A)

```
   1 gccatcccgc gctctgcggg ctgggaggcc cgggccagga cgcgagtcct gcgcagccga
  61 ggttccccag cgcccccctgc agccgcgcgt aggcagagac ggagcccggc cctgcgcctc
 121 cgcaccacgc ccgggacccc acccagcggc ccgtacccgg agaagcagcg cgagcacccg
 181 aagctcccgg ctggcggcag aaaccgggag tggggccggg cgagtgcgcg gcatccagg
 241 ccggcccgaa cgctccgccc gcggtgggcc gacttcccct cctcttccct ctctccttcc
 301 tttagcccgc tgccgccgga cacgctgcgc ctcatctctt ggggcgttct tccccgttgg
 361 ccaaccgtcg catcccgtgc aactttgggg tagtggccgt ttagtgttga atgttcccca
 421 ccgagagcgc atggcttggg aagcgaggcg cgaacccggc ccccgaaggg ccgccgtccg
 481 ggagacggtg atgctgttgc tgtgcctggg ggtcccgacc ggccgcccct acaacgtgga
 541 cactgagagc gcgctgcttt accagggccc ccacaacacg ctgttcggct actcggtcgt
 601 gctgcacagc cacggggcga accgatggct cctagtgggt gcgcccactg ccaactggct
 661 cgccaacgct tcagtgatca atcccggggc gatttacaga tgcaggatcg aaagaatcc
 721 cggccagacg tgcgaacagc tccagctggg tagccctaat ggagaacctt gtggaaagac
 781 ttgtttggaa gagagagaca atcagtggtt ggggtcaca ctttccagac agccaggaga
 841 aaatggatcc atcgtgactt gtgggcatag atggaaaaat atattttaca taaagaatga
 901 aaataagctc cccactggtg gttgctatgg agtgcccct gatttacgaa cagaactgag
 961 taaaagaata gctccgtgtt atcaagatta tgtgaaaaaa tttggagaaa attttgcatc
1021 atgtcaagct ggaatatcca gtttttacac aaaggattta attgtgatgg gggcccagg
1081 atcatcttac tggactggct ctcttttttgt ctacaatata actacaaata aatacaaggc
1141 ttttttagac aaacaaaatc aagtaaaatt tggaagttat ttaggatatt cagtcggagc
1201 tggtcatttt cggagccagc atactaccga agtagtcgga ggagctcctc aacatgagca
1261 gattggtaag gcatatatat tcagcattga tgaaaaagaa ctaaatatct tacatgaaat
1321 gaaaggtaaa aagcttggat cgtactttgg agcttctgtc tgtgctgtgg acctcaatgc
1381 agatggcttc tcagatctgc tcgtgggagc acccatgcag agcaccatca gagaggaagg
1441 aagagtgttt gtgtacatca actctggctc gggagcagta atgaatgcaa tggaaacaaa
1501 cctcgttgga agtgacaaat atgctgcaag atttggggaa tctatagtta atcttggcga
1561 cattgacaat gatggctttg aagatgttgc tatcggagct ccacaagaag atgacttgca
1621 aggtgctatt tatatttaca atggccgtgc agatgggatc tcgtcaacct tctcacagag
1681 aattgaagga cttcagatca gcaaatcgtt aagtatgttt ggacagtcta tatcaggaca
1741 aattgatgca gataataatg gctactgaga tgtagcagtt ggtgcttttc ggtctgattc
1801 tgctgtcttg ctaaggacaa gacctgtagt aattgttgac gcttctttaa gccaccctga
1861 gtcagtaaat agaacgaaat ttgactgtgt tgaaaatgga tggccttctg tgtgcataga
1921 tctaacactt tgtttctcat ataagggcaa ggaagttcca ggttacattg ttttgttta
1981 taacatgagt ttggatgtga acagaaaggc agagtctcca ccaagattct atttctcttc
2041 taatggaact tctgacgtga ttacaggaag catacaggtg tccagcagag aagctaactg
2101 tagaacacat caagcattta tgcggaaaga tgtgcgggac atcctcaccc caattcagat
2161 tgaagctgct taccaccttg gtcctcatgt catcagtaaa cgaagtacag aggaattccc
2221 accacttcag ccaattcttc agcagaagaa agaaaaagac ataatgaaaa aaacaataaa
2281 ctttgcaagg ttttgtgccc atgaaaattg ttctgctgat ttacaggttt ctgcaaagat
2341 tgggtttttg aagccccatg aaaataaaac atatcttgct gttgggagta tgaagacatt
2401 gatgttgaat gtgtccttgt ttaatgctgg agatgatgca tatgaaacga ctctacatgt
2461 caaactaccc gtgggtcttt atttcattaa gatttagag ctggaagaga agcaaataaa
2521 ctgtgaagtc acagataact ctggcgtggt acaacttgac tgcagtattg gctatatata
```

FIGURE 13 (B)

```
2581 tgtagatcat ctctcaagga tagatattag ctttctcctg gatgtgagct cactcagcag
2641 agcggaagag gacctcagta tcacagtgca tgctacctgt gaaaatgaag aggaaatgga
2701 caatctaaag cacagcagag tgactgtagc aataccttta aaatatgagg ttaagctgac
2761 tgttcatggg tttgtaaacc caacttcatt tgtgtatgga tcaaatgatg aaaatgagcc
2821 tgaaacgtgc atggtggaga aaatgaactt aactttccat gttatcaaca ctggcaatag
2881 tatggctccc aatgttagtg tggaaataat ggtaccaaat tcttttagcc cccaaactga
2941 taagctgttc aacattttgg atgtccagac tactactgga gaatgccact ttgaaaatta
3001 tcaaagagtg tgtgcattag agcagcaaaa gagtgcaatg cagaccttga aaggcatagt
3061 ccggttcttg tccaagactg ataagaggct attgtactgc ataaaagctg atccacattg
3121 tttaaatttc ttgtgtaatt ttgggaaaat ggaaagtgga aagaagcca gtgttcatat
3181 ccaactggaa ggccggccat ccattttaga aatggatgag acttcagcac tcaagtttga
3241 aataagagca acaggttttc cagagccaaa tccaagagta attgaactaa acaaggatga
3301 gaatgttgcg catgttctac tggaaggact acatcatcaa agacccaaac gttatttcac
3361 catagtgatt atttcaagta gcttgctact tggacttatt gtacttctat tgatctcata
3421 tgttatgtgg aaggctggct tctttaaaag acaatacaaa tctatcctac aagaagaaaa
3481 cagaagagac agttggagtt atatcaacag taaaagcaat gatgattaag gacttctttc
3541 aaattgagag aatggaaaac ag
```

FIGURE 14 (A)

```
   1 gccatcccgc gctctgcggg ctgggaggcc cgggccagga cgcgagtcct gcgcagccga
  61 ggttccccag cgccccctgc agccgcgcgt aggcagagac ggagcccggc cctgcgcctc
 121 cgcaccacgc ccgggacccc acccagcggc ccgtacccgg agaagcagcg cgagcacccg
 181 aagctcccgg ctggcggcag aaaccgggag tggggccggg cgagtgcgcg gcatcccagg
 241 ccggcccgaa cgctccgccc gcggtgggcc gacttcccct cctcttccct ctctccttcc
 301 tttagcccgc tggcgccgga cacgctgcgc ctcatctctt ggggcgttct tccccgttgg
 361 ccaaccgtcg catcccgtgc aactttgggg tagtggccgt ttagtgttga atgttcccca
 421 ccgagagcgc atggcttggg aagcgaggcg cgaacccggc ccccgaaggg ccgccgtccg
 481 ggagacggtg atgctgttgc tgtgcctggg ggtcccgacc ggccgcccct acaacgtgga
 541 cactgagagc gcgctgcttt accagggccc ccacaacacg ctgttcggct actcggtcgt
 601 gctgcacagc cacggggcga accgatggct cctagtgggt gcgcccactg ccaactggct
 661 cgccaacgct tcagtgatca atcccggggc gatttacaga tgcaggatcg gaaagaatcc
 721 cggccagacg tgcgaacagc tccagctggg tagccctaat ggagaacctt gtggaaagac
 781 ttgtttggaa gagagagaca atcagtggtt gggggtcaca ctttccagac agccaggaga
 841 aaatggatcc atcgtgactt gtgggcatag atggaaaaat atattaca taaagaatga
 901 aaataagctc cccactggtg gttgctatgg agtgcccct gatttacgaa cagaactgag
 961 taaaagaata gctccgtgtt atcaagatta tgtgaaaaaa tttggagaaa attttgcatc
1021 atgtcaagct ggaatatcca gttttacac aaaggattta attgtgatgg gggcccagg
1081 atcatcttac tggactggct ctctttttgt ctacaatata actacaaata aatacaaggc
1141 tttttagac aaacaaaatc aagtaaaatt tggaagttat ttaggatatt cagtcggagc
1201 tggtcatttt cggagccagc atactaccga agtagtcgga ggagctcctc aacatgagca
1261 gattggtaag gcatatatat tcagcattga tgaaaaagaa ctaaatatct tacatgaaat
1321 gaaaggtaaa aagcttggat cgtactttgg agcttctgtc tgtgctgtgg acctcaatgc
1381 agatggcttc tcagatctgc tcgtgggagc acccatgcag agcaccatca gagaggaagg
1441 aagagtgttt gtgtacatca actctggctc gggagcagta atgaatgcaa tggaaacaaa
1501 cctcgttgga agtgacaaat atgctgcaag atttggggaa tctatagtta atcttggcga
1561 cattgacaat gatggctttg aagatgttgc tatcggagct ccacaagaag atgacttgca
1621 aggtgctatt tatatttaca atggccgtgc agatgggatc tcgtcaacct tctcacagag
1681 aattgaagga cttcagatca gcaaatcgtt aagtatgttt ggacagtcta tatcaggaca
1741 aattgatgca gataataatg gctatgtaga tgtagcagtt ggtgcttttc ggtctgattc
1801 tgctgtcttg ctaaggacaa gacctgtagt aattgttgac gcttctttaa gccaccctga
1861 gtcagtaaat agaacgaaat ttgactgtgt tgaaaatgga tggccttctg tgtgcataga
1921 tctaacacatt tgtttctcat ataagggcaa ggaagttcca ggttacattg tttgtttta
1981 taacatgagt ttggatgtga acagaaaggc agagtctcca ccaagattct atttctcttc
2041 taatggaact tctgacgtga ttacaggaag catacaggtg tccagcagag aagctaactg
2101 tagaacacat caagcattta tgcggaaaga tgtgcgggac atcctcaccc caattcagat
2161 tgaagctgct taccaccttg gtcctcatgt catcagtaaa cgaagtacag aggaattccc
2221 accacttcag ccaattcttc agcagaagaa agaaaagac ataatgaaaa aaacaataaa
2281 ctttgcaagg ttttgtgccc atgaaaattg ttctgctgat ttacaggttt ctgcaaagat
2341 tgggttttg aagccccatg aaaataaaac atatcttgct gttgggagta tgaagacatt
2401 gatgttgaat gtgtccttgt ttaatgctgg agatgatgca tatgaaacga ctctacatgt
2461 caaactaccc gtgggtcttt atttcattaa gattttagag ctggaagaga agcaaataaa
```

FIGURE 14 (B)

```
2521 ctgtgaagtc acagataact ctggcgtggt acaacttgac tgcagtattg gctatatata
2581 tgtagatcat ctctcaagga tagatattag ctttctcctg gatgtgagct cactcagcag
2641 agcggaagag gacctcagta tcacagtgca tgctacctgt gaaaatgaag aggaaatgga
2701 caatctaaag cacagcagag tgactgtagc aataccttta aaatatgagg ttaagctgac
2761 tgttcatggg tttgtaaacc caacttcatt tgtgtatgga tcaaatgatg aaaatgagcc
2821 tgaaacgtgc atggtggaga aaatgaactt aactttccat gttatcaaca ctggcaatag
2881 tatggctccc aatgttagtg tggaaataat ggtaccaaat tcttttagcc cccaaactga
2941 taagctgttc aacattttgg atgtccagac tactactgga gaatgccact ttgaaaatta
3001 tcaaagagtg tgtgcattag agcagcaaaa gagtgcaatg cagaccttga aaggcatagt
3061 ccggttcttg tccaagactg ataagaggct attgtactgc ataaaagctg atccacattg
3121 tttaaatttc ttgtgtaatt ttgggaaaat ggaaagtgga aaagaagcca gtgttcatat
3181 ccaactggaa ggccggccat ccattttaga aatggatgag acttcagcac tcaagtttga
3241 aataagagca acaggttttc cagagccaaa tccaagagta attgaactaa acaaggatga
3301 gaatgttgcg catgttctac tggaaggact acatcatcaa agacccaaac gttatttcac
3361 catagtgatt atttcaagta gcttgctact tggacttatt gtacttctat tgatctcata
3421 tgttatgtgg aaggctggct tctttaaaag acaatacaaa tctatcctac aagaagaaaa
3481 cagaagagac agttggagtt atatcaacag taaaagcaat gatgattaag gacttctttc
3541 aaattgagag aatggaaaac ag
```

FIGURE 15 (A)

```
   1 gtccgccaaa acctgcgcgg atagggaaga acagcacccc ggcgccgatt gccgtaccaa
  61 acaagcctaa cgtccgctgg gccccggacg ccgcgcggaa aagatgaatt tacaaccaat
 121 tttctggatt ggactgatca gttcagtttg ctgtgtgttt gctcaaacag atgaaaatag
 181 atgtttaaaa gcaaatgcca aatcatgtgg agaatgtata caagcagggc caaattgtgg
 241 gtggtgcaca aattcaacat ttttacagga aggaatgcct acttctgcac gatgtgatga
 301 tttagaagcc ttaaaaaaga agggttgccc tccagatgac atagaaaatc ccagaggctc
 361 caaagatata aagaaaaata aaaatgtaac caaccgtagc aaaggaacag cagagaagct
 421 caagccagag gatattcatc agatccaacc acagcagttg gttttgcgat taagatcagg
 481 ggagccacag acatttacat taaaattcaa gagagctgaa gactatccca ttgacctcta
 541 ctaccttatg gacctgtctt attcaatgaa agacgatttg gagaatgtaa aaagtcttgg
 601 aacagatctg atgaatgaaa tgaggaggat tacttcggac ttcagaattg gatttggctc
 661 atttgtggaa aagactgtga tgccttacat tagcacaaca ccagctaagc tcaggaaccc
 721 ttgcacaagt gaacagaact gcaccacccc atttagctac aaaaatgtgc tcagtcttac
 781 taataaagga gaagtattta atgaacttgt tggaaaacag cgcatatctg gaaatttgga
 841 ttctccagaa ggtggtttcg atgccatcat gcaagttgca gtttgtggat cactgattgg
 901 ctggaggaat gttacacggc tgctggtgtt ttccacagat gccgggtttc actttgctgg
 961 agatgggaaa cttggtggca ttgttttacc aaatgatgga caatgtcacc tggaaaataa
1021 tatgtacaca atgagccatt attatgatta tccttctatt gctcaccttg tccagaaact
1081 gagtgaaaat aatattcaga caatttttgc agttactgaa gaatttcagc ctgtttacaa
1141 ggagctgaaa aacttgatcc ctaagtcagc agtaggaaca ttatctgcaa attctagcaa
1201 tgtaattcag ttgatcattg atgcatacaa ttccctttcc tcagaagtca ttttggaaaa
1261 cggcaaattg tcagaaggag taacaataag ttacaaatct tactgcaaga acggggtgaa
1321 tggaacaggg gaaaatggaa gaaaatgttc caatatttcc attggagatg aggttcaatt
1381 tgaaattagc ataacttcaa ataagtgtcc aaaaaaggat tctgacagct ttaaaattag
1441 gcctctgggc tttacggagg aagtagaggt tattcttcag tacatctgtg aatgtgaatg
1501 ccaaagcgaa ggcatccctg aaagtcccaa gtgtcatgaa ggaaatggga catttgagtg
1561 tggcgcgtgc aggtgcaatg aagggcgtgt tggtagacat tgtgaatgca gcacagatga
1621 agttaacagt gaagacatgg atgcttactg caggaaagaa aacagttcag aaatctgcag
1681 taacaatgga gagtgcgtct gcggacagtg tgtttgtagg aagagggata atacaaatga
1741 aatttattct ggcaaattct gcgagtgtga taatttcaac tgtgatagat ccaatggctt
1801 aatttgtgga ggaaatggtg tttgcaagtg tcgtgtgtgt gagtgcaacc ccaactacac
1861 tggcagtgca tgtgactgtt ctttggatac tagtacttgt gaagccagca acggacagat
1921 ctgcaatggc cggggcatct gcgagtgtgg tgtctgtaag tgtacagatc cgaagtttca
1981 agggcaaacg tgtgagatgt gtcagacctg ccttggtgtc tgtgctgagc ataagaatg
2041 tgttcagtgc agagccttca ataaggaga aaagaaagac acatgcacac aggaatgttc
2101 ctatttaac attaccaagg tagaaagtcg ggacaaatta ccccagccgg tccaacctga
2161 tcctgtgtcc cattgtaagg agaaggatgt tgacgactgt tggttctatt ttacgtattc
2221 agtgaatggg aacaacgagg tcatggttca tgttgtggag aatccagagt gtcccactgg
2281 tccagacatc attccaattg tagctggtgt ggttgctgga attgttctta ttggccttgc
2341 attactgctg atatggaagc ttttaatgat aattcatgac agaagggagt ttgctaaatt
2401 tgaaaaggag aaaatgaatg ccaaatggga cacgggtgaa aatcctattt ataagagtgc
```

FIGURE 15 (B)

```
2461 cgtaacaact gtggtcaatc cgaagtatga gggaaaatga gtactgcccg tgcaaatccc
2521 acaacactga atgcaaagta gcaatttcca tagtcacagt taggtagctt tagggcaata
2581 ttgccatggt tttactcatg tgcaggtttt gaaaatgtac aatatgtata attttaaaa
2641 tgttttatta ttttgaaaat aatgttgtaa ttcatgccag ggactgacaa aagacttgag
2701 acaggatggt tattcttgtc agctaaggtc acattgtgcc ttttttgacct tttcttcctg
2761 gactattgaa atcaagctta ttggattaag tgatatttct atagcgattg aaagggcaat
2821 agttaaagta atgagcatga tgagagtttc tgttaatcat gtattaaaac tgatttttag
2881 ctttacatat gtcagtttgc agttatgcag aatccaaagt aaatgtcctg ctagctagtt
2941 aaggattgtt ttaaatctgt tattttgcta tttgcctgtt agacatgact gatgacatat
3001 ctgaaagaca agtatgttga gagttgctgg tgtaaaatac gtttgaaata gttgatctac
3061 aaaggccatg ggaaaaattc agagagttag gaaggaaaaa ccaatagctt taaaacctgt
3121 gtgccatttt aagagttact taatgtttgg taacttttat gccttcactt tacaaattca
3181 agccttagat aaaagaaccg agcaattttc tgctaaaaag tccttgattt agcactattt
3241 acatacaggc catactttac aaagtatttg ctgaatgggg acctttgag ttgaatttat
3301 tttattattt ttattttgtt taatgtctgg tgctttctat caccttcttc aatctttaa
3361 tgtatttgtt tgcaattttg gggtaagact tttttatgag tacttttct ttgaagtttt
3421 agcggtcaat ttgcctttt aatgaacatg tgaagttata ctgtggctat gcaacagctc
3481 tcacctacgc gagtcttact ttgagttagt gccataacag accactgtat gtttacttct
3541 caccatttga gttgcccatc ttgtttcaca ctagtcacat tcttgtttta agtgcctta
3601 gttttaacag ttca
```

FIGURE 16

```
   1 atgcctggga agatggtcgt gatccttgga gcctcaaata tactttggat aatgtttgca
  61 gcttctcaag cttttaaaat cgagaccacc ccagaatcta gatatcttgc tcagattggt
 121 gactccgtct cattgacttg cagcaccaca ggctgtgagt ccccattttt ctcttggaga
 181 acccagatag atagtccact gaatgggaag gtgacgaatg aggggaccac atctacgctg
 241 acaatgaatc ctgttagttt tgggaacgaa cactcttacc tgtgcacagc aacttgtgaa
 301 tctaggaaat tggaaaaagg aatccaggtg gagatctact cttttcctaa ggatccagag
 361 attcatttga gtggccctct ggaggctggg aagccgatca cagtcaagtg ttcagttgct
 421 gatgtatacc catttgacag gctggagata gacttactga aaggagatca tctcatgaag
 481 agtcaggaat ttctggagga tgcagacagg aagtccctgg aaaccaagag tttggaagta
 541 acctttactc ctgtcattga ggatattgga aaagttcttg tttgccgagc taattacac
 601 attgatgaaa tggattctgt gcccacagta aggcaggctg taaaagaatt gcaagtctac
 661 atatcaccca agaatacagt tatttctgtg aatccatcca caaagctgca agaaggtggc
 721 tctgtgacca tgacctgttc cagcgagggt ctaccagctc cagagatttt ctggagtaag
 781 aaattagata tgggaatct acagcaccett tctggaaatg caactctcac cttaattgct
 841 atgaggatgg aagattctgg aatttatgtg tgtgaaggag ttaatttgat tgggaaaaac
 901 agaaaagagg tggaattaat tgttcaagag aaaccattta ctgttgagat ctcccctgga
 961 ccccggattg ctgctcagat tggagactca gtcatgttga catgtagtgt catgggctgt
1021 gaatccccat ctttctcctg gagaacccag atagacagcc ctctgagcgg gaaggtgagg
1081 agtgagggga ccaattccac gctgaccctg agccctgtga gttttgagaa cgaacactct
1141 tatctgtgca cagtgacttg tggacataag aaactggaaa agggaatcca ggtggagctc
1201 tactcattcc ctagagatcc agaaatcgag atgagtggtg gcctcgtgaa tgggagctct
1261 gtcactgtaa gctgcaaggt tcctagcgtg tacccccttg accggctgga gattgaatta
1321 cttaagggg agactattct ggagaatata gagttttgg aggatacgga tatgaaatct
1381 ctagagaaca aaagtttgga aatgaccttc atccctacca ttgaagatac tggaaaagct
1441 cttgtttgtc aggctaagtt acatattgat gacatggaat tcgaacccaa acaaaggcag
1501 agtacgcaaa cactttatgt caatgttgcc cccagagata caaccgtctt ggtcagccct
1561 tcctccatcc tggaggaagg cagttctgtg aaatatgacat gcttgagcca gggctttcct
1621 gctccgaaaa tcctgtggag caggcagctc cctaacgggg agctacagcc tctttctgag
1681 aatgcaactc tcaccttaat ttctacaaaa atggaagatt ctggggttta tttatgtgaa
1741 ggaattaacc aggctggaag aagcagaaag gaagtggaat taattatcca agttactcca
1801 aaagacataa aacttacagc ttttccttct gagagtgtca agaaggaga cactgtcatc
1861 atctcttgta catgtggaaa tgttccagaa acatggataa tcctgaagaa aaaagcggag
1921 acaggagaca cagtactaaa atctatagat ggcgcctata ccatccgaaa ggcccagttg
1981 aaggatgcgg gagtatatga atgtgaatct aaaaacaaag ttggctcaca attaagaagt
2041 ttaacacttg atgttcaagg aagagaaaac aacaaagact attttctcc tgagcttctc
2101 gtgctctatt ttgcatcctc cttaataata cctgccattg gaatgataat ttactttgca
2161 agaaaagcca acatgaaggg tcatatagt cttgtagaag cacagaaatc aaaagtgtag
```

FIGURE 17 (A)

```
   1 gaagagcaag aggcaggctc agcaaatggt tcagccccag tccccggtgg ctgtcagtca
  61 aagcaagccc ggttgttatg acaatggaaa acactatcag ataaatcaac agtgggagcg
 121 gacctaccta ggtaatgtgt tggtttgtac ttgttatgga ggaagccgag gttttaactg
 181 cgaaagtaaa cctgaagctg aagagacttg ctttgacaag tacactggga acacttaccg
 241 agtgggtgac acttatgagc gtcctaaaga ctccatgatc tgggactgta cctgcatcgg
 301 ggctgggcga gggagaataa gctgtaccat cgcaaaccgc tgccatgaag ggggtcagtc
 361 ctacaagatt ggtgacacct ggaggagacc acatgagact ggtggttaca tgttagagtg
 421 tgtgtgtctt ggtaatggaa aaggagaatg gacctgcaag cccatagctg agaagtgttt
 481 tgatcatgct gctgggactt cctatgtggt cggagaaacg tgggagaagc cctaccaagg
 541 ctggatgatg gtagattgta cttgcctggg agaaggcagc ggacgcatca cttgcacttc
 601 tagaaataga tgcaacgatc aggacacaag gacatcctat agaattggag acacctggag
 661 caagaaggat aatcgaggaa acctgctcca gtgcatctgc acaggcaacg ccgaggaga
 721 gtggaagtgt gagaggcaca cctctgtgca gaccacatcg agcggatctg gccccttcac
 781 cgatgttcgt gcagctgttt accaaccgca gcctcacccc cagcctcctc cctatggcca
 841 ctgtgtcaca gacagtggtg tggtctactc tgtggggatg cagtggttga agacacaagg
 901 aaataagcaa atgctttgca cgtgcctggg caacggagtc agctgccaag agacagctgt
 961 aacccagact tacggtggca acttaaatgg agagccatgt gtcttaccat tcacctacaa
1021 tggcaggacg ttctactcct gcaccacgga agggcgacag gacggacatc tttggtgcag
1081 cacaacttcg aattatgagc aggaccagaa atactctttc tgcacagacc acactgtttt
1141 ggttcagact caaggaggaa attccaatgg tgccttgtgc cacttcccct tcctatacaa
1201 caaccacaat tacactgatt gcacttctga gggcagaaga gacaacatga gtggtgtgg
1261 gaccacacag aactatgatg ccgaccagaa gtttgggttc tgccccatgg ctgcccacga
1321 ggaaatctgc acaaccaatg aaggggtcat gtaccgcatt ggagatcagt gggataagca
1381 gcatgacatg ggtcacatga tgaggtgcac gtgtgttggg aatggtcgtg gggaatggac
1441 atgcattgcc tactcgcaac ttcgagatca gtgcattgtt gatgacatca cttacaatgt
1501 gaacgacaca ttccacaagc gtcatgaaga ggggcacatg ctgaactgta catgcttcgg
1561 tcagggtcgg ggcaggtgga agtgtgatcc cgtcgaccaa tgccaggatt cagagactgg
1621 gacgttttat caaattggag attcatggga gaagtatgtg catggtgtca gataccagtg
1681 ctactgctat ggccgtggca ttgggggagtg gcattgccaa cctttacaga cctatccaag
1741 ctcaagtggt cctgtcgaag tatttatcac tgagactccg agtcagccca actcccaccc
1801 catccagtgg aatgcaccac agccatctca catttccaag tacattctca ggtggagacc
1861 taaaaattct gtaggccgtt ggaaggaagc taccatacca ggccacttaa actcctacac
1921 catcaaaggc ctgaagcctg gtgtggtata cgagggccag ctcatcagca tccagcagta
1981 cggccaccaa gaagtgactc gctttgactt caccaccacc agcaccagca cactgtgac
2041 cagcaacacc gtgacaggag agacgactcc ctttctcct cttgtggcca ttctgaatc
2101 tgtgaccgaa atcacagcca gtagctttgt ggtctcctgg gtctcagctt ccgacaccgt
2161 gtcgggattc cgggtggaat atgagctgag tgaggaggga gatgagccac agtacctgga
2221 tcttccaagc acagccactt ctgtgaacat ccctgacctg cttcctggcc gaaaatacat
2281 tgtaaatgtc tatcagatat ctgaggatgg ggagcagagt ttgatcctgt ctacttcaca
2341 aacaacagcg cctgatgccc ctcctgaccc gactgtggac caagttgatg acacctcaat
2401 tgttgttcgc tggagcagac cccaggctcc catcacaggg tacagaatag tctattcgcc
2461 atcagtagaa ggtagcagca cagaactcaa ccttcctgaa actgcaaact ccgtcaccct
2521 cagtgacttg caacctggtg ttcagtataa catcactatc tatgctgtgg aagaaaatca
```

FIGURE 17 (B)

```
2581 agaaagtaca cctgttgtca ttcaacaaga aaccactggc accccacgct cagatacagt
2641 gccctctccc agggacctgc agtttgtgga agtgacagac gtgaaggtca ccatcatgtg
2701 gacaccgcct gagagtgcag tgaccggcta ccgtgtggat gtgatccccg tcaacctgcc
2761 tggcgagcac gggcagaggc tgcccatcag caggaacacc tttgcagaag tcaccgggct
2821 gtcccctggg gtcacctatt acttcaaagt ctttgcagtg agccatggga gggagagcaa
2881 gcctctgact gctcaacaga caaccaaact ggatgctccc actaacctcc agtttgtcaa
2941 tgaaactgat tctactgtcc tggtgagatg gactccacct cgggcccaga taacaggata
3001 ccgactgacc gtgggcctta cccgaagagg ccagcccagg cagtacaatg tgggtccctc
3061 tgtctccaag taccccctga ggaatctgca gcctgcatct gagtacaccg tatccctcgt
3121 ggccataaag ggcaaccaag agagccccaa agccactgga gtctttacca cactgcagcc
3181 tgggagctct attccacctt acaacaccga ggtgactgag accaccatcg tgatcacatg
3241 gacgcctgct ccaagaattg gttttaagct gggtgtacga ccaagccagg gaggagaggc
3301 accacgagaa gtgacttcag actcaggaag catcgttgtg tccggcttga ctccaggagt
3361 agaatacgtc tacaccatcc aagtcctgag agatggacag gaaagagatg cgccaattgt
3421 aaacaaagtg gtgacaccat tgtctccacc aacaaacttg catctggagg caaaccctga
3481 cactggagtg ctcacagtct cctgggagag gagcaccacc ccagacatta ctggttatag
3541 aattaccaca accctacaa acggccagca gggaaattcc ttggaagaag tggtccatgc
3601 tgatcagagc tcctgcactt ttgataacct gagtcccggc ctggagtaca atgtcagtgt
3661 ttacactgtc aaggatgaca aggaaagtgt ccctatctct gataccatca tcccagctgt
3721 tcctcctccc actgacctgc gattcaccaa cattggtcca gacaccatgc gtgtcacctg
3781 ggctccaccc ccatccattg atttaaccaa cttcctggtg cgttactcac ctgtgaaaaa
3841 tgaggaagat gttgcagagt tgtcaatttc tccttcagac aatgcagtgg tcttaacaaa
3901 tctcctgcct ggtacagaat atgtagtgag tgtctccagt gtctacgaac aacatgagag
3961 cacacctctt agaggaagac agaaaacagg tcttgattcc ccaactggca ttgacttttc
4021 tgatattact gccaactctt ttactgtgca ctggattgct cctcgagcca ccatcactgg
4081 ctacaggatc cgccatcatc ccgagcactt cagtgggaga cctcgagaag atcgggtgcc
4141 ccactctcgg aattccatca ccctcaccaa cctcactcca ggcacagagt atgtggtcag
4201 catcgttgct cttaatggca gagaggaaag tccttattg attggccaac aatcaacagt
4261 ttctgatgtt ccgagggacc tggaagttgt tgctgcgacc cccaccagcc tactgatcag
4321 ctgggatgct cctgctgtca cagtgagata ttacaggatc acttacggag aaacaggagg
4381 aaatagccct gtccaggagt tcactgtgcc tgggagcaag tctacagcta ccatcagcgg
4441 ccttaaacct ggagttgatt ataccatcac tgtgtatgct gtcactggcc gtggagacag
4501 cccccgcaagc agcaagccaa tttccattaa ttaccgaaca gaaattgaca aaccatccca
4561 gatgcaagtg accgatgttc aggacaacag cattagtgtc aagtggctgc cttcaagttc
4621 ccctgttact ggttacagag taaccaccac tcccaaaaat ggaccaggac caacaaaaac
4681 taaaactgca ggtccagatc aaacagaaat gactattgaa ggcttgcagc ccacagtgga
4741 gtatgtggtt agtgtctatg ctcagaatcc aagcggagag agtcagcctc tggttcagac
4801 tgcagtaacc aacattgatc gccctaaagg actggcattc actgatgtgg atgtcgattc
4861 catcaaaatt gcttgggaaa gcccacaggg gcaagtttcc aggtacaggg tgacctactc
4921 gagccctgag gatggaatcc atgagctatt ccctgcacct gatggtgaag aagacactgc
4981 agagctgcaa ggcctcagac cgggttctga gtacacagtc agtgtggttg ccttgcacga
5041 tgatatggag agccagcccc tgattggaac ccagtccaca gctattcctg caccaactga
```

FIGURE 17 (C)

```
5101 cctgaagttc actcaggtca cacccacaag cctgagcgcc cagtggacac cacccaatgt
5161 tcagctcact ggatatcgag tgcgggtgac ccccaaggag aagaccggac caatgaaaga
5221 aatcaacctt gctcctgaca gctcatccgt ggttgtatca ggacttatgg tggccaccaa
5281 atatgaagtg agtgtctatg ctcttaagga cactttgaca agcagaccag ctcagggtgt
5341 tgtcaccact ctggagaatg tcagcccacc aagaagggct cgtgtgacag atgctactga
5401 gaccaccatc accattagct ggagaaccaa gactgagacg atcactggct tccaagttga
5461 tgccgttcca gccaatggcc agactccaat ccagagaacc atcaagccag atgtcagaag
5521 ctacaccatc acaggtttac aaccaggcac tgactacaag atctacctgt acaccttgaa
5581 tgacaatgct cggagctccc ctgtggtcat cgacgcctcc actgccattg atgcaccatc
5641 caacctgcgt ttcctggcca ccacacccaa ttccttgctg gtatcatggc agccgccacg
5701 tgccaggatt accggctaca tcatcaagta tgagaagcct gggtctcctc cagagaagt
5761 ggtccctcgg ccccgccctg gtgtcacaga ggctactatt actggcctgg aaccgggaac
5821 cgaatataca atttatgtca ttgccctgaa gaataatcag aagagcgagc ccctgattgg
5881 aaggaaaaag acagacgagc ttccccaact ggtaacccett ccacacccca atcttcatgg
5941 accagagatc ttggatgttc cttccacagt tcaaaagacc cctttcgtca cccaccctgg
6001 gtatgacact ggaaatggta ttcagcttcc tgcacttct ggtcagcaac ccagtgttgg
6061 gcaacaaatg atctttgagg aacatggttt taggcggacc acaccgccca caacggccac
6121 ccccataagg cataggccaa gaccataccc gccgaatgta ggacaagaag ctctctctca
6181 gacaaccatc tcatgggccc cattccagga cacttctgag tacatcattt catgtcatcc
6241 tgttggcact gatgaagaac ccttacagtt cagggttcct ggaacttcta ccagtgccac
6301 tctgacaggc ctcaccagag gtgccaccta caacatcata gtggaggcac tgaaagacca
6361 gcagaggcat aaggttcggg aagaggttgt taccgtgggc aactctgtca acgaaggctt
6421 gaaccaacct acggatgact cgtgctttga cccctacaca gtttcccatt atgccgttgg
6481 agatgagtgg gaacgaatgt ctgaatcagg ctttaaactg ttgtgccagt gcttaggctt
6541 tggaagtggt catttcagat gtgattcatc tagatggtgc catgacaatg gtgtgaacta
6601 caagattgga gagaagtggg accgtcaggg agaaaatggc cagatgatga gctgcacatg
6661 tcttgggaac ggaaaaggag aattcaagtg tgaccctcat gaggcaacgt gttacgatga
6721 tgggaagaca taccacgtag gagaacagtg gcagaaggaa tatctcggtg ccatttgctc
6781 ctgcacatgc tttggaggcc agcggggctg gcgctgtgac aactgccgca gacctggggg
6841 tgaacccagt cccgaaggca ctactggcca gtcctacaac cagtattctc agagatacca
6901 tcagagaaca aacactaatg ttaattgccc aattgagtgc ttcatgcctt tagatgtaca
6961 ggctgacaga gaagattccc gagagtaaat catctttcca atccagagga acaagcatgt
7021 ctctctgcca agatccatct aaactggagt gatgttagca gacccagctt agagttcttc
7081 tttcttttctt aagcccttg ctctggagga agttctccag cttcagctca actcacagct
7141 tctccaagca tcaccctggg agtttcctga gggttttctc ataaatgagg gctgcacatt
7201 gcctgttctg cttcgaagta ttcaataccg ctcagtattt taaatgaagt gattctaaga
7261 tttggtttgg gatcaatagg aaagcatatg cagccaacca agatgcaaat gttttgaaat
7321 gatatgacca aaattttaag taggaaagtc acccaaacac ttctgctttc acttaagtgt
7381 ctggcccgca atactgtagg aacaagcatg atcttgttac tgtgatattt taaatatcca
7441 cagtactcac tttttccaaa tgatcctagt aattgcctag aaatatcttt ctcttacctg
7501 ttatttatca atttttccca gtatttttat acggaaaaaa ttgtattgaa aacacttagt
7561 atgcagttga taagaggaat ttggtataat tatggtgggt gattattttt tatactgtat
7621 gtgccaaagc tttactactg tggaaagaca actgttttaa taaaagattt acattccaca
```

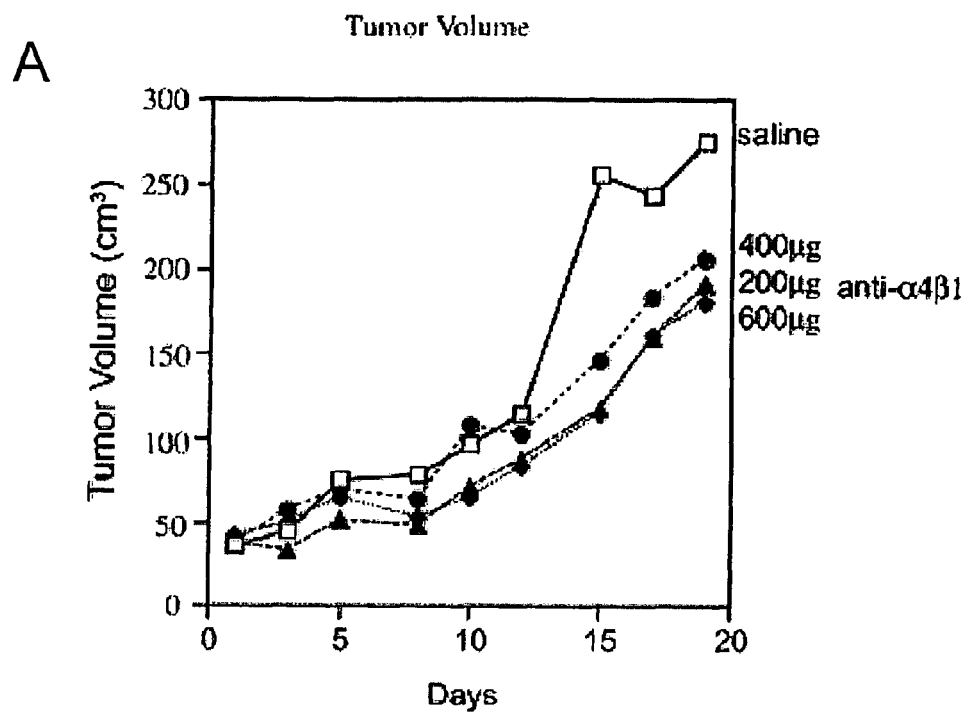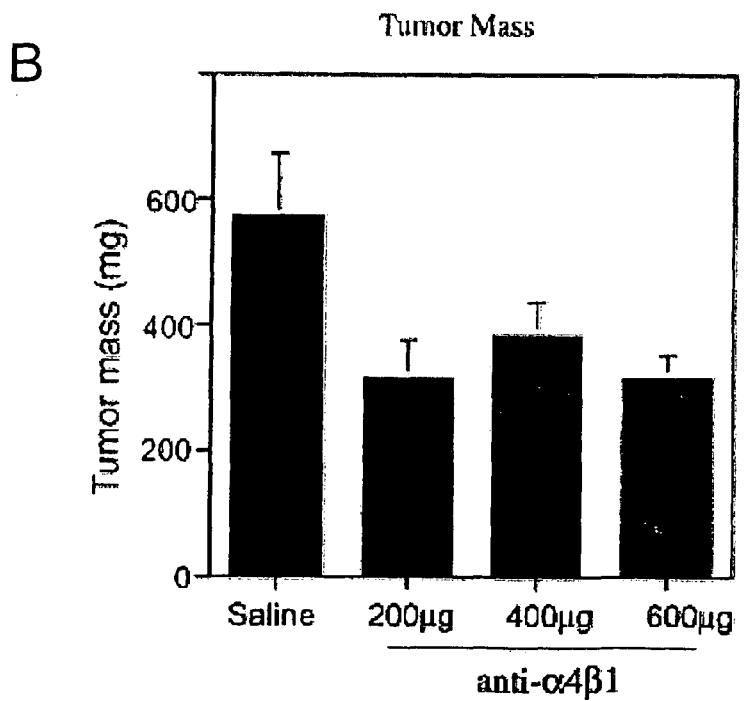
Figure 22

SEQUENCE LISTING

<160> NUMBER OF SEQ ID NOS: 97

<210> SEQ ID NO 1
<211> LENGTH: 1032
<212> TYPE: PRT
<213> ORGANISM: Homo sapiens

<400> SEQUENCE: 1

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe

-continued

```
            355                 360                 365
Gly Glu Ser Ile Val Asn Leu Gly Asp Ile Asp Asn Asp Gly Phe Glu
            370                 375                 380
Asp Val Ala Ile Gly Ala Pro Gln Glu Asp Asp Leu Gln Gly Ala Ile
385                 390                 395                 400
Tyr Ile Tyr Asn Gly Arg Ala Asp Gly Ile Ser Ser Thr Phe Ser Gln
                    405                 410                 415
Arg Ile Glu Gly Leu Gln Ile Ser Lys Ser Leu Ser Met Phe Gly Gln
                420                 425                 430
Ser Ile Ser Gly Gln Ile Asp Ala Asp Asn Asn Gly Tyr Val Asp Val
            435                 440                 445
Ala Val Gly Ala Phe Arg Ser Asp Ser Ala Val Leu Leu Arg Thr Arg
450                 455                 460
Pro Val Ile Val Asp Ala Ser Leu Ser His Pro Glu Ser Val Asn
465                 470                 475                 480
Arg Thr Lys Phe Asp Cys Val Glu Asn Gly Trp Pro Ser Val Cys Ile
                485                 490                 495
Asp Leu Thr Leu Cys Phe Ser Tyr Lys Gly Lys Glu Val Pro Gly Tyr
                500                 505                 510
Ile Val Leu Phe Tyr Asn Met Ser Leu Asp Val Asn Arg Lys Ala Glu
                515                 520                 525
Ser Pro Pro Arg Phe Tyr Phe Ser Ser Asn Gly Thr Ser Asp Val Ile
            530                 535                 540
Thr Gly Ser Ile Gln Val Ser Ser Arg Glu Ala Asn Cys Arg Thr His
545                 550                 555                 560
Gln Ala Phe Met Arg Lys Asp Val Arg Asp Ile Leu Thr Pro Ile Gln
                565                 570                 575
Ile Glu Ala Ala Tyr His Leu Gly Pro His Val Ile Ser Lys Arg Ser
                580                 585                 590
Thr Glu Glu Phe Pro Pro Leu Gln Pro Ile Leu Gln Gln Lys Lys Glu
            595                 600                 605
Lys Asp Ile Met Lys Lys Thr Ile Asn Phe Ala Arg Phe Cys Ala His
610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
                645                 650                 655
Leu Met Leu Asn Val Ser Leu Phe Asn Ala Gly Asp Asp Ala Tyr Glu
                660                 665                 670
Thr Thr Leu His Val Lys Leu Pro Val Gly Leu Tyr Phe Ile Lys Ile
            675                 680                 685
Leu Glu Leu Glu Glu Lys Gln Ile Asn Cys Glu Val Thr Asp Asn Ser
            690                 695                 700
Gly Val Val Gln Leu Asp Cys Ser Ile Gly Tyr Ile Tyr Val Asp His
705                 710                 715                 720
Leu Ser Arg Ile Asp Ile Ser Phe Leu Leu Asp Val Ser Ser Leu Ser
                725                 730                 735
Arg Ala Glu Glu Asp Leu Ser Ile Thr Val His Ala Thr Cys Glu Asn
                740                 745                 750
Glu Glu Glu Met Asp Asn Leu Lys His Ser Arg Val Thr Val Ala Ile
            755                 760                 765
Pro Leu Lys Tyr Glu Val Lys Leu Thr Val His Gly Phe Val Asn Pro
            770                 775                 780
```

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
            805                 810                 815

Ser Met Ala Pro Asn Val Ser Val Glu Ile Met Val Pro Asn Ser Phe
        820                 825                 830

Ser Pro Gln Thr Asp Lys Leu Phe Asn Ile Leu Asp Val Gln Thr Thr
    835                 840                 845

Thr Gly Glu Cys His Phe Glu Asn Tyr Gln Arg Val Cys Ala Leu Glu
850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
            885                 890                 895

Cys Leu Asn Phe Leu Cys Asn Phe Gly Lys Met Glu Ser Gly Lys Glu
        900                 905                 910

Ala Ser Val His Ile Gln Leu Glu Gly Arg Pro Ser Ile Leu Glu Met
    915                 920                 925

Asp Glu Thr Ser Ala Leu Lys Phe Glu Ile Arg Ala Thr Gly Phe Pro
930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
            965                 970                 975

Thr Ile Val Ile Ile Ser Ser Leu Leu Leu Gly Leu Ile Val Leu
        980                 985                 990

Leu Leu Ile Ser Tyr Val Met Trp Lys Ala Gly Phe Phe Lys Arg Gln
    995                 1000                1005

Tyr Lys Ser Ile Leu Gln Glu Glu Asn Arg Arg Asp Ser Trp Ser
    1010                1015                1020

Tyr Ile Asn Ser Lys Ser Asn Asp Asp
    1025                1030

<210> SEQ ID NO 2
<211> LENGTH: 798
<212> TYPE: PRT
<213> ORGANISM: Homo sapiens

<400> SEQUENCE: 2

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile His
            100                 105                 110

Gln Ile Gln Pro Gln Gln Leu Val Leu Arg Leu Arg Ser Gly Glu Pro

-continued

```
            115                 120                 125
Gln Thr Phe Thr Leu Lys Phe Lys Arg Ala Glu Asp Tyr Pro Ile Asp
    130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
                165                 170                 175
Thr Ser Asp Phe Arg Ile Gly Phe Gly Ser Phe Val Glu Lys Thr Val
                180                 185                 190
Met Pro Tyr Ile Ser Thr Thr Pro Ala Lys Leu Arg Asn Pro Cys Thr
            195                 200                 205
Ser Glu Gln Asn Cys Thr Thr Pro Phe Ser Tyr Lys Asn Val Leu Ser
    210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Gly Phe Asp Ala Ile Met
                245                 250                 255
Gln Val Ala Val Cys Gly Ser Leu Ile Gly Trp Arg Asn Val Thr Arg
            260                 265                 270
Leu Leu Val Phe Ser Thr Asp Ala Gly Phe His Phe Ala Gly Asp Gly
    275                 280                 285
Lys Leu Gly Gly Ile Val Leu Pro Asn Asp Gly Gln Cys His Leu Glu
    290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
                325                 330                 335
Val Thr Glu Glu Phe Gln Pro Val Tyr Lys Glu Leu Lys Asn Leu Ile
                340                 345                 350
Pro Lys Ser Ala Val Gly Thr Leu Ser Ala Asn Ser Ser Asn Val Ile
            355                 360                 365
Gln Leu Ile Ile Asp Ala Tyr Asn Ser Leu Ser Ser Glu Val Ile Leu
    370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
                420                 425                 430
Asn Lys Cys Pro Lys Lys Asp Ser Asp Ser Phe Lys Ile Arg Pro Leu
            435                 440                 445
Gly Phe Thr Glu Glu Val Glu Val Ile Leu Gln Tyr Ile Cys Glu Cys
    450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
                500                 505                 510
Asp Ala Tyr Cys Arg Lys Glu Asn Ser Ser Glu Ile Cys Ser Asn Asn
            515                 520                 525
Gly Glu Cys Val Cys Gly Gln Cys Val Cys Arg Lys Arg Asp Asn Thr
    530                 535                 540
```

```
Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
            610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
            675                 680                 685

Ser His Cys Lys Glu Lys Asp Val Asp Asp Cys Trp Phe Tyr Phe Thr
            690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
            755                 760                 765

Glu Lys Met Asn Ala Lys Trp Asp Thr Gly Glu Asn Pro Ile Tyr Lys
770                 775                 780

Ser Ala Val Thr Thr Val Val Asn Pro Lys Tyr Glu Gly Lys
785                 790                 795

<210> SEQ ID NO 3
<211> LENGTH: 739
<212> TYPE: PRT
<213> ORGANISM: Homo sapiens

<400> SEQUENCE: 3

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
```

-continued

```
                    115                 120                 125
Ala Gly Lys Pro Ile Thr Val Lys Cys Ser Val Ala Asp Val Tyr Pro
        130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540
```

```
Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 4
<211> LENGTH: 2386
<212> TYPE: PRT
<213> ORGANISM: Homo sapiens

<400> SEQUENCE: 4

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175
```

```
Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
            195                 200                 205

Met Met Val Asp Cys Thr Cys Leu Gly Glu Gly Ser Gly Arg Ile Thr
            210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
            290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
            370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
            450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
            580                 585                 590
```

```
Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
        610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Gly Asp Glu Pro Gln Tyr Leu Asp Leu
        755                 760                 765

Pro Ser Thr Ala Thr Ser Val Asn Ile Pro Asp Leu Leu Pro Gly Arg
        770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
        850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro  Thr Asn Leu Gln Phe Val Asn Glu
        995                 1000                1005

Thr Asp Ser Thr Val Leu Val Arg Trp Thr Pro Pro  Arg Ala Gln
```

-continued

```
              1010                1015                1020
Ile  Thr  Gly  Tyr  Arg  Leu  Thr  Val  Gly  Leu  Thr  Arg  Arg  Gly  Gln
     1025                1030                1035

Pro  Arg  Gln  Tyr  Asn  Val  Gly  Pro  Ser  Val  Ser  Lys  Tyr  Pro  Leu
     1040                1045                1050

Arg  Asn  Leu  Gln  Pro  Ala  Ser  Glu  Tyr  Thr  Val  Ser  Leu  Val  Ala
     1055                1060                1065

Ile  Lys  Gly  Asn  Gln  Glu  Ser  Pro  Lys  Ala  Thr  Gly  Val  Phe  Thr
     1070                1075                1080

Thr  Leu  Gln  Pro  Gly  Ser  Ser  Ile  Pro  Pro  Tyr  Asn  Thr  Glu  Val
     1085                1090                1095

Thr  Glu  Thr  Thr  Ile  Val  Ile  Thr  Trp  Thr  Pro  Ala  Pro  Arg  Ile
     1100                1105                1110

Gly  Phe  Lys  Leu  Gly  Val  Arg  Pro  Ser  Gln  Gly  Gly  Glu  Ala  Pro
     1115                1120                1125

Arg  Glu  Val  Thr  Ser  Asp  Ser  Gly  Ser  Ile  Val  Val  Ser  Gly  Leu
     1130                1135                1140

Thr  Pro  Gly  Val  Glu  Tyr  Val  Tyr  Thr  Ile  Gln  Val  Leu  Arg  Asp
     1145                1150                1155

Gly  Gln  Glu  Arg  Asp  Ala  Pro  Ile  Val  Asn  Lys  Val  Val  Thr  Pro
     1160                1165                1170

Leu  Ser  Pro  Pro  Thr  Asn  Leu  His  Leu  Glu  Ala  Asn  Pro  Asp  Thr
     1175                1180                1185

Gly  Val  Leu  Thr  Val  Ser  Trp  Glu  Arg  Ser  Thr  Thr  Pro  Asp  Ile
     1190                1195                1200

Thr  Gly  Tyr  Arg  Ile  Thr  Thr  Thr  Pro  Thr  Asn  Gly  Gln  Gln  Gly
     1205                1210                1215

Asn  Ser  Leu  Glu  Glu  Val  Val  His  Ala  Asp  Gln  Ser  Ser  Cys  Thr
     1220                1225                1230

Phe  Asp  Asn  Leu  Ser  Pro  Gly  Leu  Glu  Tyr  Asn  Val  Ser  Val  Tyr
     1235                1240                1245

Thr  Val  Lys  Asp  Asp  Lys  Glu  Ser  Val  Pro  Ile  Ser  Asp  Thr  Ile
     1250                1255                1260

Ile  Pro  Ala  Val  Pro  Pro  Thr  Asp  Leu  Arg  Phe  Thr  Asn  Ile
     1265                1270                1275

Gly  Pro  Asp  Thr  Met  Arg  Val  Thr  Trp  Ala  Pro  Pro  Pro  Ser  Ile
     1280                1285                1290

Asp  Leu  Thr  Asn  Phe  Leu  Val  Arg  Tyr  Ser  Pro  Val  Lys  Asn  Glu
     1295                1300                1305

Glu  Asp  Val  Ala  Glu  Leu  Ser  Ile  Ser  Pro  Ser  Asp  Asn  Ala  Val
     1310                1315                1320

Val  Leu  Thr  Asn  Leu  Leu  Pro  Gly  Thr  Glu  Tyr  Val  Val  Ser  Val
     1325                1330                1335

Ser  Ser  Val  Tyr  Glu  Gln  His  Glu  Ser  Thr  Pro  Leu  Arg  Gly  Arg
     1340                1345                1350

Gln  Lys  Thr  Gly  Leu  Asp  Ser  Pro  Thr  Gly  Ile  Asp  Phe  Ser  Asp
     1355                1360                1365

Ile  Thr  Ala  Asn  Ser  Phe  Thr  Val  His  Trp  Ile  Ala  Pro  Arg  Ala
     1370                1375                1380

Thr  Ile  Thr  Gly  Tyr  Arg  Ile  Arg  His  His  Pro  Glu  His  Phe  Ser
     1385                1390                1395

Gly  Arg  Pro  Arg  Glu  Asp  Arg  Val  Pro  His  Ser  Arg  Asn  Ser  Ile
     1400                1405                1410
```

-continued

```
Thr Leu Thr Asn Leu Thr Pro Gly Thr Glu Tyr Val Val Ser Ile
    1415                1420                1425
Val Ala Leu Asn Gly Arg Glu Glu Ser Pro Leu Leu Ile Gly Gln
    1430                1435                1440
Gln Ser Thr Val Ser Asp Val Pro Arg Asp Leu Glu Val Val Ala
    1445                1450                1455
Ala Thr Pro Thr Ser Leu Leu Ile Ser Trp Asp Ala Pro Ala Val
    1460                1465                1470
Thr Val Arg Tyr Tyr Arg Ile Thr Tyr Gly Glu Thr Gly Gly Asn
    1475                1480                1485
Ser Pro Val Gln Glu Phe Thr Val Pro Gly Ser Lys Ser Thr Ala
    1490                1495                1500
Thr Ile Ser Gly Leu Lys Pro Gly Val Asp Tyr Thr Ile Thr Val
    1505                1510                1515
Tyr Ala Val Thr Gly Arg Gly Asp Ser Pro Ala Ser Ser Lys Pro
    1520                1525                1530
Ile Ser Ile Asn Tyr Arg Thr Glu Ile Asp Lys Pro Ser Gln Met
    1535                1540                1545
Gln Val Thr Asp Val Gln Asp Asn Ser Ile Ser Val Lys Trp Leu
    1550                1555                1560
Pro Ser Ser Ser Pro Val Thr Gly Tyr Arg Val Thr Thr Thr Pro
    1565                1570                1575
Lys Asn Gly Pro Gly Pro Thr Lys Thr Lys Thr Ala Gly Pro Asp
    1580                1585                1590
Gln Thr Glu Met Thr Ile Glu Gly Leu Gln Pro Thr Val Glu Tyr
    1595                1600                1605
Val Val Ser Val Tyr Ala Gln Asn Pro Ser Gly Glu Ser Gln Pro
    1610                1615                1620
Leu Val Gln Thr Ala Val Thr Asn Ile Asp Arg Pro Lys Gly Leu
    1625                1630                1635
Ala Phe Thr Asp Val Asp Val Asp Ser Ile Lys Ile Ala Trp Glu
    1640                1645                1650
Ser Pro Gln Gly Gln Val Ser Arg Tyr Arg Val Thr Tyr Ser Ser
    1655                1660                1665
Pro Glu Asp Gly Ile His Glu Leu Phe Pro Ala Pro Asp Gly Glu
    1670                1675                1680
Glu Asp Thr Ala Glu Leu Gln Gly Leu Arg Pro Gly Ser Glu Tyr
    1685                1690                1695
Thr Val Ser Val Val Ala Leu His Asp Asp Met Glu Ser Gln Pro
    1700                1705                1710
Leu Ile Gly Thr Gln Ser Thr Ala Ile Pro Ala Pro Thr Asp Leu
    1715                1720                1725
Lys Phe Thr Gln Val Thr Pro Thr Ser Leu Ser Ala Gln Trp Thr
    1730                1735                1740
Pro Pro Asn Val Gln Leu Thr Gly Tyr Arg Val Arg Val Thr Pro
    1745                1750                1755
Lys Glu Lys Thr Gly Pro Met Lys Glu Ile Asn Leu Ala Pro Asp
    1760                1765                1770
Ser Ser Ser Val Val Val Ser Gly Leu Met Val Ala Thr Lys Tyr
    1775                1780                1785
Glu Val Ser Val Tyr Ala Leu Lys Asp Thr Leu Thr Ser Arg Pro
    1790                1795                1800
```

-continued

```
Ala Gln Gly Val Val Thr Thr Leu Glu Asn Val Ser Pro Pro Arg
1805                1810                1815

Arg Ala Arg Val Thr Asp Ala Thr Glu Thr Thr Ile Thr Ile Ser
1820                1825                1830

Trp Arg Thr Lys Thr Glu Thr Ile Thr Gly Phe Gln Val Asp Ala
1835                1840                1845

Val Pro Ala Asn Gly Gln Thr Pro Ile Gln Arg Thr Ile Lys Pro
1850                1855                1860

Asp Val Arg Ser Tyr Thr Ile Thr Gly Leu Gln Pro Gly Thr Asp
1865                1870                1875

Tyr Lys Ile Tyr Leu Tyr Thr Leu Asn Asp Asn Ala Arg Ser Ser
1880                1885                1890

Pro Val Val Ile Asp Ala Ser Thr Ala Ile Asp Ala Pro Ser Asn
1895                1900                1905

Leu Arg Phe Leu Ala Thr Thr Pro Asn Ser Leu Leu Val Ser Trp
1910                1915                1920

Gln Pro Pro Arg Ala Arg Ile Thr Gly Tyr Ile Ile Lys Tyr Glu
1925                1930                1935

Lys Pro Gly Ser Pro Pro Arg Glu Val Val Pro Arg Pro Arg Pro
1940                1945                1950

Gly Val Thr Glu Ala Thr Ile Thr Gly Leu Glu Pro Gly Thr Glu
1955                1960                1965

Tyr Thr Ile Tyr Val Ile Ala Leu Lys Asn Asn Gln Lys Ser Glu
1970                1975                1980

Pro Leu Ile Gly Arg Lys Lys Thr Asp Glu Leu Pro Gln Leu Val
1985                1990                1995

Thr Leu Pro His Pro Asn Leu His Gly Pro Glu Ile Leu Asp Val
2000                2005                2010

Pro Ser Thr Val Gln Lys Thr Pro Phe Val Thr His Pro Gly Tyr
2015                2020                2025

Asp Thr Gly Asn Gly Ile Gln Leu Pro Gly Thr Ser Gly Gln Gln
2030                2035                2040

Pro Ser Val Gly Gln Gln Met Ile Phe Glu Glu His Gly Phe Arg
2045                2050                2055

Arg Thr Thr Pro Pro Thr Thr Ala Thr Pro Ile Arg His Arg Pro
2060                2065                2070

Arg Pro Tyr Pro Pro Asn Val Gly Glu Glu Ile Gln Ile Gly His
2075                2080                2085

Ile Pro Arg Glu Asp Val Asp Tyr His Leu Tyr Pro His Gly Pro
2090                2095                2100

Gly Leu Asn Pro Asn Ala Ser Thr Gly Gln Glu Ala Leu Ser Gln
2105                2110                2115

Thr Thr Ile Ser Trp Ala Pro Phe Gln Asp Thr Ser Glu Tyr Ile
2120                2125                2130

Ile Ser Cys His Pro Val Gly Thr Asp Glu Glu Pro Leu Gln Phe
2135                2140                2145

Arg Val Pro Gly Thr Ser Thr Ser Ala Thr Leu Thr Gly Leu Thr
2150                2155                2160

Arg Gly Ala Thr Tyr Asn Ile Ile Val Glu Ala Leu Lys Asp Gln
2165                2170                2175

Gln Arg His Lys Val Arg Glu Glu Val Val Thr Val Gly Asn Ser
2180                2185                2190

Val Asn Glu Gly Leu Asn Gln Pro Thr Asp Asp Ser Cys Phe Asp
```

-continued

|  |  |  | 2195 |  |  |  | 2200 |  |  |  | 2205 |  |
|---|---|---|---|---|---|---|---|---|---|---|---|---|
| Pro | Tyr | Thr | Val | Ser | His | Tyr | Ala | Val | Gly | Asp | Glu | Trp | Glu | Arg |
|  | 2210 |  |  |  |  | 2215 |  |  |  |  | 2220 |  |

| Met | Ser | Glu | Ser | Gly | Phe | Lys | Leu | Leu | Cys | Gln | Cys | Leu | Gly | Phe |
|---|---|---|---|---|---|---|---|---|---|---|---|---|---|---|
| 2225 |  |  |  |  | 2230 |  |  |  |  | 2235 |  |  |  |  |

| Gly | Ser | Gly | His | Phe | Arg | Cys | Asp | Ser | Ser | Arg | Trp | Cys | His | Asp |
|---|---|---|---|---|---|---|---|---|---|---|---|---|---|---|
|  | 2240 |  |  |  |  | 2245 |  |  |  |  | 2250 |  |  |  |

| Asn | Gly | Val | Asn | Tyr | Lys | Ile | Gly | Glu | Lys | Trp | Asp | Arg | Gln | Gly |
|---|---|---|---|---|---|---|---|---|---|---|---|---|---|---|
| 2255 |  |  |  |  | 2260 |  |  |  |  | 2265 |  |  |  |  |

| Glu | Asn | Gly | Gln | Met | Met | Ser | Cys | Thr | Cys | Leu | Gly | Asn | Gly | Lys |
|---|---|---|---|---|---|---|---|---|---|---|---|---|---|---|
|  | 2270 |  |  |  |  | 2275 |  |  |  |  | 2280 |  |  |  |

| Gly | Glu | Phe | Lys | Cys | Asp | Pro | His | Glu | Ala | Thr | Cys | Tyr | Asp | Asp |
|---|---|---|---|---|---|---|---|---|---|---|---|---|---|---|
| 2285 |  |  |  |  | 2290 |  |  |  |  | 2295 |  |  |  |  |

| Gly | Lys | Thr | Tyr | His | Val | Gly | Glu | Gln | Trp | Gln | Lys | Glu | Tyr | Leu |
|---|---|---|---|---|---|---|---|---|---|---|---|---|---|---|
|  | 2300 |  |  |  |  | 2305 |  |  |  |  | 2310 |  |  |  |

| Gly | Ala | Ile | Cys | Ser | Cys | Thr | Cys | Phe | Gly | Gly | Gln | Arg | Gly | Trp |
|---|---|---|---|---|---|---|---|---|---|---|---|---|---|---|
| 2315 |  |  |  |  | 2320 |  |  |  |  | 2325 |  |  |  |  |

| Arg | Cys | Asp | Asn | Cys | Arg | Arg | Pro | Gly | Gly | Glu | Pro | Ser | Pro | Glu |
|---|---|---|---|---|---|---|---|---|---|---|---|---|---|---|
|  | 2330 |  |  |  |  | 2335 |  |  |  |  | 2340 |  |  |  |

| Gly | Thr | Thr | Gly | Gln | Ser | Tyr | Asn | Gln | Tyr | Ser | Gln | Arg | Tyr | His |
|---|---|---|---|---|---|---|---|---|---|---|---|---|---|---|
| 2345 |  |  |  |  | 2350 |  |  |  |  | 2355 |  |  |  |  |

| Gln | Arg | Thr | Asn | Thr | Asn | Val | Asn | Cys | Pro | Ile | Glu | Cys | Phe | Met |
|---|---|---|---|---|---|---|---|---|---|---|---|---|---|---|
|  | 2360 |  |  |  |  | 2365 |  |  |  |  | 2370 |  |  |  |

| Pro | Leu | Asp | Val | Gln | Ala | Asp | Arg | Glu | Asp | Ser | Arg | Glu |
|---|---|---|---|---|---|---|---|---|---|---|---|---|
| 2375 |  |  |  |  | 2380 |  |  |  |  | 2385 |  |  |

<210> SEQ ID NO 5
<211> LENGTH: 3562
<212> TYPE: DNA
<213> ORGANISM: Homo sapiens

<400> SEQUENCE: 5

```
gccatcccgc gctctgcggg ctgggaggcc cgggccagga cgcgagtcct gcgcagccga      60
ggttccccag cgcccctgc agccgcgcgt aggcagagac ggagcccggc cctgcgcctc     120
cgcaccacgc ccgggacccc acccagcggc ccgtacccgg agaagcagcg cgagcacccg     180
aagctcccgg ctggcggcag aaaccgggag tggggccggg cgagtgcgcg gcatcccagg     240
ccggcccgaa cgctccgccc gcggtgggcc gacttcccct cctcttccct ctctccttcc     300
tttagcccgc tggcgccgga cacgctgcgc ctcatctctt ggggcgttct tccccgttgg     360
ccaaccgtcg catccgtgc aactttgggg tagtggccgt ttagtgttga atgttcccca     420
ccgagagcgc atggcttggg aagcgaggcg cgaacccggc ccccgaaggg ccgccgtccg     480
ggagacggtg atgctgttgc tgtgcctggg ggtcccgacc ggccgcccct acaacgtgga     540
cactgagagc gcgctgcttt accagggccc cacaacacg ctgttcggct actcggtcgt     600
gctgcacagc cacggggcga accgatggct cctagtgggt gcgcccactg ccaactggct     660
cgccaacgct tcagtgatca atcccggggc gatttacaga tgcaggatcg aaagaatcc     720
cggccagacg tgcgaacagc tccagctggg tagccctaat ggagaacctt gtggaaagac     780
ttgtttggaa gagagagaca atcagtggt gggggtcaca ctttccagac agccaggaga     840
aaatggatcc atcgtgactt gtgggcatag atggaaaaat atattttaca taagaatga     900
aaataagctc cccactggtg gttgctatgg agtgccccct gatttacgaa cagaactgag     960
taaaagaata gctccgtgtt atcaagatta tgtgaaaaaa tttggagaaa atttttgcatc    1020
```

```
atgtcaagct ggaatatcca gttttacac aaaggattta attgtgatgg gggccccagg   1080
atcatcttac tggactggct ctcttttgt ctacaatata actacaaata aatacaaggc   1140
ttttttagac aaacaaaatc aagtaaaatt tggaagttat ttaggatatt cagtcggagc   1200
tggtcatttt cggagccagc atactaccga agtagtcgga ggagctcctc aacatgagca   1260
gattggtaag gcatatatat tcagcattga tgaaaagaa ctaaatatct tacatgaaat   1320
gaaaggtaaa aagcttggat cgtactttgg agcttctgtc tgtgctgtgg acctcaatgc   1380
agatggcttc tcagatctgc tcgtgggagc acccatgcag agcaccatca gagaggaagg   1440
aagagtgttt gtgtacatca actctggctc gggagcagta atgaatgcaa tggaaacaaa   1500
cctcgttgga agtgacaaat atgctgcaag atttggggaa tctatagtta atcttggcga   1560
cattgacaat gatggctttg aagatgttgc tatcggagct ccacaagaag atgacttgca   1620
aggtgctatt tatatttaca atggccgtgc agatgggatc tcgtcaacct tctcacagag   1680
aattgaagga cttcagatca gcaaatcgtt aagtatgttt ggacagtcta tatcaggaca   1740
aattgatgca gataataatg ctatgtaga tgtagcagtt ggtgcttttc ggtctgattc   1800
tgctgtcttg ctaaggacaa gacctgtagt aattgttgac gcttctttaa gccaccctga   1860
gtcagtaaat agaacgaaat ttgactgtgt tgaaaatgga tggccttctg tgtgcataga   1920
tctaacactt tgtttctcat ataagggcaa ggaagttcca ggttacattg ttttgtttta   1980
taacatgagt ttggatgtga acagaaaggc agagtctcca ccaagattct atttctcttc   2040
taatggaact tctgacgtga ttacaggaag catacaggtg tccagcagag aagctaactg   2100
tagaacacat caagcattta tgcggaaaga tgtgcgggac atcctcaccc caattcagat   2160
tgaagctgct taccaccttg gtcctcatgt catcagtaaa cgaagtacag aggaattccc   2220
accacttcag ccaattcttc agcagaagaa agaaaaagac ataatgaaaa aaacaataaa   2280
ctttgcaagg ttttgtgccc atgaaaattg ttctgctgat ttacaggttt ctgcaaagat   2340 tgggttttg aagccccatg aaaataaaac atatcttgct gttgggagta tgaagacatt   2400
gatgttgaat gtgtccttgt ttaatgctgg agatgatgca tatgaaacga ctctacatgt   2460
caaactaccc gtgggtcttt atttcattaa gatttagag ctggaagaga agcaaataaa   2520
ctgtgaagtc acagataact ctggcgtggt acaacttgac tgcagtattg gctatatata   2580
tgtagatcat ctctcaagga tagatattag ctttctcctg gatgtgagct cactcagcag   2640
agcggaagag gacctcagta tcacagtgca tgctacctgt gaaaatgaag aggaaatgga   2700
caatctaaag cacagcagag tgactgtagc aatacctta aaatatgagg ttaagctgac   2760
tgttcatggg tttgtaaacc caacttcatt tgtgtatgga tcaaatgatg aaaatgagcc   2820
tgaaacgtgc atggtggaga aaatgaactt aactttccat gttatcaaca ctggcaatag   2880
tatggctccc aatgttagtg tggaaataat ggtaccaaat tcttttagcc cccaaactga   2940
taagctgttc aacatttggg atgtccagac tactactgga gaatgccact ttgaaaatta   3000
tcaaagagtg tgtgcattag agcagcaaaa gagtgcaatg cagaccttga aaggcatagt   3060
ccggttcttg tccaagactg ataagaggct attgtactgc ataaaagctg atccacattg   3120
tttaaatttc ttgtgtaatt ttgggaaaat ggaaagtgga aagaagcca gtgttcatat   3180 ccaactggaa ggccggccat ccattttaga aatggatgag acttcagcac tcaagtttga   3240
aataagagca acaggttttc cagagccaaa tccaagagta attgaactaa acaaggatga   3300
gaatgttgcg catgttctac tggaaggact acatcatcaa agacccaaac gttatttcac   3360
```

```
catagtgatt atttcaagta gcttgctact tggacttatt gtacttctat tgatctcata    3420
tgttatgtgg aaggctggct tctttaaaag acaatacaaa tctatcctac aagaagaaaa    3480
cagaagagac agttggagtt atatcaacag taaaagcaat gatgattaag gacttctttc    3540
aaattgagag aatggaaaac ag                                             3562

<210> SEQ ID NO 6
<211> LENGTH: 3562
<212> TYPE: DNA
<213> ORGANISM: Homo sapiens

<400> SEQUENCE: 6
gccatcccgc gctctgcggg ctgggaggcc cgggccagga cgcgagtcct gcgcagccga      60
ggttccccag cgcccctgc agccgcgcgt aggcagagac ggagcccggc cctgcgcctc     120
cgcaccacgc ccgggacccc acccagcggc ccgtacccgg agaagcagcg cgagcacccg     180
aagctcccgg ctggcggcag aaaccgggag tggggccggg cgagtgcgcg gcatcccagg     240
ccggcccgaa cgctccgccc gcggtgggcc gacttcccct cctcttccct ctctccttcc     300
tttagcccgc tggcgccgga cacgctgcgc ctcatctctt gggcgttct tccccgttgg      360 ccaaccgtcg catcccgtgc aactttgggg tagtggccgt ttagtgttga atgttcccca     420
ccgagagcgc atggcttggg aagcgaggcg cgaacccggc ccccgaaggg ccgccgtccg     480
ggagacggtg atgctgttgc tgtgcctggg ggtcccgacc ggccgcccct acaacgtgga     540
cactgagagc gcgctgcttt accagggccc ccacaacacg ctgttcggct actcggtcgt     600
gctgcacagc cacggggcga accgatggct cctagtgggt gcgcccactg ccaactggct     660
cgccaacgct tcagtgatca atcccggggc gatttacaga tgcaggatcg gaaagaatcc     720
cggccagacg tgcgaacagc tccagctggg tagccctaat ggagaacctt gtggaaagac     780
ttgtttggaa gagagagaca atcagtggtt gggggtcaca cttttccgag agccaggaga     840
aaatggatcc atcgtgactt gtgggcatag atggaaaaat atattttaca taagaatga      900 aaataagctc cccactggtg gttgctatgg agtgccccct gatttacgaa cagaactgag     960
taaaagaata gctccgtgtt atcaagatta tgtgaaaaaa tttggagaaa attttgcatc    1020
atgtcaagct ggaatatcca gttttttacac aaaggattta attgtgatgg ggccccagg    1080 atcatcttac tggactggct ctcttttttgt ctacaatata actacaaata aatacaaggc    1140
ttttttagac aaacaaaatc aagtaaaatt tggaagttat ttaggatatt cagtcggagc    1200
tggtcatttt cggagccagc atactaccga agtagtcgga ggagctcctc aacatgagca    1260
gattggtaag gcatatatat tcagcattga tgaaaaagaa ctaaatatct tacatgaaat    1320
gaaaggtaaa aagcttggat cgtactttgg agcttctgtc tgtgctgtgg acctcaatgc    1380
agatggcttc tcagatctgc tcgtgggagc acccatgcag agcaccatca gagaggaagg    1440
aagagtgttt gtgtacatca actctggctc gggagcagta atgaatgcaa tggaaacaaa    1500
cctcgttgga agtgacaaat atgctgcaag atttggggaa tctatagtta atcttggcga    1560
cattgacaat gatggctttg aagatgttgc tatcggagct ccacaagaag atgacttgca    1620
aggtgctatt tatatttaca atggccgtgc agatgggatc tcgtcaacct tctcacagag    1680
aattgaagga cttcagatca gcaaatcgtt aagtatgttt ggacagtcta tcaggaca     1740 aattgatgca gataataatg ctatgtaga tgtagcagtt ggtgcttttc ggtctgattc    1800
tgctgtcttg ctaaggacaa gacctgtagt aattgttgac gcttcttaa gccaccctga    1860 gtcagtaaat agaacgaaat ttgactgtgt tgaaaatgga tggccttctg tgtgcataga    1920
```

-continued

```
tctaacactt tgtttctcat ataagggcaa ggaagttcca ggttacattg ttttgtttta    1980
taacatgagt ttggatgtga acagaaaggc agagtctcca ccaagattct atttctcttc    2040
taatggaact tctgacgtga ttacaggaag catacaggtg tccagcagag aagctaactg    2100
tagaacacat caagcattta tgcggaaaga tgtgcgggac atcctcaccc caattcagat    2160
tgaagctgct taccaccttg gtcctcatgt catcagtaaa cgaagtacag aggaattccc    2220
accacttcag ccaattcttc agcagaagaa agaaaaagac ataatgaaaa aacaataaa     2280 ctttgcaagg ttttgtgccc atgaaaattg ttctgctgat ttacaggttt ctgcaaagat    2340 tgggttttg  aagccccatg aaaataaaac atatcttgct gttgggagta tgaagacatt    2400
gatgttgaat gtgtccttgt ttaatgctgg agatgatgca tatgaaacga ctctacatgt    2460
caaactaccc gtgggtcttt atttcattaa gattttagag ctggaagaga agcaaataaa    2520
ctgtgaagtc acagataact ctggcgtggt acaacttgac tgcagtattg gctatatata    2580
tgtagatcat ctctcaagga tagatattag ctttctcctg gatgtgagct cactcagcag    2640
agcggaagag gacctcagta tcacagtgca tgctacctgt gaaaatgaag aggaaatgga    2700
caatctaaag cacagcagag tgactgtagc aataccttta aaatatgagg ttaagctgac    2760
tgttcatggg tttgtaaacc caacttcatt tgtgtatgga tcaaatgatg aaaatgagcc    2820
tgaaacgtgc atggtggaga aaatgaactt aactttccat gttatcaaca ctggcaatag    2880
tatggctccc aatgttagtg tggaaataat ggtaccaaat tcttttagcc cccaaactga    2940
taagctgttc aacattttgg atgtccagac tactactgga gaatgccact ttgaaaatta    3000
tcaaagagtg tgtgcattag agcagcaaaa gagtgcaatg cagaccttga aaggcatagt    3060
ccggttcttg tccaagactg ataagaggct attgtactgc ataaaagctg atccacattg    3120
tttaaatttc ttgtgtaatt ttgggaaaat ggaaagtgga aaagaagcca gtgttcatat    3180
ccaactggaa ggccggccat ccatttttaga aatggatgag acttcagcac tcaagtttga    3240
aataagagca acaggttttc cagagccaaa tccaagagta attgaactaa caaggatga    3300 gaatgttgcg catgttctac tggaaggact acatcatcaa agacccaaac gttatttcac    3360
catagtgatt atttcaagta gcttgctact tggacttatt gtacttctat tgatctcata    3420
tgttatgtgg aaggctggct tctttaaaag acaatacaaa tctatcctac aagaagaaa     3480 cagaagagac agttggagtt atatcaacag taaaagcaat gatgattaag gacttcttc     3540 aaattgagag aatggaaaac ag                                             3562
```

<210> SEQ ID NO 7
<211> LENGTH: 3614
<212> TYPE: DNA
<213> ORGANISM: Homo sapiens

<400> SEQUENCE: 7

```
gtccgccaaa acctgcgcgg ataggggaaga acagcacccc ggcgccgatt gccgtaccaa      60
acaagcctaa cgtccgctgg gccccggacg ccgcgcggaa aagatgaatt tacaaccaat     120
tttctggatt ggactgatca gttcagtttg ctgtgtgttt gctcaaacag atgaaaatag     180
atgtttaaaa gcaaatgcca atcatgtgg  agaatgtata caagcagggc caaattgtgg     240
gtggtgcaca aattcaacat ttttacagga aggaatgcct acttctgcac gatgtgatga     300
tttagaagcc ttaaaaaaga agggttgccc tccagatgac atagaaaatc ccagaggctc     360
caaagatata aagaaaaata aaaatgtaac caaccgtagc aaaggaacag cagagaagct     420
```

```
caagccagag gatattcatc agatccaacc acagcagttg gttttgcgat taagatcagg    480
ggagccacag acatttacat taaaattcaa gagagctgaa gactatccca ttgacctcta    540
ctaccttatg gacctgtctt attcaatgaa agacgatttg gagaatgtaa aaagtcttgg    600
aacagatctg atgaatgaaa tgaggaggat tacttcggac ttcagaattg gatttggctc    660
atttgtggaa aagactgtga tgccttacat tagcacaaca ccagctaagc tcaggaaccc    720
ttgcacaagt gaacagaact gcaccacccc atttagctac aaaaatgtgc tcagtcttac    780
taataaagga gaagtattta atgaacttgt tggaaaacag cgcatatctg gaaatttgga    840
ttctccagaa ggtggtttcg atgccatcat gcaagttgca gtttgtggat cactgattgg    900
ctggaggaat gttacacggc tgctggtgtt ttccacagat gccgggtttc actttgctgg    960
agatgggaaa cttggtggca ttgttttacc aaatgatgga caatgtcacc tggaaaataa   1020
tatgtacaca atgagccatt attatgatta tccttctatt gctcaccttg tccagaaact   1080
gagtgaaaat aatattcaga caatttttgc agttactgaa gaatttcagc ctgtttacaa   1140
ggagctgaaa aacttgatcc ctaagtcagc agtaggaaca ttatctgcaa attctagcaa   1200
tgtaattcag ttgatcattg atgcatacaa ttccctttcc tcagaagtca ttttggaaaa   1260
cggcaaattg tcagaaggag taacaataag ttacaaatct tactgcaaga acggggtgaa   1320
tggaacaggg gaaaatggaa gaaaatgttc caatatttcc attggagatg aggttcaatt   1380
tgaaattagc ataacttcaa ataagtgtcc aaaaaaggat tctgacagct ttaaaattag   1440
gcctctgggc tttacggagg aagtagaggt tattcttcag tacatctgtg aatgtgaatg   1500
ccaaagcgaa ggcatccctg aaagtcccaa gtgtcatgaa ggaaatggga catttgagtg   1560
tggcgcgtgc aggtgcaatg aagggcgtgt tggtagacat tgtgaatgca gcacagatga   1620
agttaacagt gaagacatgg atgcttactg caggaaagaa aacagttcag aaatctgcag   1680
taacaatgga gagtgcgtct gcggacagtg tgtttgtagg aagagggata atacaaatga   1740
aatttattct ggcaaattct gcgagtgtga taatttcaac tgtgatagat ccaatggctt   1800
aatttgtgga ggaaatggtg tttgcaagtg tcgtgtgtgt gagtgcaacc ccaactacac   1860
tggcagtgca tgtgactgtt ctttggatac tagtacttgt gaagccagca acggacagat   1920
ctgcaatggc cggggcatct gcgagtgtgg tgtctgtaag tgtacagatc cgaagtttca   1980
agggcaaacg tgtgagatgt gtcagacctg ccttggtgtc tgtgctgagc ataaagaatg   2040
tgttcagtgc agagccttca ataaaggaga aagaaaagac acatgcacac aggaatgttc   2100
ctattttaac attaccaagg tagaaagtcg ggacaaatta ccccagccgg tccaacctga   2160
tcctgtgtcc cattgtaagg agaaggatgt tgacgactgt tggttctatt ttacgtattc   2220
agtgaatggg aacaacgagg tcatggttca tgttgtggaa aatccagagt gtcccactgg   2280
tccagacatc attccaattg tagctggtgt ggttgctgga attgttctta ttggccttgc   2340
attactgctg atatggaagc ttttaatgat aattcatgac agaagggagt ttgctaaatt   2400
tgaaaaggag aaaatgaatg ccaaatggga cacgggtgaa aatcctattt ataagagtgc   2460
cgtaacaact gtggtcaatc cgaagtatga gggaaaatga gtactgcccg tgcaaatccc   2520
acaacactga atgcaaagta gcaatttcca tagtcacagt taggtagctt tagggcaata   2580
ttgccatggt tttactcatg tgcaggtttt gaaaatgtac aatatgtata attttttaaaa   2640
tgttttatta ttttgaaaat aatgttgtaa ttcatgccag ggactgacaa aagacttgag   2700
acaggatggt tattccttgtc agctaaggtc acattgtgcc tttttgacct tttcttcctg   2760
gactattgaa atcaagctta ttggattaag tgatatttct atagcgattg aaagggcaat   2820
```

| | |
|---|---|
| agttaaagta atgagcatga tgagagtttc tgttaatcat gtattaaaac tgattttag | 2880 |
| ctttacatat gtcagtttgc agttatgcag aatccaaagt aaatgtcctg ctagctagtt | 2940 |
| aaggattgtt ttaaatctgt tattttgcta tttgcctgtt agacatgact gatgacatat | 3000 |
| ctgaaagaca agtatgttga gagttgctgg tgtaaaatac gtttgaaata gttgatctac | 3060 |
| aaaggccatg ggaaaaattc agagagttag gaaggaaaaa ccaatagctt taaaacctgt | 3120 |
| gtgccatttt aagagttact taatgtttgg taacttttat gccttcactt tacaaattca | 3180 |
| agccttagat aaaagaaccg agcaattttc tgctaaaaag tccttgattt agcactattt | 3240 |
| acatacaggc catactttac aaagtatttg ctgaatgggg accttttgag ttgaatttat | 3300 |
| tttattattt ttattttgtt taatgtctgg tgctttctat cacctcttct aatcttttaa | 3360 |
| tgtatttgtt tgcaattttg gggtaagact tttttatgag tactttttct ttgaagtttt | 3420 |
| agcggtcaat ttgccttttt aatgaacatg tgaagttata ctgtggctat gcaacagctc | 3480 |
| tcacctacgc gagtcttact ttgagttagt gccataacag accactgtat gtttacttct | 3540 |
| caccatttga gttgcccatc ttgtttcaca ctagtcacat tcttgtttta agtgccttta | 3600 |
| gttttaacag ttca | 3614 |

<210> SEQ ID NO 8
<211> LENGTH: 2220
<212> TYPE: DNA
<213> ORGANISM: Homo sapiens

<400> SEQUENCE: 8

| | |
|---|---|
| atgcctggga agatggtcgt gatccttgga gcctcaaata ctctttggat aatgtttgca | 60 |
| gcttctcaag cttttaaaat cgagaccacc ccagaatcta gatatcttgc tcagattggt | 120 |
| gactccgtct cattgacttg cagcaccaca ggctgtgagt ccccatttt ctcttggaga | 180 |
| acccagatag atagtccact gaatgggaag gtgacgaatg aggggaccac atctacgctg | 240 |
| acaatgaatc ctgttagttt tgggaacgaa cactcttacc tgtgcacagc aacttgtgaa | 300 |
| tctaggaaat tggaaaaagg aatccaggtg gagatctact cttttcctaa ggatccagag | 360 |
| attcatttga gtggccctct ggaggctggg aagccgatca cagtcaagtg ttcagttgct | 420 |
| gatgtatacc catttgacag gctggagata gacttactga aaggagatca tctcatgaag | 480 |
| agtcaggaat ttctggagga tgcagacagg aagtccctgg aaaccaagag tttggaagta | 540 |
| acctttactc ctgtcattga ggatattgga aaagttcttg tttgccgagc taaattacac | 600 |
| attgatgaaa tggattctgt gcccacagta aggcaggctg taaaagaatt gcaagtctac | 660 |
| atatcaccca gaatacagt tatttctgtg aatccatcca caaagctgca agaaggtggc | 720 |
| tctgtgacca tgacctgttc cagcgagggt ctaccagctc cagagatttt ctggagtaag | 780 |
| aaattagata tgggaatct acagcaccct tctggaaatg caactctcac cttaattgct | 840 |
| atgaggatgg aagattctgg aatttatgtg tgtgaaggag ttaatttgat tgggaaaaac | 900 |
| agaaaagagg tggaattaat tgttcaagag aaaccattta ctgttgagat ctcccctgga | 960 |
| ccccggattg ctgctcagat tggagactca gtcatgttga catgtagtgt catgggctgt | 1020 |
| gaatccccat ctttctcctg gagaacccag atagacagcc ctctgagcgg aaaggtgagg | 1080 |
| agtgagggga ccaattccac gctgaccctg agccctgtga gttttgagaa cgaacactct | 1140 |
| tatctgtgca cagtgacttg tggacataag aaactggaaa agggaatcca ggtggagctc | 1200 |
| tactcattcc ctagagatcc agaaatcgag atgagtggtg gcctcgtgaa tgggagctct | 1260 |

-continued

```
gtcactgtaa gctgcaaggt tcctagcgtg taccccttg accggctgga gattgaatta      1320
cttaaggggg agactattct ggagaatata gagttttgg aggatacgga tatgaaatct      1380
ctagagaaca aaagtttgga aatgaccttc atccctacca ttgaagatac tggaaaagct     1440
cttgtttgtc aggctaagtt acatattgat gacatggaat cgaacccaa acaaaggcag     1500 agtacgcaaa cactttatgt caatgttgcc cccagagata caaccgtctt ggtcagccct    1560
tcctccatcc tggaggaagg cagttctgtg aatatgacat gcttgagcca gggctttcct    1620
gctccgaaaa tcctgtggag caggcagctc cctaacgggg agctacagcc tctttctgag    1680
aatgcaactc tcaccttaat ttctacaaaa atggaagatt ctggggttta tttatgtgaa    1740
ggaattaacc aggctggaag aagcagaaag gaagtggaat taattatcca agttactcca    1800
aaagacataa aacttacagc ttttccttct gagagtgtca agaaggaga cactgtcatc      1860 atctcttgta catgtggaaa tgttccagaa acatggataa tcctgaagaa aaaagcggag    1920
acaggagaca cagtactaaa atctatagat ggcgcctata ccatccgaaa ggcccagttg    1980
aaggatgcgg gagtatatga atgtgaatct aaaaacaaag ttggctcaca attaagaagt    2040
ttaacacttg atgttcaagg aagagaaaac aacaaagact attttctcc tgagcttctc     2100 gtgctctatt ttgcatcctc cttaataata cctgccattg gaatgataat ttactttgca    2160
agaaaagcca acatgaaggg gtcatatagt cttgtagaag cacagaaatc aaaagtgtag    2220
```

<210> SEQ ID NO 9
<211> LENGTH: 2386
<212> TYPE: PRT
<213> ORGANISM: Homo sapiens

<400> SEQUENCE: 9

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205
```

```
Met Met Val Asp Cys Thr Cys Leu Gly Glu Gly Ser Gly Arg Ile Thr
    210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
            260                 265                 270
His Thr Ser Val Gln Thr Thr Ser Ser Gly Ser Gly Pro Phe Thr Asp
        275                 280                 285
Val Arg Ala Ala Val Tyr Gln Pro Gln Pro His Pro Gln Pro Pro Pro
    290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Gln Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
```

```
                625             630             635             640
Tyr Ile Leu Arg Trp Arg Pro Lys Asn Ser Val Gly Arg Trp Lys Glu
                645             650             655
Ala Thr Ile Pro Gly His Leu Asn Ser Tyr Thr Ile Lys Gly Leu Lys
                660             665             670
Pro Gly Val Val Tyr Glu Gly Gln Leu Ile Ser Ile Gln Gln Tyr Gly
                675             680             685
His Gln Glu Val Thr Arg Phe Asp Phe Thr Thr Thr Ser Thr Ser Thr
                690             695             700
Pro Val Thr Ser Asn Thr Val Thr Gly Glu Thr Thr Pro Phe Ser Pro
705             710             715             720
Leu Val Ala Thr Ser Glu Ser Val Thr Glu Ile Thr Ala Ser Ser Phe
                725             730             735
Val Val Ser Trp Val Ser Ala Ser Asp Thr Val Ser Gly Phe Arg Val
                740             745             750
Glu Tyr Glu Leu Ser Glu Glu Gly Asp Glu Pro Gln Tyr Leu Asp Leu
                755             760             765
Pro Ser Thr Ala Thr Ser Val Asn Ile Pro Asp Leu Leu Pro Gly Arg
770             775             780
Lys Tyr Ile Val Asn Val Tyr Gln Ile Ser Glu Asp Gly Glu Gln Ser
785             790             795             800
Leu Ile Leu Ser Thr Ser Gln Thr Thr Ala Pro Asp Ala Pro Pro Asp
                805             810             815
Pro Thr Val Asp Gln Val Asp Asp Thr Ser Ile Val Val Arg Trp Ser
                820             825             830
Arg Pro Gln Ala Pro Ile Thr Gly Tyr Arg Ile Val Tyr Ser Pro Ser
                835             840             845
Val Glu Gly Ser Ser Thr Glu Leu Asn Leu Pro Glu Thr Ala Asn Ser
850             855             860
Val Thr Leu Ser Asp Leu Gln Pro Gly Val Gln Tyr Asn Ile Thr Ile
865             870             875             880
Tyr Ala Val Glu Glu Asn Gln Glu Ser Thr Pro Val Val Ile Gln Gln
                885             890             895
Glu Thr Thr Gly Thr Pro Arg Ser Asp Thr Val Pro Ser Pro Arg Asp
                900             905             910
Leu Gln Phe Val Glu Val Thr Asp Val Lys Val Thr Ile Met Trp Thr
                915             920             925
Pro Pro Glu Ser Ala Val Thr Gly Tyr Arg Val Asp Val Ile Pro Val
                930             935             940
Asn Leu Pro Gly Glu His Gly Gln Arg Leu Pro Ile Ser Arg Asn Thr
945             950             955             960
Phe Ala Glu Val Thr Gly Leu Ser Pro Gly Val Thr Tyr Tyr Phe Lys
                965             970             975
Val Phe Ala Val Ser His Gly Arg Glu Ser Lys Pro Leu Thr Ala Gln
                980             985             990
Gln Thr Thr Lys Leu Asp Ala Pro Thr Asn Leu Gln Phe Val Asn Glu
                995             1000            1005
Thr Asp Ser Thr Val Leu Val Arg Trp Thr Pro Pro Arg Ala Gln
        1010            1015            1020
Ile Thr Gly Tyr Arg Leu Thr Val Gly Leu Thr Arg Arg Gly Gln
        1025            1030            1035
Pro Arg Gln Tyr Asn Val Gly Pro Ser Val Ser Lys Tyr Pro Leu
        1040            1045            1050
```

-continued

```
Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Pro Thr Asp Leu Arg Phe Thr Asn Ile
    1265                1270                1275

Gly Pro Asp Thr Met Arg Val Thr Trp Ala Pro Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440
```

```
Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
1775                1780                1785

Glu Val Ser Val Tyr Ala Leu Lys Asp Thr Leu Thr Ser Arg Pro
1790                1795                1800

Ala Gln Gly Val Val Thr Thr Leu Glu Asn Val Ser Pro Pro Arg
1805                1810                1815

Arg Ala Arg Val Thr Asp Ala Thr Glu Thr Thr Ile Thr Ile Ser
1820                1825                1830

Trp Arg Thr Lys Thr Glu Thr Ile Thr Gly Phe Gln Val Asp Ala
```

-continued

```
            1835                1840                1845

Val Pro Ala Asn Gly Gln Thr Pro Ile Gln Arg Thr Ile Lys Pro
1850                1855                1860

Asp Val Arg Ser Tyr Thr Ile Thr Gly Leu Gln Pro Gly Thr Asp
1865                1870                1875

Tyr Lys Ile Tyr Leu Tyr Thr Leu Asn Asp Asn Ala Arg Ser Ser
1880                1885                1890

Pro Val Val Ile Asp Ala Ser Thr Ala Ile Asp Ala Pro Ser Asn
1895                1900                1905

Leu Arg Phe Leu Ala Thr Thr Pro Asn Ser Leu Leu Val Ser Trp
1910                1915                1920

Gln Pro Pro Arg Ala Arg Ile Thr Gly Tyr Ile Ile Lys Tyr Glu
1925                1930                1935

Lys Pro Gly Ser Pro Pro Arg Glu Val Val Pro Arg Pro Arg Pro
1940                1945                1950

Gly Val Thr Glu Ala Thr Ile Thr Gly Leu Glu Pro Gly Thr Glu
1955                1960                1965

Tyr Thr Ile Tyr Val Ile Ala Leu Lys Asn Asn Gln Lys Ser Glu
1970                1975                1980

Pro Leu Ile Gly Arg Lys Lys Thr Asp Glu Leu Pro Gln Leu Val
1985                1990                1995

Thr Leu Pro His Pro Asn Leu His Gly Pro Glu Ile Leu Asp Val
2000                2005                2010

Pro Ser Thr Val Gln Lys Thr Pro Phe Val Thr His Pro Gly Tyr
2015                2020                2025

Asp Thr Gly Asn Gly Ile Gln Leu Pro Gly Thr Ser Gly Gln Gln
2030                2035                2040

Pro Ser Val Gly Gln Gln Met Ile Phe Glu Glu His Gly Phe Arg
2045                2050                2055

Arg Thr Thr Pro Pro Thr Thr Ala Thr Pro Ile Arg His Arg Pro
2060                2065                2070

Arg Pro Tyr Pro Pro Asn Val Gly Glu Glu Ile Gln Ile Gly His
2075                2080                2085

Ile Pro Arg Glu Asp Val Asp Tyr His Leu Tyr Pro His Gly Pro
2090                2095                2100

Gly Leu Asn Pro Asn Ala Ser Thr Gly Gln Glu Ala Leu Ser Gln
2105                2110                2115

Thr Thr Ile Ser Trp Ala Pro Phe Gln Asp Thr Ser Glu Tyr Ile
2120                2125                2130

Ile Ser Cys His Pro Val Gly Thr Asp Glu Glu Pro Leu Gln Phe
2135                2140                2145

Arg Val Pro Gly Thr Ser Thr Ser Ala Thr Leu Thr Gly Leu Thr
2150                2155                2160

Arg Gly Ala Thr Tyr Asn Ile Ile Val Glu Ala Leu Lys Asp Gln
2165                2170                2175

Gln Arg His Lys Val Arg Glu Glu Val Val Thr Val Gly Asn Ser
2180                2185                2190

Val Asn Glu Gly Leu Asn Gln Pro Thr Asp Asp Ser Cys Phe Asp
2195                2200                2205

Pro Tyr Thr Val Ser His Tyr Ala Val Gly Asp Glu Trp Glu Arg
2210                2215                2220

Met Ser Glu Ser Gly Phe Lys Leu Leu Cys Gln Cys Leu Gly Phe
2225                2230                2235
```

-continued

```
Gly Ser Gly His Phe Arg Cys Asp Ser Ser Arg Trp Cys His Asp
    2240                2245                2250

Asn Gly Val Asn Tyr Lys Ile Gly Glu Lys Trp Asp Arg Gln Gly
    2255                2260                2265

Glu Asn Gly Gln Met Met Ser Cys Thr Cys Leu Gly Asn Gly Lys
    2270                2275                2280

Gly Glu Phe Lys Cys Asp Pro His Glu Ala Thr Cys Tyr Asp Asp
    2285                2290                2295

Gly Lys Thr Tyr His Val Gly Glu Gln Trp Gln Lys Glu Tyr Leu
    2300                2305                2310

Gly Ala Ile Cys Ser Cys Thr Cys Phe Gly Gly Gln Arg Gly Trp
    2315                2320                2325

Arg Cys Asp Asn Cys Arg Arg Pro Gly Gly Glu Pro Ser Pro Glu
    2330                2335                2340

Gly Thr Thr Gly Gln Ser Tyr Asn Gln Tyr Ser Gln Arg Tyr His
    2345                2350                2355

Gln Arg Thr Asn Thr Asn Val Asn Cys Pro Ile Glu Cys Phe Met
    2360                2365                2370

Pro Leu Asp Val Gln Ala Asp Arg Glu Asp Ser Arg Glu
    2375                2380                2385

<210> SEQ ID NO 10
<211> LENGTH: 161
<212> TYPE: PRT
<213> ORGANISM: Homo sapiens

<400> SEQUENCE: 10

Ile Val Thr Cys Gly His Arg Trp Lys Asn Ile Phe Tyr Ile Lys Asn
1               5                   10                  15

Glu Asn Lys Leu Pro Thr Gly Gly Cys Tyr Gly Val Pro Pro Asp Leu
            20                  25                  30

Arg Thr Glu Leu Ser Lys Arg Ile Ala Pro Cys Tyr Gln Asp Tyr Val
        35                  40                  45

Lys Lys Phe Gly Glu Asn Phe Ala Ser Cys Gln Ala Gly Ile Ser Ser
    50                  55                  60

Phe Tyr Thr Lys Asp Leu Ile Val Met Gly Ala Pro Gly Ser Ser Tyr
65                  70                  75                  80

Trp Thr Gly Ser Leu Phe Val Tyr Asn Ile Thr Thr Asn Lys Tyr Lys
                85                  90                  95

Ala Phe Leu Asp Lys Gln Asn Gln Val Lys Phe Gly Ser Tyr Leu Gly
            100                 105                 110

Tyr Ser Val Gly Ala Gly His Phe Arg Ser Gln His Thr Thr Glu Val
        115                 120                 125

Val Gly Gly Ala Pro Gln His Glu Gln Ile Gly Lys Ala Tyr Ile Phe
    130                 135                 140

Ser Ile Asp Glu Lys Glu Leu Asn Ile Leu His Glu Met Lys Gly Lys
145                 150                 155                 160

Lys

<210> SEQ ID NO 11
<211> LENGTH: 20
<212> TYPE: PRT
<213> ORGANISM: Homo sapiens

<400> SEQUENCE: 11
```

```
Gly His Arg Trp Lys Asn Ile Phe Tyr Ile Lys Asn Glu Asn Lys Leu
1               5                   10                  15

Pro Thr Gly Gly
            20
```

<210> SEQ ID NO 12
<211> LENGTH: 14
<212> TYPE: PRT
<213> ORGANISM: Homo sapiens

<400> SEQUENCE: 12

```
Tyr Gln Asp Tyr Val Lys Lys Phe Gly Glu Asn Phe Ala Ser
1               5                   10
```

<210> SEQ ID NO 13
<211> LENGTH: 6
<212> TYPE: PRT
<213> ORGANISM: Homo sapiens

<400> SEQUENCE: 13

```
Ser Tyr Trp Thr Gly Ser
1               5
```

<210> SEQ ID NO 14
<211> LENGTH: 11
<212> TYPE: PRT
<213> ORGANISM: Homo sapiens

<400> SEQUENCE: 14

```
Gly Gly Ala Pro Gln His Glu Gln Ile Gly Lys
1               5                   10
```

<210> SEQ ID NO 15
<211> LENGTH: 10
<212> TYPE: PRT
<213> ORGANISM: Homo sapiens

<400> SEQUENCE: 15

```
Arg Thr Gln Ile Asp Ser Pro Leu Asn Gly
1               5                   10
```

<210> SEQ ID NO 16
<211> LENGTH: 10
<212> TYPE: PRT
<213> ORGANISM: Homo sapiens

<400> SEQUENCE: 16

```
Arg Thr Gln Ile Asp Ser Pro Leu Ser Gly
1               5                   10
```

<210> SEQ ID NO 17
<211> LENGTH: 4
<212> TYPE: PRT
<213> ORGANISM: Homo sapiens

<400> SEQUENCE: 17

```
Lys Leu Glu Lys
1
```

<210> SEQ ID NO 18
<211> LENGTH: 130
<212> TYPE: PRT
<213> ORGANISM: Homo sapiens

<400> SEQUENCE: 18

-continued

```
Ser Glu Pro Leu Ile Gly Arg Lys Lys Thr Asp Glu Leu Pro Gln Leu
1               5                   10                  15

Val Thr Leu Pro His Pro Asn Leu His Gly Pro Glu Ile Leu Asp Val
            20                  25                  30

Pro Ser Thr Val Gln Lys Thr Pro Phe Val Thr His Pro Gly Tyr Asp
        35                  40                  45

Thr Gly Asn Gly Ile Gln Leu Pro Gly Thr Ser Gly Gln Gln Pro Ser
    50                  55                  60

Val Gly Gln Gln Met Ile Phe Glu His Gly Phe Arg Arg Thr Thr
65                  70                  75                  80

Pro Pro Thr Thr Ala Thr Pro Ile Arg His Arg Pro Arg Pro Tyr Pro
            85                  90                  95

Pro Asn Val Gly Glu Glu Ile Gln Ile Gly His Ile Pro Arg Glu Asp
            100                 105                 110

Val Asp Tyr His Leu Tyr Pro His Gly Pro Gly Leu Asn Pro Asn Ala
            115                 120                 125

Ser Thr
    130

<210> SEQ ID NO 19
<211> LENGTH: 3
<212> TYPE: PRT
<213> ORGANISM: Homo sapiens

<400> SEQUENCE: 19

Leu Asp Val
1

<210> SEQ ID NO 20
<211> LENGTH: 4
<212> TYPE: PRT
<213> ORGANISM: Homo sapiens

<400> SEQUENCE: 20

Arg Glu Asp Val
1

<210> SEQ ID NO 21
<211> LENGTH: 5
<212> TYPE: PRT
<213> ORGANISM: Homo sapiens

<400> SEQUENCE: 21

Ile Asp Ala Pro Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Glu Ile Leu Asp Val Pro Ser Thr
1               5

<210> SEQ ID NO 23
<211> LENGTH: 25
<212> TYPE: PRT
<213> ORGANISM: Artificial Sequence
```

<220> FEATURE:
<223> OTHER INFORMATION: Synthetic

<400> SEQUENCE: 23

Asp Glu Leu Pro Gln Leu Val Thr Leu Pro His Pro Asn Leu His Gly
1               5                   10                  15
Pro Glu Ile Leu Asp Val Pro Ser Thr
            20                  25

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

His Gly Pro Glu Ile Leu Asp Val Pro Ser Thr
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Glu Ile Leu Asp Val
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic

<400> SEQUENCE: 26

Leu Asp Val Pro
1

<210> SEQ ID NO 27
<211> LENGTH: 3
<212> TYPE: PRT
<213> ORGANISM: Artificial Sequence
<220> FEATURE:
<223> OTHER INFORMATION: Synthetic

<400> SEQUENCE: 27

Leu Asp Val
1

<210> SEQ ID NO 28
<211> LENGTH: 4
<212> TYPE: PRT
<213> ORGANISM: Artificial Sequence
<220> FEATURE:
<223> OTHER INFORMATION: Synthetic

<400> SEQUENCE: 28

Ile Asp Ala Pro
1

<210> SEQ ID NO 29
<211> LENGTH: 3

```
<212> TYPE: PRT
<213> ORGANISM: Artificial Sequence
<220> FEATURE:
<223> OTHER INFORMATION: Synthetic

<400> SEQUENCE: 29

Arg Asp Val
1

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Gly Pro Glu Tyr Leu Asp Val Pro
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at this position can be any amino acid or
      modified amino acid..
<220> FEATURE:
<221> NAME/KEY: MISC_FEATURE
<222> LOCATION: (2)..(2)
<223> OTHER INFORMATION: Cyclization point.
<220> FEATURE:
<221> NAME/KEY: MISC_FEATURE
<222> LOCATION: (3)..(3)
<223> OTHER INFORMATION: X at this position can be any amino acid or
      modified amino acid..
<220> FEATURE:
<221> NAME/KEY: MISC_FEATURE
<222> LOCATION: (5)..(5)
<223> OTHER INFORMATION: Cyclization point.

<400> SEQUENCE: 31

Xaa Cys Xaa Pro Cys
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Cyclization point.
<220> FEATURE:
<221> NAME/KEY: MISC_FEATURE
<222> LOCATION: (5)..(5)
<223> OTHER INFORMATION: Cyclization point.

<400> SEQUENCE: 32

Arg Cys Asp Pro Cys
1               5

<210> SEQ ID NO 33
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Cyclization point.
<220> FEATURE:
<221> NAME/KEY: MISC_FEATURE
<222> LOCATION: (6)..(6)
<223> OTHER INFORMATION: Cyclization point.

<400> SEQUENCE: 33

Cys Trp Leu Asp Val Cys
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Cycylization point.
<220> FEATURE:
<221> NAME/KEY: MISC_FEATURE
<222> LOCATION: (5)..(5)
<223> OTHER INFORMATION: Cycylization point.

<400> SEQUENCE: 34

Tyr Cys Ala Pro Cys
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Cyclization point.
<220> FEATURE:
<221> NAME/KEY: MISC_FEATURE
<222> LOCATION: (5)..(5)
<223> OTHER INFORMATION: Cyclization point.

<400> SEQUENCE: 35

Tyr Cys Asp Pro Cys
1               5

<210> SEQ ID NO 36
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: The amino acid at this position is D-Phe.

<400> SEQUENCE: 36

Cys Asp Phe Cys
1

<210> SEQ ID NO 37
<211> LENGTH: 5
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Cyclization point.
<220> FEATURE:
<221> NAME/KEY: MISC_FEATURE
<222> LOCATION: (4)..(4)
<223> OTHER INFORMATION: The amino acid at this position is ThioP.
<220> FEATURE:
<221> NAME/KEY: MISC_FEATURE
<222> LOCATION: (5)..(5)
<223> OTHER INFORMATION: Cyclization point.

<400> SEQUENCE: 37

Arg Cys Asp Pro Cys
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: cyclization point.
<220> FEATURE:
<221> NAME/KEY: MISC_FEATURE
<222> LOCATION: (4)..(4)
<223> OTHER INFORMATION: The amino acid at this position is ThioP.
<220> FEATURE:
<221> NAME/KEY: MISC_FEATURE
<222> LOCATION: (5)..(5)
<223> OTHER INFORMATION: Cyclization point.

<400> SEQUENCE: 38

Arg Cys Asp Pro Cys
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Glu Gly Tyr Tyr Gly Asn Tyr Gly Val Tyr Ala
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X at this position is any amino acid or
      modified amino acid.
<220> FEATURE:
<221> NAME/KEY: MISC_FEATURE
<222> LOCATION: (2)..(2)
<223> OTHER INFORMATION: Cyclization point.
<220> FEATURE:
<221> NAME/KEY: MISC_FEATURE
<222> LOCATION: (5)..(5)
```

<223> OTHER INFORMATION: Cyclization point.

<400> SEQUENCE: 40

Xaa Cys Asp Pro Cys
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Cys Gly Arg Gly Asp Ser Pro Cys
1               5

<210> SEQ ID NO 42
<211> LENGTH: 67
<212> TYPE: PRT
<213> ORGANISM: Echis carinatus

<400> SEQUENCE: 42

Asn Ser Val His Pro Cys Cys Asp Pro Val Thr Cys Glu Pro Arg Glu
1               5                   10                  15

Gly Glu His Cys Ile Ser Gly Pro Cys Cys Arg Asn Cys Lys Phe Leu
                20                  25                  30

Asn Ala Gly Thr Ile Cys Lys Arg Ala Met Leu Asp Gly Leu Asn Asp
            35                  40                  45

Tyr Cys Thr Gly Lys Ser Ser Asp Cys Pro Arg Asn Arg Tyr Lys Gly
    50                  55                  60

Lys Glu Asp
65

<210> SEQ ID NO 43
<211> LENGTH: 4
<212> TYPE: PRT
<213> ORGANISM: Echis carinatus

<400> SEQUENCE: 43

Met Leu Asp Gly
1

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Arg Thr Gln Ile Asp Ser Pro Leu Asn
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Thr Gln Ile Asp Ser Pro
1               5

```
<210> SEQ ID NO 46
<211> LENGTH: 4
<212> TYPE: PRT
<213> ORGANISM: Artificial Sequence
<220> FEATURE:
<223> OTHER INFORMATION: Synthetic

<400> SEQUENCE: 46

Gln Ile Asp Ser
1

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Ile Asp Ser Pro
1

<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Lys Leu Glu Lys
1

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Gly Pro Glu Tyr Leu Asp Val Pro
1               5

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Leu Asp Val Pro
1

<210> SEQ ID NO 51
<211> LENGTH: 4
<212> TYPE: PRT
<213> ORGANISM: Artificial Sequence
<220> FEATURE:
<223> OTHER INFORMATION: Synthetic

<400> SEQUENCE: 51

Ile Leu Asp Val
1
```

```
<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Glu Ile Leu Asp Val Pro Ser Thr
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Glu Ile Leu Glu Val Pro Ser Thr
1               5

<210> SEQ ID NO 54
<211> LENGTH: 52
<212> TYPE: PRT
<213> ORGANISM: Homo sapiens

<400> SEQUENCE: 54

Tyr Asn Val Asp Thr Glu Ser Ala Leu Leu Tyr Gln Gly Pro His Asn
1               5                   10                  15

Thr Ile Phe Gly Tyr Ser Val Val Leu His Ser His Gly Ala Asn Arg
            20                  25                  30

Trp Leu Leu Val Gly Ala Pro Thr Ala Asn Trp Leu Ala Asn Ala Ser
        35                  40                  45

Val Ile Asn Pro
    50

<210> SEQ ID NO 55
<211> LENGTH: 60
<212> TYPE: PRT
<213> ORGANISM: Homo sapiens

<400> SEQUENCE: 55

Gly Arg Pro Tyr Asn Val Asp Thr Glu Ser Ala Leu Leu Tyr Gln Gly
1               5                   10                  15

Pro His Asn Thr Leu Phe Gly Tyr Ser Val Val Leu His Ser His Gly
            20                  25                  30

Ala Asn Arg Trp Leu Leu Val Gly Ala Pro Thr Ala Asn Trp Leu Ala
        35                  40                  45

Asn Ala Ser Val Ile Asn Pro Gly Ala Ile Tyr Arg
    50                  55                  60

<210> SEQ ID NO 56
<211> LENGTH: 74
<212> TYPE: PRT
<213> ORGANISM: Homo sapiens

<400> SEQUENCE: 56

Gly Val Pro Thr Gly Arg Pro Tyr Asn Val Asp Thr Glu Ser Ala Leu
1               5                   10                  15

Leu Tyr Gln Gly Pro His Asn Thr Leu Phe Gly Tyr Ser Val Val Leu
            20                  25                  30
```

-continued

His Ser His Gly Ala Asn Arg Trp Leu Leu Val Gly Ala Pro Thr Ala
            35                  40                  45

Asn Trp Leu Ala Asn Ala Ser Val Ile Asn Pro Gly Ala Ile Tyr Arg
        50                  55                  60

Cys Arg Ile Gly Lys Asn Pro Gly Gln Thr
65                  70

<210> SEQ ID NO 57
<211> LENGTH: 27
<212> TYPE: PRT
<213> ORGANISM: Homo sapiens

<400> SEQUENCE: 57

Ile Val Thr Cys Gly His Arg Trp Lys Asn Ile Phe Tyr Ile Lys Asn
1               5                   10                  15

Glu Asn Lys Leu Pro Thr Gly Gly Cys Tyr Gly
            20                  25

<210> SEQ ID NO 58
<211> LENGTH: 34
<212> TYPE: PRT
<213> ORGANISM: Homo sapiens

<400> SEQUENCE: 58

Gly His Arg Trp Lys Asn Ile Phe Tyr Ile Lys Asn Glu Asn Lys Leu
1               5                   10                  15

Pro Thr Gly Gly Cys Tyr Gly Val Pro Pro Asp Leu Arg Thr Glu Leu
            20                  25                  30

Ser Lys

<210> SEQ ID NO 59
<211> LENGTH: 17
<212> TYPE: PRT
<213> ORGANISM: Homo sapiens

<400> SEQUENCE: 59

Ala Pro Cys Tyr Gln Asp Tyr Val Lys Lys Phe Gly Glu Asn Phe Ala
1               5                   10                  15

Ser

<210> SEQ ID NO 60
<211> LENGTH: 28
<212> TYPE: PRT
<213> ORGANISM: Homo sapiens

<400> SEQUENCE: 60

Cys Tyr Gln Asp Tyr Val Lys Lys Phe Gly Glu Asn Phe Ala Ser Cys
1               5                   10                  15

Gln Ala Gly Ile Ser Ser Phe Tyr Thr Lys Asp Leu
            20                  25

<210> SEQ ID NO 61
<211> LENGTH: 14
<212> TYPE: PRT
<213> ORGANISM: Homo sapiens

<400> SEQUENCE: 61

Gly Ser Ser Tyr Trp Thr Gly Ser Leu Phe Val Tyr Asn Ile
1               5                   10

```
<210> SEQ ID NO 62
<211> LENGTH: 20
<212> TYPE: PRT
<213> ORGANISM: Homo sapiens

<400> SEQUENCE: 62

Arg Ser Gln His Thr Thr Glu Val Val Gly Gly Ala Pro Gln His Glu
1               5                   10                  15

Gln Ile Gly Lys
            20

<210> SEQ ID NO 63
<211> LENGTH: 22
<212> TYPE: PRT
<213> ORGANISM: Homo sapiens

<400> SEQUENCE: 63

Gly Gly Ala Pro Gln His Glu Gln Ile Gly Lys Ala Tyr Ile Phe Ser
1               5                   10                  15

Ile Asp Glu Lys Glu Leu
            20

<210> SEQ ID NO 64
<211> LENGTH: 12
<212> TYPE: PRT
<213> ORGANISM: Homo sapiens

<400> SEQUENCE: 64

Gly Gly Ala Pro Gln His Glu Gln Ile Gly Lys Ala
1               5                   10

<210> SEQ ID NO 65
<211> LENGTH: 12
<212> TYPE: PRT
<213> ORGANISM: Homo sapiens

<400> SEQUENCE: 65

Trp Arg Thr Gln Ile Asp Ser Pro Leu Asn Gly Lys
1               5                   10

<210> SEQ ID NO 66
<211> LENGTH: 14
<212> TYPE: PRT
<213> ORGANISM: Homo sapiens

<400> SEQUENCE: 66

Ser Trp Arg Thr Gln Ile Asp Ser Pro Leu Asn Gly Lys Val
1               5                   10

<210> SEQ ID NO 67
<211> LENGTH: 15
<212> TYPE: PRT
<213> ORGANISM: Homo sapiens

<400> SEQUENCE: 67

Ser Trp Arg Thr Gln Ile Asp Ser Pro Leu Asn Gly Lys Val Thr
1               5                   10                  15

<210> SEQ ID NO 68
<211> LENGTH: 20
<212> TYPE: PRT
<213> ORGANISM: Homo sapiens

<400> SEQUENCE: 68
```

Pro Phe Phe Ser Trp Arg Thr Gln Ile Asp Ser Pro Leu Asn Gly Lys
1               5                   10                  15

Val Thr Asn Glu
            20

<210> SEQ ID NO 69
<211> LENGTH: 8
<212> TYPE: PRT
<213> ORGANISM: Homo sapiens

<400> SEQUENCE: 69

Ser Arg Lys Leu Glu Lys Gly Ile
1               5

<210> SEQ ID NO 70
<211> LENGTH: 12
<212> TYPE: PRT
<213> ORGANISM: Homo sapiens

<400> SEQUENCE: 70

Cys Glu Ser Arg Lys Leu Glu Lys Gly Ile Gln Val
1               5                   10

<210> SEQ ID NO 71
<211> LENGTH: 16
<212> TYPE: PRT
<213> ORGANISM: Homo sapiens

<400> SEQUENCE: 71

Ala Thr Cys Glu Ser Arg Lys Leu Glu Lys Gly Ile Gln Val Glu Ile
1               5                   10                  15

<210> SEQ ID NO 72
<211> LENGTH: 27
<212> TYPE: PRT
<213> ORGANISM: Homo sapiens

<400> SEQUENCE: 72

Leu Cys Thr Ala Thr Cys Glu Ser Arg Lys Leu Glu Lys Gly Ile Gln
1               5                   10                  15

Val Glu Ile Tyr Ser Phe Pro Lys Asp Pro Glu
            20                  25

<210> SEQ ID NO 73
<211> LENGTH: 13
<212> TYPE: PRT
<213> ORGANISM: Homo sapiens

<400> SEQUENCE: 73

Gly His Lys Lys Leu Glu Lys Gly Ile Gln Val Glu Leu
1               5                   10

<210> SEQ ID NO 74
<211> LENGTH: 12
<212> TYPE: PRT
<213> ORGANISM: Homo sapiens

<400> SEQUENCE: 74

Val Thr Cys Gly His Lys Lys Leu Glu Lys Gly Ile
1               5                   10

<210> SEQ ID NO 75
<211> LENGTH: 23
<212> TYPE: PRT

<213> ORGANISM: Homo sapiens

<400> SEQUENCE: 75

Thr Cys Gly His Lys Lys Leu Glu Lys Gly Ile Gln Val Glu Leu Tyr
1               5                   10                  15
Ser Phe Pro Arg Asp Pro Glu
            20

<210> SEQ ID NO 76
<211> LENGTH: 24
<212> TYPE: PRT
<213> ORGANISM: Homo sapiens

<400> SEQUENCE: 76

Pro Val Ser Phe Glu Asn Glu His Ser Tyr Leu Cys Thr Val Thr Cys
1               5                   10                  15
Gly His Lys Lys Leu Glu Lys Gly
            20

<210> SEQ ID NO 77
<211> LENGTH: 11
<212> TYPE: PRT
<213> ORGANISM: Homo sapiens

<400> SEQUENCE: 77

Arg Thr Gln Ile Asp Ser Pro Leu Ser Gly Lys
1               5                   10

<210> SEQ ID NO 78
<211> LENGTH: 16
<212> TYPE: PRT
<213> ORGANISM: Homo sapiens

<400> SEQUENCE: 78

Phe Ser Trp Arg Thr Gln Ile Asp Ser Pro Leu Ser Gly Lys Val Arg
1               5                   10                  15

<210> SEQ ID NO 79
<211> LENGTH: 18
<212> TYPE: PRT
<213> ORGANISM: Homo sapiens

<400> SEQUENCE: 79

Glu Ser Pro Ser Phe Trp Trp Arg Thr Gln Ile Asp Ser Pro Leu Ser
1               5                   10                  15
Gly Lys

<210> SEQ ID NO 80
<211> LENGTH: 13
<212> TYPE: PRT
<213> ORGANISM: Homo sapiens

<400> SEQUENCE: 80

Thr Ala Ile Asp Ala Pro Ser Asn Leu Arg Asp Ala Ser
1               5                   10

<210> SEQ ID NO 81
<211> LENGTH: 16
<212> TYPE: PRT
<213> ORGANISM: Homo sapiens

<400> SEQUENCE: 81

Thr Ala Ile Asp Ala Pro Ser Asn Leu Arg Phe Leu Ala Thr Thr Pro

-continued

```
1               5                   10                  15
```

<210> SEQ ID NO 82
<211> LENGTH: 17
<212> TYPE: PRT
<213> ORGANISM: Homo sapiens

<400> SEQUENCE: 82

```
Arg Ser Ser Pro Val Val Ile Asp Ala Ser Thr Ala Ile Asp Ala Pro
1               5                   10                  15

Ser
```

<210> SEQ ID NO 83
<211> LENGTH: 19
<212> TYPE: PRT
<213> ORGANISM: Homo sapiens

<400> SEQUENCE: 83

```
Ile Asp Ala Pro Ser Asn Leu Arg Phe Leu Ala Thr Thr Pro Asn Ser
1               5                   10                  15

Leu Leu Val
```

<210> SEQ ID NO 84
<211> LENGTH: 36
<212> TYPE: PRT
<213> ORGANISM: Homo sapiens

<400> SEQUENCE: 84

```
Ile Asp Ala Pro Ser Asn Leu Arg Phe Leu Ala Thr Thr Pro Asn Ser
1               5                   10                  15

Leu Leu Val Ser Trp Gln Pro Pro Arg Ala Arg Ile Thr Gly Tyr Ile
            20                  25                  30

Ile Lys Tyr Glu
            35
```

<210> SEQ ID NO 85
<211> LENGTH: 7
<212> TYPE: PRT
<213> ORGANISM: Homo sapiens

<400> SEQUENCE: 85

```
Ile Asp Asp Val Pro Ser Thr
1               5
```

<210> SEQ ID NO 86
<211> LENGTH: 16
<212> TYPE: PRT
<213> ORGANISM: Homo sapiens

<400> SEQUENCE: 86

```
Asn Leu His Gly Pro Glu Ile Leu Asp Val Pro Ser Thr Val Gln Lys
1               5                   10                  15
```

<210> SEQ ID NO 87
<211> LENGTH: 13
<212> TYPE: PRT
<213> ORGANISM: Homo sapiens

<400> SEQUENCE: 87

```
Pro His Pro Asn Leu His Gly Pro Glu Ile Leu Asp Val
1               5                   10
```

```
<210> SEQ ID NO 88
<211> LENGTH: 20
<212> TYPE: PRT
<213> ORGANISM: Homo sapiens

<400> SEQUENCE: 88

Ile Leu Asp Val Pro Ser Thr Val Gln Lys Thr Pro Phe Val Thr His
1               5                   10                  15

Pro Gly Tyr Asp
            20

<210> SEQ ID NO 89
<211> LENGTH: 17
<212> TYPE: PRT
<213> ORGANISM: Homo sapiens

<400> SEQUENCE: 89

Val Thr Leu Pro His Pro Asn Leu His Gly Pro Glu Ile Leu Asp Val
1               5                   10                  15

Pro

<210> SEQ ID NO 90
<211> LENGTH: 5
<212> TYPE: PRT
<213> ORGANISM: Homo sapiens

<400> SEQUENCE: 90

Glu Ile Leu Asp Val
1               5

<210> SEQ ID NO 91
<211> LENGTH: 8
<212> TYPE: PRT
<213> ORGANISM: Homo sapiens

<400> SEQUENCE: 91

Ile Pro Arg Glu Asp Val Asp Tyr
1               5

<210> SEQ ID NO 92
<211> LENGTH: 9
<212> TYPE: PRT
<213> ORGANISM: Homo sapiens

<400> SEQUENCE: 92

Gly His Ile Pro Arg Asp Asp Val Asp
1               5

<210> SEQ ID NO 93
<211> LENGTH: 8
<212> TYPE: PRT
<213> ORGANISM: Homo sapiens

<400> SEQUENCE: 93

Gly His Ile Pro Arg Glu Asp Val
1               5

<210> SEQ ID NO 94
<211> LENGTH: 84
<212> TYPE: PRT
<213> ORGANISM: Homo sapiens

<400> SEQUENCE: 94

Leu Asp Val Pro Ser Thr Val Gln Lys Thr Pro Phe Val Thr His Pro
```

```
                          1               5                  10                 15
Gly Tyr Asp Thr Gly Asn Gly Ile Gln Leu Pro Gly Thr Ser Gly Gln
                 20                  25                 30

Gln Pro Ser Val Gly Gln Gln Met Ile Phe Glu Glu His Gly Phe Arg
             35                  40                  45

Arg Thr Thr Pro Pro Thr Thr Ala Thr Pro Ile Arg His Arg Pro Arg
         50                  55                  60

Pro Tyr Pro Pro Asn Val Gly Glu Glu Ile Gln Ile Gly His Ile Pro
 65                  70                  75                  80

Arg Glu Asp Val

<210> SEQ ID NO 95
<211> LENGTH: 90
<212> TYPE: PRT
<213> ORGANISM: Homo sapiens

<400> SEQUENCE: 95

Pro Glu Ile Leu Asp Val Pro Ser Thr Val Gln Lys Thr Pro Phe Val
 1               5                  10                  15

Thr His Pro Gly Tyr Asp Thr Gly Asn Gly Ile Gln Leu Pro Gly Thr
                 20                  25                  30

Ser Gly Gln Gln Pro Ser Val Gly Gln Gln Met Ile Phe Glu Glu His
             35                  40                  45

Gly Phe Arg Arg Thr Thr Pro Pro Thr Thr Thr Ala Thr Pro Ile Arg
         50                  55                  60

His Arg Pro Arg Pro Tyr Pro Pro Asn Val Gly Glu Glu Ile Gln Ile
 65                  70                  75                  80

Gly His Ile Pro Arg Glu Asp Val Asp Tyr
                 85                  90

<210> SEQ ID NO 96
<211> LENGTH: 647
<212> TYPE: PRT
<213> ORGANISM: Homo sapiens

<400> SEQUENCE: 96

Met Pro Gly Lys Met Val Val Ile Leu Gly Ala Ser Asn Ile Leu Trp
 1               5                  10                  15

Ile Met Phe Ala Ala Ser Gln Ala Phe Lys Ile Glu Thr Thr Pro Glu
                 20                  25                  30

Ser Arg Tyr Leu Ala Gln Ile Gly Asp Ser Val Ser Leu Thr Cys Ser
             35                  40                  45

Thr Thr Gly Cys Glu Ser Pro Phe Phe Ser Trp Arg Thr Gln Ile Asp
         50                  55                  60

Ser Pro Leu Asn Gly Lys Val Thr Asn Glu Gly Thr Thr Ser Thr Leu
 65                  70                  75                  80

Thr Met Asn Pro Val Ser Phe Gly Asn Glu His Ser Tyr Leu Cys Thr
                 85                  90                  95

Ala Thr Cys Glu Ser Arg Lys Leu Glu Lys Gly Ile Gln Val Glu Ile
                100                 105                 110

Tyr Ser Phe Pro Lys Asp Pro Glu Ile His Leu Ser Gly Pro Leu Glu
            115                 120                 125

Ala Gly Lys Pro Ile Thr Val Lys Cys Ser Val Ala Asp Val Tyr Pro
        130                 135                 140

Phe Asp Arg Leu Glu Ile Asp Leu Leu Lys Gly Asp His Leu Met Lys
145                 150                 155                 160
```

-continued

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
                260                 265                 270

Asn Ala Thr Leu Thr Leu Ile Ala Met Arg Met Glu Asp Ser Gly Ile
            275                 280                 285

Tyr Val Cys Glu Gly Val Asn Leu Ile Gly Lys Asn Arg Lys Glu Val
        290                 295                 300

Glu Leu Ile Val Gln Ala Phe Pro Arg Asp Pro Glu Ile Glu Met Ser
305                 310                 315                 320

Gly Gly Leu Val Asn Gly Ser Ser Val Thr Val Ser Cys Lys Val Pro
                325                 330                 335

Ser Val Tyr Pro Leu Asp Arg Leu Glu Ile Glu Leu Leu Lys Gly Glu
                340                 345                 350

Thr Ile Leu Glu Asn Ile Glu Phe Leu Glu Asp Thr Asp Met Lys Ser
            355                 360                 365

Leu Glu Asn Lys Ser Leu Glu Met Thr Phe Ile Pro Thr Ile Glu Asp
        370                 375                 380

Thr Gly Lys Ala Leu Val Cys Gln Ala Lys Leu His Ile Asp Asp Met
385                 390                 395                 400

Glu Phe Glu Pro Lys Gln Arg Gln Ser Thr Gln Thr Leu Tyr Val Asn
                405                 410                 415

Val Ala Pro Arg Asp Thr Thr Val Leu Val Ser Pro Ser Ser Ile Leu
                420                 425                 430

Glu Glu Gly Ser Ser Val Asn Met Thr Cys Leu Ser Gln Gly Phe Pro
            435                 440                 445

Ala Pro Lys Ile Leu Trp Ser Arg Gln Leu Pro Asn Gly Glu Leu Gln
        450                 455                 460

Pro Leu Ser Glu Asn Ala Thr Leu Thr Leu Ile Ser Thr Lys Met Glu
465                 470                 475                 480

Asp Ser Gly Val Tyr Leu Cys Glu Gly Ile Asn Gln Ala Gly Arg Ser
                485                 490                 495

Arg Lys Glu Val Glu Leu Ile Ile Gln Val Thr Pro Lys Asp Ile Lys
            500                 505                 510

Leu Thr Ala Phe Pro Ser Glu Ser Val Lys Glu Gly Asp Thr Val Ile
        515                 520                 525

Ile Ser Cys Thr Cys Gly Asn Val Pro Glu Thr Trp Ile Ile Leu Lys
        530                 535                 540

Lys Lys Ala Glu Thr Gly Asp Thr Val Leu Lys Ser Ile Asp Gly Ala
545                 550                 555                 560

Tyr Thr Ile Arg Lys Ala Gln Leu Lys Asp Ala Gly Val Tyr Glu Cys
                565                 570                 575

```
                           -continued

Glu Ser Lys Asn Lys Val Gly Ser Gln Leu Arg Ser Leu Thr Leu Asp
            580                 585                 590

Val Gln Gly Arg Glu Asn Asn Lys Asp Tyr Phe Ser Pro Glu Leu Leu
        595                 600                 605

Val Leu Tyr Phe Ala Ser Ser Leu Ile Ile Pro Ala Ile Gly Met Ile
    610                 615                 620

Ile Tyr Phe Ala Arg Lys Ala Asn Met Lys Gly Ser Tyr Ser Leu Val
625                 630                 635                 640

Glu Ala Gln Lys Ser Lys Val
                645

<210> SEQ ID NO 97
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Cyclization point
<220> FEATURE:
<221> NAME/KEY: MISC_FEATURE
<222> LOCATION: (6)..(6)
<223> OTHER INFORMATION: Cyclization point

<400> SEQUENCE: 97

Cys Tyr Tyr Gly Asn Cys
1               5
```

METHODS FOR INHIBITING ANGIOGENESIS

This application is the U.S. National stage filing of PCT Application No. PCT/US02/24573, filed on Aug. 1, 2002, which claims priority to U.S. provisional Patent Application Ser. No. 60/310,645, filed Aug. 6, 2001, now abandoned.

This invention was made, in part, with government support under grant numbers CA71619 and CA 83133 awarded by the National Cancer Institute of the National Institutes of Health. The U.S. government has certain rights in the invention.

FIELD OF THE INVENTION

The present invention provides methods for detecting and inhibiting angiogenesis, endothelial cell adhesion, and endothelial cell migration. In preferred embodiments, the present invention utilizes agents that inhibit the specific binding of integrin $\alpha 4\beta 1$ to one or more of its ligands. The invention further relates to methods for screening test compounds for their ability to inhibit angiogenesis, endothelial cell adhesion, or endothelial cell migration by employing agents which inhibit the specific binding of integrin $\alpha 4\beta 1$ to one or more of its ligands. The invention additionally relates to methods for isolating endothelial cells which express integrin $\alpha 4\beta 1$. The methods of the invention are useful in, for example, diagnosing and inhibiting pathological conditions that are associated with angiogenesis, endothelial cell adhesion, and/or endothelial cell migration. The invention's methods are also useful in isolating endothelial progenitor cells, and in determining the mechanisms that underlie angiogenesis, development, wound healing, and the function of the female reproductive system.

BACKGROUND OF THE INVENTION

Angiogenesis is essential in the female reproduction system and during development and wound repair. However, inappropriate angiogenesis can have severe consequences. Indeed, the proliferation of new blood vessels from pre-existing capillaries plays a key role in diseases, such as the pathological development of solid tumor cancers, solid tumor metastases, angiofibromas, skin cancer, retrolental fibroplasia, Kaposi's sarcoma, childhood hemangiomas, diabetic retinopathy, neovascular glaucoma, age related macular degeneration, psoriasis, gingivitis, rheumatoid arthritis, osteoarthritis, ulcerative colitis, Crohn's disease, inflammatory bowel disease, and capillary proliferation in atherosclerotic plaques. Because these serious diseases afflict several million people in the United States each year, considerable scientific effort has been directed toward gaining an understanding of the mechanisms regulating angiogenesis and toward developing therapies for such diseases.

With respect to cancer, over six hundred thousand new cases of lung, colon, breast and prostate cancer will be diagnosed in the United States each year, accounting for 75% of new solid tumor cancers and 77% of solid tumor cancer deaths. Although advances in therapy and in our understanding of cancer causes and risk factors have lead to improved outcomes overall, most cancers still have low five year survival rates. Despite these advances in primary tumor management, 50% of patients will ultimately die of their disease largely due to side effects of current therapies or to the metastatic spread of tumors to numerous or inoperable sites through the tumor associated vasculature. It is now known that the growth and spread of solid tumor cancer depends on the development of a tumor-associated vasculature by a process known as angiogenesis.

One of the most significant consequences of tumor angiogenesis is the invasion of tumor cells into the vasculature. Thus, vascularization permits the survival and growth of primary tumors, as well as the metastatic spread of cancer. Metastases arise from tumor cells which enter the tumor's own vasculature to be carried to local and distant sites where they create new tumors. Tumors have typically established a vasculature and metastasized to local and distant sites by the time that primary tumors are detectable.

Current treatments for cancer rely mainly on treatments which are not selective for the disease but which have deleterious effects on other organs of the body. For example, chemotherapeutics reagents or radiation have serious side effects because they kill or impair all proliferating cells in the body, including healthy cells. Side effects are unpleasant and often create health problems that themselves increase patient mortality.

Angiogenesis also plays a major role in the progression and exacerbation of a number of inflammatory diseases. Psoriasis, a disease which afflicts 2 million Americans, is characterized by significant angiogenesis. In rheumatoid arthritis and possibly osteoarthritis, the influx of lymphocytes into joints induces blood vessels of the joint synovial lining to undergo angiogenesis; this angiogenesis appears to permit a greater influx of leukocytes and the destruction of cartilage and bone. Angiogenesis is also likely to play a role in chronic inflammatory diseases such as ulcerative colitis and Crohn's disease. In addition, the growth of capillaries into atherosclerotic plaques is a serious problem; the rupture and hemorrhage of vascularized plaques is thought to cause coronary thrombosis. To date, however, no effective therapies exist for these diseases.

Angiogenesis is also a factor in many ophthalmic disorders which can lead to blindness. In age-related macular degeneration (ARMD), a disorder afflicting 25% of otherwise healthy individuals over the age of 60, and in diabetic retinopathy, a condition prevalent among both juvenile and late onset diabetics, angiogenesis is induced by hypoxic conditions on the choroid or the retina, respectively. Hypoxia induces an increase in the secretion of growth factors including vascular endothelial growth factor (VEGF). It is possible that VEGF expression in the eye induces the migration and proliferation of endothelial cells into regions of the eye where they are not ordinarily found. Vascularization in ocular tissue has adverse effects on vision. New blood vessels on the cornea can induce corneal scarring, whereas new blood vessels on the retina can induce retinal detachment, and angiogenic vessels in the choroid may leak vision-obscuring fluids; these events often lead to blindness.

For other pathological conditions associated with abnormal angiogenesis such as diabetic retinopathy, there are no effective treatments short of retinal transplants. However, even in cases where retinal transplantation is performed, the new retina is subject to the same conditions that resulted in the original retinopathy.

While agents that prevent continued angiogenesis are currently being tested, there remains a need to identify the molecular interactions involved in the undesirable angiogenesis that occurs in certain pathological conditions, and to develop methods for diagnosing and specifically treating such pathologies.

SUMMARY OF THE INVENTION

The present invention satisfies the need in the art for identifying the molecular interactions involved in the undesirable angiogenesis that occurs in certain pathological conditions, and for developing methods for diagnosing and specifically treating such pathologies.

In particularly preferred embodiments, the invention provides a method for inhibiting angiogenesis in a tissue, comprising: a) providing at least one tissue and an agent which inhibits specific binding of integrin α4β1 to an integrin α4β1 ligand; b) treating the tissue with the agent under conditions such that specific binding of integrin α4β1 to the integrin α4β1 ligand is inhibited and a treated tissue is produced; and c) observing inhibition of angiogenesis in the treated tissue. In one embodiment, the tissue is in a subject. In a preferred embodiment, subject has tissue angiogenesis. In another preferred embodiment, the subject is suspected of being capable of developing angiogenesis in the tissue. In yet another preferred embodiment, the tissue comprises ocular tissue, skin tissue, bone tissue, or synovial tissue. In a more preferred embodiment, the ocular tissue is selected from the retina, macula, cornea, choroids, and vitreous humor. In an alternative embodiment, the tissue comprises a tumor. In a preferred embodiment, the tumor is malignant. In a more preferred embodiment, the malignant tumor is metastatic. In yet another embodiment, the agent comprises a peptide. In an alternative embodiment, the agent comprises an antibody. In a further preferred embodiment, the antibody is an anti-integrin α4β1 antibody. In another preferred embodiment, the antibody is an anti-vascular cell adhesion molecule antibody. In yet another preferred embodiment, the antibody is an anti-fibronectin antibody. In an alternative embodiment, the agent comprises an antisense sequence. In a preferred embodiment, antisense sequence is an integrin α4β1 antisense sequence. In another preferred embodiment, the antisense sequence is a vascular cell adhesion molecule antisense sequence. In yet another preferred embodiment, the antisense sequence is a fibronectin antisense sequence. In yet another alternative embodiment, the agent comprises a ribozyme. In a preferred embodiment, the ribozyme is an integrin α4β1 ribozyme. In another preferred embodiment, the ribozyme is a vascular cell adhesion molecule ribozyme. In yet another preferred embodiment, the ribozyme is a fibronectin ribozyme. In an alternative embodiment, the ligand is vascular cell adhesion molecule. In a preferred embodiment, the ligand is fibronectin.

Also provided herein are methods for inhibiting endothelial cell adhesion, comprising: a) providing endothelial cells and an agent which inhibits specific binding of integrin α4β1 to an integrin α4β1 ligand; b) treating the endothelial cells with the agent under conditions such that specific binding of integrin α4β1 to the integrin α4β1 ligand is inhibited and treated endothelial cells are produced; and c) observing inhibition of cell adhesion of the treated endothelial cells.

The invention further provides methods for inhibiting endothelial cell migration, comprising: a) providing endothelial cells and an agent which inhibits specific binding of integrin α4β1 to an integrin α4β1 ligand; b) treating the endothelial cells with the agent under conditions such that specific binding of integrin α4β1 to the integrin α4β1 ligand is inhibited and treated endothelial cells are produced; and c) observing inhibition of cell migration by the treated endothelial cells.

The present invention also provides methods of inhibiting angiogenesis in a subject, comprising: a) providing a subject comprising a tissue and an agent which inhibits specific binding of integrin α4β1 to an integrin α4β1 ligand; b) administering the agent to the subject under conditions such that specific binding of integrin α4β1 to the integrin α4β1 ligand in the tissue is inhibited and a treated tissue is produced; c) observing inhibition of angiogenesis in the treated tissue. In one embodiment, the subject has a pathological condition associated with angiogenesis in the tissue. In a preferred embodiment, the tissue comprises ocular tissue, skin tissue, bone tissue, or synovial tissue. In a more preferred embodiment, the ocular tissue is selected from retina, macula, cornea, choroids, and vitreous humor. In another preferred embodiment, the tissue comprises a tumor. In a more preferred embodiment, the tumor is malignant. In a yet more preferred embodiment, the malignant tumor is metastatic. In an alternative preferred embodiment, the malignant tumor is selected form lung cancer, breast cancer, prostate cancer, cervical cancer, pancreatic cancer, colon cancer, ovarian cancer; stomach cancer, esophagus cancer, mouth cancer, tongue cancer, gum cancer, skin cancer, muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer, joint cancer, glioblastoma, lymphoma, leukemia, osteosarcoma, and Kaposi's sarcoma. In another embodiment, the agent comprises a peptide. In another embodiment, the agent comprises an antibody. In a preferred embodiment, the antibody is an anti-integrin α4β1 antibody. In another preferred embodiment, the antibody is an anti-vascular cell adhesion molecule antibody. In yet another preferred embodiment, the antibody is an anti-fibronectin antibody. In an alternative embodiment, the agent comprises an antisense sequence. In a preferred embodiment, the antisense sequence is an integrin α4β1 antisense sequence. In another preferred embodiment, the antisense sequence is a vascular cell adhesion molecule antisense sequence. In yet another preferred embodiment, the antisense sequence is a fibronectin antisense sequence. In another embodiment, the agent comprises a ribozyme. In a preferred embodiment, the ribozyme is an integrin α4β1 ribozyme. In an alternative embodiment, the ribozyme is a vascular cell adhesion molecule ribozyme. In a further embodiment, the ribozyme is a fibronectin ribozyme. In another embodiment, the ligand is vascular cell adhesion molecule. In an alternative embodiment, the ligand is fibronectin. In an alternative embodiment, the treatment reduces the severity of the pathological condition. In another alternative embodiment, the subject has angiogenesis in the tissue. In a further alternative embodiment, the subject is suspected of being capable of developing angiogenesis in the tissue. In another embodiment, the subject is human. In a further embodiment, the administering is selected from oral, intranasal, parenteral, and topical. In a further embodiment, the tissue is a tumor, and the administering is into the tumor. In yet another embodiment, the tissue is ocular. In a more preferred embodiment, the pathological condition is selected from diabetic retinopathy and macular degeneration by neovascularization. In an alternative preferred embodiment, the administering is selected from intravenous, oral, and topical. In another embodiment, the tissue is selected from bone tissue and synovial tissue. In a preferred embodiment, the pathological condition is selected from rheumatoid arthritis and osteoarthritis. In an alternative preferred embodiment, the administering is intrasynovial. In yet another embodiment, the tissue is skin tissue. In a j preferred embodiment, the pathological condition is selected from psoriasis and skin cancer. In an alternative preferred embodiment, the administering is selected from intravenous, oral, and topical.

The invention additionally provides methods for detecting angiogenesis in a tissue, comprising: a) providing a tissue and an agent capable of specifically binding to a molecule selected from integrin α4β1 polypeptide and integrin α4β1 mRNA; b) treating the tissue with the agent under conditions such that the agent specifically binds to the molecule to produce a treated tissue; and c) detecting the specific binding of the molecule to the agent in the treated tissue, thereby detecting angiogenesis in the tissue. In one embodiment, the method further comprises d) diagnosing a pathological condition characterized by angiogenesis in the tissue. In an alternative embodiment, the agent comprises a peptide. In another embodiment, the agent comprises an antibody. In a preferred embodiment, the antibody is an anti-integrin α4β1 antibody. In another preferred embodiment, the antibody is an anti-vascular cell adhesion molecule antibody. In yet another preferred embodiment, the antibody is an anti-fibronectin antibody. In yet another embodiment, the agent comprises an antisense sequence. In one preferred embodiment, the antisense sequence is an integrin α4β1 antisense sequence. In another preferred embodiment, the antisense sequence is a vascular cell adhesion molecule antisense sequence. In yet another preferred embodiment, the antisense sequence is a fibronectin antisense sequence. In an alternative embodiment, the agent comprises a ribozyme. In one preferred embodiment, the ribozyme is an integrin α4β1 ribozyme. In another preferred embodiment, the ribozyme is a vascular cell adhesion molecule ribozyme. In yet another preferred embodiment, the ribozyme is a fibronectin ribozyme.

Also provided herein are methods for screening test compounds, comprising: a) providing endothelial cells and a test compound; b) treating the endothelial cells with the compound to produce treated endothelial cells; and c) detecting inhibition of binding of integrin α4β1 to an integrin α4β1 ligand in the treated endothelial cells; and d) identifying the test compound as inhibiting angiogenesis. In one embodiment, the treating is in vivo. In another embodiment, the treating is in vitro. In a further embodiment, the endothelial cells are in a tissue exhibiting angiogenesis, and instead of steps c) and d), the method comprises c) detecting inhibition of angiogenesis in the tissue; and d) identifying the test compound as inhibiting angiogenesis. In yet another embodiment, the endothelial cells are in tumor tissue, and instead of steps c) and d), the method comprises c) detecting a reduction in the tumor tissue; and d) identifying the test compound as anti-tumorigenic. In a further embodiment, instead of steps c) and d), the method comprises c) detecting inhibition of endothelial cell adhesion in the treated endothelial cells; and d) identifying the test compound as inhibiting endothelial cell adhesion to integrin α4β1 ligand. In yet another embodiment, instead of steps c) and d), the method comprises c) detecting inhibition of endothelial cell migration in the treated endothelial cells; and d) identifying the test compound as inhibiting endothelial cell migration to integrin α4β1 ligand.

The invention additionally provides methods for isolating endothelial progenitor cells from a tissue, comprising: a) providing a tissue comprising endothelial progenitor cells and an antibody which specifically binds to integrin α4β1 polypeptide; b) treating the tissue with the agent under conditions such that the agent binds to the endothelial progenitor cells to produce treated endothelial progenitor cells; c) isolating the treated endothelial progenitor cells from the tissue.

Also provided by the invention are methods for inhibiting angiogenesis in a benign tumor, comprising: a) providing: a benign tumor (e.g., hemangioma, glioma, and teratoma); and an agent which inhibits specific binding of integrin α4β1 to an integrin α4β1 ligand; b) treating the tumor with the agent under conditions such that specific binding of integrin α4β1 to the integrin α4β1 ligand is inhibited and a treated tumor is produced; and c) observing inhibition of angiogenesis in the treated tumor.

The invention further provides methods for inhibiting angiogenesis in a cancer tissue, comprising: a) providing cancer tissue and an agent which inhibits specific binding of integrin α4β1 to an integrin α4β1 ligand; b) treating the cancer tissue with the agent under conditions such that specific binding of integrin α4β1 to the integrin α4β1 ligand is inhibited and a treated cancer tissue is produced; and c) observing inhibition of angiogenesis in the treated cancer tissue. In one embodiment, the cancer is selected from lung cancer, breast cancer, prostate cancer, cervical cancer, pancreatic cancer, colon cancer, ovarian cancer; stomach cancer, esophagus cancer, mouth cancer, tongue cancer, gum cancer, skin cancer, muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer, joint cancer, glioblastoma, lymphoma, leukemia, osteosarcoma, and Kaposi's sarcoma. In another embodiment, the cancer comprises a cell selected from hyperplastic cells, dysplastic cells, and neoplastic cells. In a further embodiment, the cancer is metastatic.

Also provided by the invention are methods for inhibiting angiogenesis in ocular tissue, comprising: a) providing ocular tissue and an agent which inhibits specific binding of integrin α4β1 to an integrin α4β1 ligand; b) treating the ocular tissue with the agent under conditions such that specific binding of integrin α4β1 to the integrin α4β1 ligand is inhibited and a treated ocular tissue is produced; and c) observing inhibition of angiogenesis in the treated ocular tissue. In one embodiment, the ocular tissue is selected from retina, macula, cornea, choroid, and vitreous humor. In another embodiment, the ocular tissue comprises a cancer.

The invention additionally provides methods for inhibiting angiogenesis in skin tissue, comprising: a) providing skin tissue and an agent which inhibits specific binding of integrin α4β1 to an integrin α4β1 ligand; b) treating the skin tissue with the agent under conditions such that specific binding of integrin α4β1 to the integrin α4β1 ligand is inhibited and a treated skin tissue is produced; and c) observing inhibition of angiogenesis in the treated skin tissue. In one embodiment, the skin tissue comprises a cancer. In another embodiment, the skin tissue is injured. In an alternative embodiment, the skin tissue comprises a pathological condition selected from psoriasis, hemangioma, and gingivitis.

The invention further provides methods for reducing symptoms associated with cancer in a subject, comprising: a) providing a subject having cancer tissue; and an agent which inhibits specific binding of integrin α4β1 to an integrin α4β1 ligand; b) treating the subject with the agent under conditions such that specific binding of integrin α4β1 to the integrin α4β1 ligand is inhibited in the cancer tissue, and a treated cancer tissue is produced; and c) observing a reduction in one or more symptoms associated with the cancer tissue.

The invention also provides methods for reducing symptoms associated with a pathological condition in ocular tissue, comprising: a) providing: i) a subject having a pathological condition in ocular tissue; ii) an agent which inhibits specific binding of integrin α4β1 to an integrin α4β1 ligand; b) treating the subject with the agent under conditions such that specific binding of integrin α4β1 to the integrin α4β1 ligand is inhibited in the ocular tissue, and a treated ocular tissue is produced; and c) observing a reduction in one or more symptoms associated with the pathological condition in the ocular tissue.

Further provided by the invention are methods for reducing symptoms associated with a pathological condition in skin tissue, comprising: a) providing a subject having a pathological condition in skin tissue, and an agent which inhibits specific binding of integrin α4β1 to an integrin α4β1 ligand; b) treating the subject with the agent under conditions such that specific binding of integrin α4β1 to the integrin α4β1 ligand is inhibited in the skin tissue, and a treated skin tissue is produced; and c) observing reduction in one or more symptoms associated with the pathological condition in the treated skin tissue.

BRIEF DESCRIPTION OF THE DRAWINGS

FIG. 1 shows inhibition of angiogenesis using (A) antibody against fibronectin C-terminus (Anti-CT) in a chick CAM model and (B) monoclonal antibody directed against the C-terminal CS-1 or heparin binding regions of fibronectin.

FIG. 3 shows inhibition of endothelial cell adhesion (A), and migration (B) by anti-integrin α4 antibody antagonists.

FIG. 5 shows inhibition of murine angiogenesis by antibody (A) and peptide antagonists (B) of integrin α4β1.

FIG. 6 shows the polypeptide sequence (SEQ ID NO:1) of the human α4 subunit, GenBank Accession No. XP_039012.1.

FIG. 7 shows the polypeptide sequence (SEQ ID NO:2) of the human β1 subunit, GenBank Accession No. P05556.

FIG. 8 shows the polypeptide sequence of the human vascular cell adhesion molecule (VCAM), GenBank Accession Nos. P19320 (SEQ ID NO:3) (A) and XP_035774 (SEQ ID NO:96) (B).

FIG. 9 shows the polypeptide sequence (SEQ ID NO:4) of human fibronectin, GenBank Accession No. PO2751.

FIG. 13 shows the cDNA sequence (SEQ ID NO:5) of the human integrin α4 subunit cDNA, GenBank Accession No. XM_039012.

FIG. 14 shows the cDNA sequence (SEQ ID NO:6) of the human integrin α4 subunit, GenBank Accession No. XM_039012.

FIG. 15 shows the cDNA sequence (SEQ ID NO:7) of the human integrin β1 subunit, GenBank Accession No. X07979.

FIG. 16 shows the human VCAM cDNA sequence (SEQ ID NO:8), GenBank Accession No. X53051.

FIG. 17 shows the sequence of human fibronectin cDNA (SEQ ID NO:9), GenBank Accession No. X02761.

FIG. 22 shows a graph of average tumor size in cubic millimeters versus days of measurement (Panel A) and a graph of tumor mass versus treatment with anti-α4β1.

DESCRIPTION OF THE INVENTION

Figure 2:
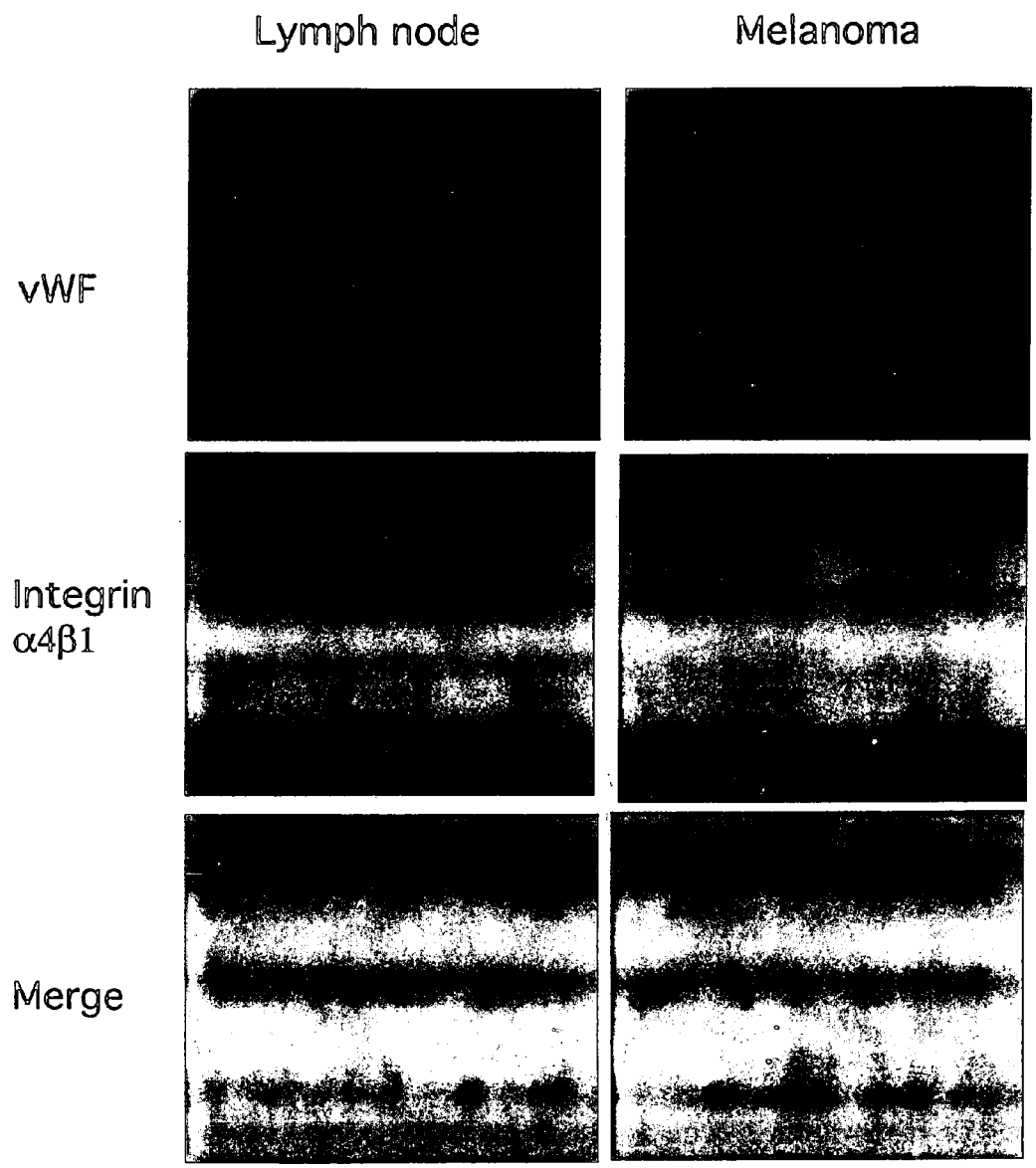
FIG. 2 shows an immunohistochemical analysis of integrin α4β1 expression in normal and tumor blood vessels.

The invention provides methods for detecting and inhibiting angiogenesis, endothelial cell adhesion, and endothelial cell migration using agents which inhibit the specific binding of integrin α4β1 to one or more of its ligands. The invention further provides methods for screening test compounds for their ability to inhibit angiogenesis, endothelial cell adhesion, or endothelial cell migration by employing agents which inhibit the specific binding of integrin α4β1 to one or more of its ligands. The invention additionally relates to methods for isolating endothelial cells which express integrin α4β1. The methods of the invention are useful in, for example, diagnosing and inhibiting pathological conditions that are associated with angiogenesis, endothelial cell adhesion, and/or endothelial cell migration. The methods of the present invention are also useful in isolating endothelial progenitor cells, and in determining the mechanisms that underlie angiogenesis, development, wound healing, and the function of the female reproductive system.

The methods of the invention are based, in part, on the inventor's fortuitous discovery that integrin α4β1 plays a role in the angiogenic process, including endothelial cell migration and endothelial cell adhesion. The methods provided herein also are based on the inventors' discovery that angiogenesis, endothelial cell migration and endothelial cell adhesion are inhibited by inhibiting the specific binding of integrin α4β1 to one or more of its ligands.

The invention is further discussed below under the headings: (A) Inhibiting Angiogenesis, (B) Inhibiting Endothelial Cell Adhesion And Endothelial Cell Migration, (C) Detecting Angiogenesis, (D) Screening Compounds, and (E) Isolating Endothelial Cell Progenitors.

A. Inhibiting Angiogenesis

Angiogenesis, or neovascularization, is the process by which new blood vessels develop from pre-existing vessels [Varner et al. (1999) Angiogen. 3(1):53-60; Mousa et al. (2000) Angiogen. Stim. & Inhib. 35-42; 44. Kim et al. (2000) Amer. J. Path. 156:1345-1362; Kim et al. (2000) J. Biol. Chem. 275:33920-33928; Kumar et al. (2000) Angiogenesis: From Molecular to Integrative Pharm. 169-180]. Endothelial cells from pre-existing blood vessels or from circulating endothelial stem cells [Takahashi et al. (1995) Nat. Med. 5:434-438; Isner et al. (1999) J. Clin. Invest. 103:1231-1236] become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation.

The invention provides methods for inhibiting angiogenesis in a tissue that involve treating the tissue with an agent which inhibits the specific binding of integrin α4β1 to one or more of its ligands. The methods of the invention are useful in, for example, determining the mechanisms which underlie desirable angiogenesis in processes such as development, wound healing, and the function of the female reproductive system. The methods of the present invention are also useful in preventing and inhibiting undesirable angiogenesis in normal angiogenesis processes in a subject, such as scar formation during wound healing or fertility. These methods also find use in inhibiting undesirable angiogenesis which occurs in ocular tissue, skin, synovial tissue, bone, or intestinal tissue, by inhibiting the binding of α4β1 binding to one or more of its ligands (e.g., fibronectin and VCAM) in the tissue. In addition, the methods of the invention are useful for reducing or inhibiting angiogenesis in a neoplasm, which can be benign or malignant and, where malignant, can be a metastatic neoplasm. Preferably, inhibiting angiogenesis results in reducing the severity of the pathological condition that is associated with angiogenesis.

Without limiting the invention to any particular mechanism, and while recognizing that an understanding of the mechanism of the invention is not required, it is contemplated that agents which inhibit the specific binding of integrin α4β1 to one or more of its ligands block the outgrowth of new blood vessels from pre-existing vessels, and/or block the ability of circulating endothelial cells and/or progenitor endothelial cells from leaving the bloodstream and entering and migrating through tissues to sites of hypoxia or growth factor secretion where they may participate in the formation of new blood vessels.

As used herein, the term "tissue exhibiting angiogenesis" refers to a tissue in which new blood vessels are developing from pre-existing blood vessels.

As used herein, the term "inhibiting angiogenesis," "diminishing angiogenesis," "reducing angiogenesis," and grammatical equivalents thereof refer to reducing the level of angiogenesis in a tissue to a quantity which is preferably 10% less than, more preferably 50% less than, yet more preferably 75% than, even more preferably 90% less than, the quantity in a corresponding control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis.

The level of angiogenesis may be determined using methods well known in the art, including, without limitation, counting the number of blood vessels and/or the number of blood vessel branch points, as discussed herein. An alternative assay involves an in vitro cell adhesion assay that shows whether a compound inhibits the ability of α4β1-expressing cells (e.g. M21 melanoma cells) to adhere to VCAM or fibronectin. Another in vitro assay contemplated includes the tubular cord formation assay that shows growth of new blood vessels at the cellular level [D. S. Grant et al., Cell, 58: 933-943 (1989)]. Art-accepted in vivo assays are also known, and involve the use of various test animals such as chickens, rats, mice, rabbits and the like. These in vivo assays include the chicken chorioallantoic membrane (CAM) assay, which is suitable for showing anti-angiogenic activity in both normal and neoplastic tissues [D. H. Ausprunk, Amer. J. Path., 79, No. 3: 597-610 (1975) and L. Ossonowski and E. Reich, Cancer Res., 30: 2300-2309 (1980)]. Other in vivo assays include the mouse metastasis assay, which shows the ability of a compound to reduce the rate of growth of transplanted tumors in certain mice, or to inhibit the formation of tumors or preneoplastic cells in mice which are predisposed to cancer or which express chemically-induced cancer [M. J. Humphries et al., Science, 233: 467-470 (1986) and M. J. Humphries et al., J. Clin. Invest., 81: 782-790 (1988)].

As discussed herein, data obtained during the development of the present invention demonstrate that angiogenesis is inhibited in vivo when using antibodies to the C-terminus of fibronectin in the chick chorioallantoic membrane (CAM) assay (Example 1), antibodies to integrin α4β1 in the CAM assay and by intravenous injection into chicks (Example 4), and antibodies and peptide antagonists to integrin α4β1 which were applied subcutaneously in a mouse model (Example 5).

While the invention is illustrated using antibodies to the C-terminus of fibronectin and to integrin α4β1, and using exemplary peptide antagonists to integrin α4β1, the invention is not limited to the use of these particular agents. Rather, the invention expressly includes any agent which inhibits the specific binding of integrin α4β1 to one or more integrin α4β1 ligands.

The term "integrin α4β1" is interchangeably used with the terms "CD49d/CD29," "very late antigen 4," and "VLA4" to refer to a member of the family of integrins. An "integrin" is an extracellular receptor that is expressed in a wide variety of cells and binds to specific ligands in the extracellular matrix. The specific ligands bound by integrins can contain an arginine-glycine-aspartic acid tripeptide (Arg-Gly-Asp; RGD) or a leucine-aspartic acid-valine (Leu-Asp-Val) tripeptide, and include, for example, fibronectin, vitronectin, osteopontin, tenascin, and von Willebrands's factor. Integrin α4β1 is a heterodimeric cell surface adhesion receptor composed of an α4 and β1 subunits that bind to ligands which are present in the extracellular matrix (ECM) as well as on the cell surface. An exemplary α4 polypeptide sequence is shown in FIG. 6, and an exemplary β1 polypeptide sequence is shown in FIG. 7.

The term "integrin α4β1" is contemplated also to include a portion of α4β1. The term "portion," when used in reference to a protein (as in a "portion of α4β1") refers to a fragment of that protein. The fragments may range in size from three (3) contiguous amino acid residues to the entire amino acid sequence minus one amino acid residue. Thus, a polypeptide sequence comprising "at least a portion of an amino acid sequence" comprises from three (3) contiguous amino acid residues of the amino acid sequence to the entire amino acid sequence.

In one preferred embodiment, the portion of integrin α4β1 comprises a portion of the α4 polypeptide sequence. In a more preferred embodiment, the portion of the α4 polypeptide sequence shown in FIG. 6 comprises the sequence IVTCGH-RWKNIFYIKNENKLPTGGCYGVPPDLR-TELSKRIAPCYQDYVKKFGENFA SCQAGISSFYT-KDLIVMGAPGSSYWTGSLFVYNITTNKYKAFLD KQNQVKFGSYLG YSVGAGHFRSQHTTEVVG-GAPQHEQIGKAYIFSIDEKELNILHEMKGKK (SEQ ID NO:10) (from amino acid 141 to amino acid 301). In a more preferred embodiment, the portion of integrin α4β1 comprises the sequence GHRWKN IFYIKNENKLPTGG (SEQ ID NO:11) (from amino acid 145 to amino acid 164), the sequence YQDYVKKFGENFAS (SEQ ID NO:12) (from amino acid 184 to amino acid 197), the sequence SYWTGS (SEQ ID NO:13) (from amino acid 219 to amino acid 224), the sequence GGAPQHEQIGK (SEQ ID NO:14) (from amino acid 270 to amino acid 280), and the sequence YNVDTES ALLYQGPHNT IFGYSVVLHS HGANR-WLLVG APTANWLANA SVINP (SEQ ID NO:54) (from amino acid 34 to amino acid 85). In an alternative embodiment, the invention expressly includes portions of the α4 polypeptide sequence (which is exemplified by the sequence of FIG. 6) that contain the fore-mentioned portions. Such sequences include, for example,

```
GRPYNVDTESALLYQGPHNTLFGYSVVLHSHGAN  (SEQ ID NO: 55)

RWLLVGAPTANWLANASVINPGAIYR,

GVPTGRPYNVDTESALLYQGPHNT LFGYSVVLH  (SEQ ID NO: 56)

SHGANRWLLVGAPTANWLANASVINPGAIYRCRI

GKNPGQT,

IVTCGHRWKNIFYIKNENKLPTGGCYG,        (SEQ ID NO: 57)

GHRWKNIFYIKNENKLPTGGCYGVPPDLRTELS   (SEQ ID NO: 58)
K,

APCYQKYVKKFGENFAS,                  (SEQ ID NO: 59)

CYQKYVKKFGENFASCQAGISSFYTKDL,       (SEQ ID NO: 60)

GSSYWTGSLFVYNI,                     (SEQ ID NO: 61)

RSQHTTEVVGGAPQHEQIGK,               (SEQ ID NO: 62)

GGAPQHEQIGKAYIFSIDEKEL,             (SEQ ID NO: 63)
and/or

GGAPQHEQIGKA.                       (SEQ ID NO: 64)
``` i. Integrin α4β1 Ligands

The methods of the invention employ agents which inhibit the specific binding of integrin α4β1 with one or more of its ligands. The term "ligand" as used herein in reference to a ligand for the integrin α4β1 receptor, refers to a molecule, or portion thereof, to which α4β1 specifically binds, thereby initiating a specific biological response (e.g., endothelial cell migration, endothelial cell adhesion, angiogenesis, etc.) or the transduction of a signal in a cell. Integrin α4β1 ligands may be present on the cell surface or present in the extracellular matrix (ECM).

In one preferred embodiment, an integrin α4β1 ligand that is present on the cell surface is exemplified by the vascular cell adhesion molecule (VCAM). An example of the polypeptide sequence of VCAM is shown in FIG. 8. In another preferred embodiment, the integrin α4β1 ligand is a portion of VCAM. Preferred portions of VCAM (FIG. 8A, GenBank Accession Nos. P19320) comprise the amino acid sequence RTQIDSPLNG (SEQ ID NO:15) (from amino acid 60 to amino acid 69); the amino acid sequence RTQIDSPLSG (SEQ ID NO:16) (from amino acid 348 to amino acid 357); and the amino acid sequence KLEK (SEQ ID NO:17) (from amino acid 103 to amino acid 106, and from amino acid 391 to amino acid 394). Other portions of VCAM are also contemplated, which preferably contain one of more of the RTQIDSPLNG (SEQ ID NO:15), RTQIDSPLSG (SEQ ID NO:16), or KLEK (SEQ ID NO:17) sequences. These are exemplified by, but not limited to, WRTQIDSPLNGK (SEQ ID NO:65), SWRTQIDSPLNGKV (SEQ ID NO:66), SWRTQIDSPLNGKVT (SEQ ID NO:67), PFFSWRTQIDSPLNGKVTNE (SEQ ID NO:68), SRKLEKGI (SEQ ID NO:69), CESRKLEKGIQV (SEQ ID NO:70), ATCESRKLEKGIQVEI (SEQ ID NO:71), LCTATCESRKLEKGIQVEIYSFPKDPE (SEQ ID NO:72), GHKKLEKGIQVEL (SEQ ID NO:73), VTCGHKKLEKGI (SEQ ID NO:74), TCGHKKLEKGIQVELYSFPRDPE (SEQ ID NO:75), PVSFENEHSYLCTVTCGHKKLEKG (SEQ ID NO:76), RTQIDSPLSGK (SEQ ID NO:77), FSWRTQIDSPLSGKVR (SEQ ID NO:78), and/or ESPSFWWRTQIDSPLSGK (SEQ ID NO:79).

In another preferred embodiment, an integrin α4β1 ligand that is present in the ECM is exemplified by fibronectin. An exemplary polypeptide sequence of fibronectin is shown in FIG. 9. In another preferred embodiment, the integrin α4β1 ligand is a portion of fibronectin. Preferred portions of fibronectin as exemplified in FIG. 9 include the IIICS sequence (SEPLIGRKKTDELPQLVTLPHPNLHGPE ILDVPSTVQKTPFVTHPGYDTGNGIQLPGTS-GQQPSVGQQMIFEEHGFRRTTPPTTA TPIRHRPRPYP-PNVGEEIQIGHIPREDVDYHLYPHGPGLNPNAST) (SEQ ID NO:18) from amino acid 1982 to amino acid 2111, which encodes two α4β1 binding sites. In one more preferred embodiment, the portion comprises the CS-1 sequence which contains the amino acid sequence LDV (SEQ ID NO:19) (from amino acid 2011 to amino acid 2013). In an alternative embodiment, the portion comprises the CS-5 sequence which contains the amino acid sequence REDV (SEQ ID NO:20) (from amino acid 2091 to amino acid 2094). In yet another preferred embodiment, the portion comprises the amino acid sequence IDAPS (SEQ ID NO:21) (from amino acid 1903 to amino acid 1907). The invention further includes portions of fibronectin that contain the fore-mentioned sequences, as exemplified by, but not limited to, the sequences TAIDAPSNLRDAS (SEQ ID NO:80), TAIDAPSNLRFLATTP (SEQ ID NO:81), RSSPVVIDASTAIDAPS (SEQ ID NO:82), IDAPSNLRFLATTPNSLLV (SEQ ID NO:83), IDAPSNLRFLATTPNSLLVSWQPPRARITGYIIKYE (SEQ ID NO:84), IDDVPST (SEQ ID NO:85), NLHGPEILDVPSTVQK (SEQ ID NO:86), PHPNLHGPEILDV (SEQ ID NO:87), ILDVPSTVQKTPFVTHPGYD (SEQ ID NO:88), VTLPHPNLHGPEILDVP (SEQ ID NO:89), EILDV (SEQ ID NO:90), IPREDVDY (SEQ ID NO:91), GHIPRDDVD (SEQ ID NO:92), GHIPREDV (SEQ ID NO:93), LDVPSTVQKTPFVTHPGYDTGNGIQLPGTS-GQQPSVGQQMIFEEHG FRRTTPPTTATPIRHRPRPYP-PNVGEEIQIGHIPREDV (SEQ ID NO:94), and/or PEILDVPSTVQKTPFVTHPGYDT-GNGIQLPGTSGQQPSVGQQMIFEEHGFRRTTPPT TTATPIRHRPRPYPPNVGEEIQIGHIPREDVDY (SEQ ID NO:95).

Integrin α4β1 ligands other than VCAM, fibronectin, and portions thereof are also contemplated to be within the scope of the invention. These ligands may be determined using routine methods available to those skilled in the art. For example, the existence of antibodies against VCAM, fibronectin, and integrin α4β1 makes possible methods for isolating other integrin α4β1 and integrin α4β1 ligands. One method takes advantage of an antibody characteristic known as idiotypy. Each antibody contains a unique region that is specific for an antigen. This region is called the idiotype. Antibodies themselves contain antigenic determinants; the idiotype of an antibody is an antigenic determinant unique to that molecule. By immunizing an organism with antibodies, one can raise "anti-antibodies" that recognize antibodies, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen [Kennedy (1986) Sci. Am. 255:48-56]. For example, anti-idiotypic antibodies have been successfully generated against anti-ELAM1 antibodies and were found to recognize the ELAM1 ligand, which (similarly to integrin α4β1) is a molecule expressed on the surface of endothelial cells [U.S. Pat. No. 6,252,043, incorporated in its entirety by reference].

When the antigen is a ligand, certain anti-idiotypes can bind to that ligand's receptor. Several of these have been identified, including anti-idiotypes that bind to receptors for insulin, angiotensin II, adenosine I, adrenalin, and rat brain nicotine and opiate receptors [Carlsson and Glad (1989) Bio/Technology 7:567-73].

ii. Agents Which Inhibit Binding of Integrin α4β1 to its Ligands

Some preferred methods of the present invention include the step of utilizing an agent that inhibits the specific binding of α4β1 to one or more of its ligands. The term "specific binding," as used herein in reference to the binding of an agent to either integrin α4β1 or an integrin α4β1 ligand, means that the interaction is dependent upon the presence of a particular structure on integrin α4β1 or its ligand, respectively. For example, if an agent is specific for epitope "A," the presence of a protein containing epitope A (or free, unlabelled A) in a reaction containing labeled "A" and the agent will reduce the amount of labeled A bound to the agent.

The terms "inhibit the specific binding" and "reduce the specific binding" when used in reference to the effect of an agent on the specific binding of integrin α4β1 with an integrin α4β1 ligand, mean that the agent reduces the level of specific binding of integrin α4β1 with its ligand to a quantity which is preferably 10% less than, more preferably 50% less than, yet more preferably 75% less than, even more preferably 90% less than, the quantity of specific binding in a corresponding control sample, and most preferably is at the same level which is observed in a control sample, as detected by (for example) an Enzyme Linked Immunosorbant Assay (ELISA). A reduced level of specific binding need not, although it may, mean an absolute absence of specific binding. The invention does not require, and is not limited to, methods that wholly eliminate specific binding of integrin α4β1 with its ligand.

The terms "agent" and "antagonist" are used herein to mean a molecule, (e.g., antibody) which can inhibit the specific binding of a receptor and its ligand. For example, an anti-α4β1 integrin antibody, which inhibits the specific binding of α4β1 with fibronectin, is an example of an α4β1 antagonist. An antagonist can act as a competitive inhibitor or a noncompetitive inhibitor of α4β1 binding to its ligand.

Without intending to limit the invention to any mechanism, and recognizing that an understanding of a mechanism is not required, it is contemplated that an agent can inhibit the specific binding of an integrin α4β1 receptor with its ligand by various mechanisms, including, for example, by binding to the binding site which is located on the ligand (e.g., VCAM) thereby inhibiting the binding of the integrin α4β1 receptor to its binding site on the ligand, or by binding to a site other than the binding site on the ligand and sterically hindering the binding of the integrin α4β1 receptor to the binding site on the ligand. Alternatively, the agent may bind to integrin α4β1 (rather than to the integrin α4β1 ligand) thereby causing a conformational or other change in the receptor that inhibits binding of integrin α4β1 to the ligand.

1. Antibodies

In one embodiment, the agent that inhibits the specific binding of α4β1 to one or more of its ligands is an antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" expressly includes within its scope antigen binding fragments of such antibodies, including, for example, Fab, F(ab')$_2$, Fd or Fv fragments of an antibody. The antibodies of the invention also include chimeric and humanized antibodies. Antibodies may be polyclonal or monoclonal. The term "polyclonal antibody" refers to an immunoglobulin produced from more than a single clone of plasma cells; in contrast "monoclonal antibody" refers to an immunoglobulin produced from a single clone of plasma cells.

Antibodies contemplated to be within the scope of the invention include naturally occurring antibodies as well as non-naturally occurring antibodies, including, for example, single chain antibodies, chimeric, bifunctional and humanized antibodies, as well as antigen-binding fragments thereof. Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described [Huse et al., Science 246:1275-1281 (1989)]. These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Hilyard et al., Protein Engineering: A practical approach (IRL Press 1992); and Borrabeck, Antibody Engineering, 2d ed. (Oxford University Press 1995).

As used herein, the term "antibody" when used in reference to an anti-integrin antibody, particularly an anti-integrin α4β1 antibody, refers to an antibody which specifically binds to one or more epitopes on an integrin α4β1 polypeptide or peptide portion thereof, and which may or may not include some or all of an RGD binding domain. In one embodiment, an anti-integrin α4β1 antibody, or antigen binding fragment thereof, is characterized by having specific binding activity for integrin α4β1 of at least about $1 \times 10^5 M^{-1}$, more preferably at least about $1 \times 10^6 M^{-1}$, and yet more preferably at least about $1 \times 10^7 M^{-1}$.

Those skilled in the art know how to make polyclonal and monoclonal antibodies that are specific to a desirable polypeptide. For example, monoclonal antibodies may be generated by immunizing an animal (e.g., mouse, rabbit, etc.) with a desired antigen and the spleen cells from the immunized animal are immortalized, commonly by fusion with a myeloma cell.

Immunization with antigen may be accomplished in the presence or absence of an adjuvant (e.g., Freund's adjuvant). Typically, for a mouse, 10 µg antigen in 50-200 µl adjuvant or aqueous solution is administered per mouse by subcutaneous, intraperitoneal or intra-muscular routes. Booster immunization may be given at intervals (e.g., 2-8 weeks). The final boost is given approximately 2-4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted.

Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10-15% fetal calf serum. Fusion of myeloma cells and spleen cells may be accomplished using polyethylene glycol (PEG) or by electrofusion using protocols that are routine in the art. Fused cells are distributed into 96-well plates followed by selection of fused cells by culture for 1-2 weeks in 0.1 ml DMEM containing 10-15% fetal calf serum and HAT. The supernatants are screened for antibody production using methods well known in the art. Hybridoma clones from wells containing cells that produce antibody are obtained (e.g., by limiting dilution). Cloned hybridoma cells ($4-5 \times 10^6$) are implanted intraperitoneally in recipient mice, preferably of a BALB/c genetic background. Sera and ascites fluids are typically collected from mice after 10-14 days.

The invention also contemplates humanized antibodies that are specific for at least a portion of integrin α4β1 or its ligands. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

In a preferred embodiment, the antibody is specific for integrin α4β1 or a portion thereof. In a more preferred embodiment, the anti-integrin α4β1 antibody binds integrin α4β1 with at least 2 times greater, preferably at least 5 times greater, more preferably at least 10 times greater, and yet more preferably at least 100 times greater, affinity than it binds another integrin, for example, aVβ3 or aVβ5. Anti-integrin α4β1 antibodies include, without limitation, mouse anti-human integrin α4β1 antibodies such as HP2/1, HP1/3, HP 1/1, HP1/7, HP2/4 [Sanchez-Madrid et al. (1986) Eur. J. Immunol. 16, 1342-1349], ALC1/4.1, ALC1/5.1 [Munoz et al. (1997) Biochem J., 327, 27-733], 44H6 [Quackenbush et al. (1985) J. Immunol. 134: 1276-1285], P1H4, P4C2, P4G9 [Wayner et al. (1998) J. Cell Biol. 109:1321], 9C10 [Kinashi et al. (1994) Blood Cells 20: 25-44)], 9F10 [Hemler et al. (1987) J. Biol. Chem. 262: 11478], BSG10 [Hemler et al. (1987) J. Biol. Chem. 262, 3300-3309], 15/7 [Yednock et al. (1995) J. Biol. Chem. 270:28740-28750], SG/73 [Miyake et al. (1992) J. Cell Biol., 119, 653-662]. Also included within the scope of this invention are humanized anti-human integrin α4β1 antibodies, such as "ANTEGREN™" (also known as natalizumab) [Tubridy et al. (1999) Neurology 53(3):466-72, Sheremata et al. (1999) Neurology 52: No.5, Mar. 23, 1999, and Lin et al. (1998) Current Opinion in Chemical Biology 2:453-457] and the chimeric antibodies disclosed by Newman et al., U.S. Pat. No. 5,750,105, the contents of which are incorporated by reference; rat anti-mouse integrin α4β1 antibodies such as PS/2 [Chisholm et al. (1993) European J. Immunol 23: 682-688]; mouse anti-rat α4β1 antibodies such as TA-2 [Issekutz (1991) J. Immunol 147:4178-4184]; and rat anti-mouse α4β1 antibodies such as R1-2 [Holzmann et al. (1989) Cell 56: 37-46].

In another preferred embodiment, the antibody is specific for VCAM or a portion thereof. In a more preferred embodiment, the anti-VCAM antibody inhibits the binding of VCAM to α4β1 integrin but not to other integrins. Exemplary antibodies include, for example, 4B2 and 1E10, P1B8, and P3C4 [Needham et al. (1994) Cell Adhes. Commun. 2:87-99; Dittel et al. (1993) Blood 81:2272-2282], and the chimeric antibodies disclosed by Newman et al., U.S. Pat. No. 5,750, 105, the contents of which are incorporated by reference.

In yet another preferred embodiment, the antibody is specific for fibronectin or a portion thereof. In a more preferred embodiment, the anti-VCAM antibody inhibits the binding of VCAM to α4β1 integrin but not to other integrins. Such antibodies include, without restriction, antibodies against the major and minor integrin α4β1-binding sites in the C-terminal region of fibronectin, and antibodies against neighboring heparin binding sites that interfere with binding of integrin α4β1 to fibronectin. Exemplary antibodies include P1F11 and P3D4 [Garcia-Pardo et al. (1992) Biochemical and Biophysical Research Communications 186(1):135-42]; and the antibodies 20E10, 21E5, 9E9, 16E6, 19B7, 26G10, 30B6, 36C9, and 39B6 [Mostafavi-Pour et al. (2001) Matrix Biology 20(1):63-73].

2. Peptides

In an alternative embodiment, the agent which inhibits the specific binding of integrin α4β1 to one or more of its ligands is a peptide. Data provided herein show that the exemplary peptide EILDVPST (SEQ ID NO:22) inhibits integrin α4β1 binding to its ligand resulting in inhibition of angiogenesis (Example 5). The term "peptide" as used herein is used broadly to refer to at least two amino acids or amino acid analogs that are covalently linked by a peptide bond or an analog of a peptide bond. The term peptide includes oligomers and polymers of amino acids or amino acid analogs. The term peptide also includes molecules which are commonly referred to as peptides, which generally contain from about two to about twenty amino acids. The term peptide also includes molecules which are commonly referred to as polypeptides, which generally contain from about twenty to about fifty amino acids. The term peptide also includes molecules which are commonly referred to as proteins, which generally contain from about fifty to about 3000 amino acids. The amino acids of the peptide antagonists may be L-amino acids or D-amino acids.

The terms "derivative" or "modified" when in reference to a peptide mean that the peptide contains at least one derivative amino acid. A "derivative" of an amino acid and a "modified" amino acid are chemically modified amino acids. Derivative amino acids can be "biological" or "non-biological" amino acids. Chemical derivatives of one or more amino acid members may be achieved by reaction with a functional side group. Illustrative derivatized molecules include for example those molecules in which free amino groups have been derivatized to form amine hydrochlorides, p-toluene sulfonyl groups, carboxybenzoxy groups, t-butyloxycarbonyl groups, chloroacetyl groups or formyl groups. Free carboxyl groups may be derivatized to form salts, methyl and ethyl esters or other types of esters and hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides that contain naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine for lysine. Other included modifications are amino terminal acylation (e.g., acetylation or thioglycolic acid amidation), terminal carboxylamidation (e.g., with ammonia or methylamine), and similar terminal modifications. Terminal modifications are useful, as is well known, to reduce susceptibility by proteinase digestion and therefore to prolong the half-life of the peptides in solutions, particularly in biological fluids where proteases may be present. Exemplary modified amino acids include, without limitation, 2-Aminoadipic acid, 3-Aminoadipic acid, beta- Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylgilycine, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, N-Methylavaline, Norvaline, Norleucine, and Ornithine. Derivatives also include peptides containing one or more additions or deletions, as long as the requisite activity is maintained.

The amino acids of the peptides are contemplated to include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids.

Peptides that are useful in the instant invention may be synthesized by several methods, including chemical synthesis and recombinant DNA techniques. Synthetic chemistry techniques, such as solid phase Merrifield synthesis are preferred for reasons of purity, freedom from undesired side products, ease of production, etc. A summary of the techniques available are found in several references, including Steward et. al., Solid Phase Peptide Synthesis, W. H. Freeman, Co., San Francisco (1969); Bodanszky, et. al., Peptide Synthesis, John Wiley and Sons, Second Edition (1976); J. Meienhofer, Hormonal Proteins and Peptides, 2: 46, Academic Press (1983); Merrifield, Adv. Enzymol. 32: 221-96 (1969); Fields, et. al., Intl. Peptide Protein Res., 35: 161-214 (1990), and U.S. Pat. No. 4,244,946 for solid phase peptide synthesis; and Schroder et al., The Peptides, Vol 1, Academic Press (New York) (1965) for classical solution synthesis. Protecting groups usable in synthesis are described as well in Protective Groups in Organic Chemistry, Plenum Press, New York (1973). Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

The resultant linear peptides may then be reacted to form their corresponding cyclic peptides. A method for cyclizing peptides is described in Zimmer et. al., Peptides, 393-394 (1992), ESCOM Science Publishers, B. V., 1993. To cyclize peptides containing two or more cysteines through the formation of disulfide bonds, the methods described by Tam et al., J. Am. Chem. Soc., 113: 6657-6662 (1991); Plaue, Int. J. Peptide Protein Res., 35: 510-517 (1990); Atherton, J. Chem. Soc. Trans. 1: 2065 (1985); and B. Kamber et. al., Helv. Chim. Acta 63: 899 (1980) are useful. Polypeptide cyclization is a useful modification to generate modified peptides (e.g., peptidomimetics) because of the stable structures formed by cyclization and in view of the biological activities observed for cyclic peptides.

Alternatively, selected compounds of the present invention are produced by expression of recombinant DNA constructs prepared in accordance with well-known methods once the peptides are known. Such production can be desirable to provide large quantities or alternative embodiments of such compounds. Production by recombinant means may be more desirable than standard solid phase peptide synthesis for peptides of at least 8 amino acid residues. The DNA encoding the desired peptide sequence is preferably prepared using commercially available nucleic acid synthesis methods. Following these nucleic acid synthesis methods, DNA is isolated in a purified form that encodes the peptides. Methods to construct expression systems for production of peptides in recombinant hosts are also generally known in the art. Preferred recombinant expression systems, when transformed into compatible hosts, are capable of expressing the DNA encoding the peptides. Other preferred methods used to produce peptides comprise culturing the recombinant host under conditions that are effective to bring about expression of the encoding DNA to produce the peptide of the invention and ultimately to recover the peptide from the culture.

Expression can be effected in either prokaryotic or eukaryotic hosts. The prokaryotes are most frequently represented by various strains of *E. coli*. However, other microbial strains may also be used, such as bacilli, for example *Bacillus subtilis*, various species of *Pseudomonas*, or other bacterial strains. In such prokaryotic systems, plasmid vectors that contain replication sites and control sequences derived from a species compatible with the host are used. For example, a workhorse vector for *E. coli* is pBR322 and its derivatives. Commonly used prokaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived P.sub.L promoter and N-gene ribosome binding site. However, any available promoter system compatible with prokaryote expression is suitable for use.

Expression systems useful in eukaryotic hosts comprise promoters derived from appropriate eukaryotic genes. A class of promoters useful in yeast, for example, includes promoters for synthesis of glycolytic enzymes (e.g., those for 3-phosphoglycerate kinase). Other yeast promoters include those from the enolase gene or the Leu2 gene obtained from YEp13. Suitable mammalian promoters include the early and late promoters from SV40 or other viral promoters such as those derived from polyoma, adenovirus II, bovine papilloma virus or avian sarcoma viruses. Suitable viral and mammalian enhancers may also be used. In the event plant cells are used as an expression system, the nopaline synthesis promoter, for example, is appropriate.

Once the expression systems are constructed using well-known restriction and ligation techniques, transformation of appropriate host cells is done using standard techniques appropriate to such cells. The cells containing the expression systems are cultured under conditions appropriate for production of the peptides, and the peptides are then recovered and purified.

In a preferred embodiment, the agent that specifically binds integrin $\alpha 4\beta 1$ finds use in methods of the invention where the peptide binds to integrin $\alpha 4\beta 1$ with at least about a two-fold greater, more preferably at least about five-fold greater, even more preferably at least about ten-fold greater, and most preferably at least about one hundred-fold greater, specificity for integrin α4β1 than for another integrin such as αVβ3. As such, the various RGD and RLD containing peptides that have been identified based on their relatively high binding affinity for integrin αVβ63 or for integrin αVβ5 (PCT/US94/13542) are not considered peptide antagonists of integrin α4β1 binding to its ligand, as defined herein.

Exemplary peptides which inhibit the specific binding of integrin α4β1 to one or more of its ligands include, without limitation, CS-1 fibronectin and fragments of CS-1 fibronectin, such as DELPQLVTLPHPNLHGPEILDVPST (SEQ ID NO:23), HGPEILDVPST (SEQ ID NO:24), and EILDV (SEQ ID NO:25) [Wayner et al., J. Cell Biol. (1989) 109(3): 1321-30]; LDVP (SEQ ID NO:26) [Clements et al., J. Cell Sci. (1994) 107 (Pt 8):2127-35], LDV (SEQ ID NO:27) [Wayner et al., J. Cell Biol. (1992) 116(2):489-97]; IDAP (SEQ ID NO:28) and RDV (SEQ ID NO:29) [Clements et al., J. Cell Sci. (1994) 107 (Pt 8):2127-35]; GPEYLDVP (SEQ ID NO:30) [Bochner et al., J. Exp. Med. (1991) 173(6):1553-7]; (X)C*DPC* (SEQ ID NO:40) where X is any amino acid or modified amino acid, (X) C*(X)PC* (SEQ ID NO:31) where X is any amino acid, RC*DPC* (SEQ ID NO:32), C*WLDVC* (SEQ ID NO:33), YC*APC* (SEQ ID NO:34) and YC*DPC* (SEQ ID NO:35), and phenyacyl-C*DfC* (SEQ ID NO:36) (where "f" is D-Phe) [Jackson et al., J. Med. Chem. (1997) 40(21):3359-68]; RC*D[ThioP]C* (SEQ ID NO:37) (Nowlin et al., J. Biol. Chem. (1993) Sep 25, 268(27): 20352-9]; 9-fluorenecarboxylRC*D[ThioP]C* (SEQ ID NO:38) [Cardarelli et al., J. Biol. Chem. (1994) 269(28): 18668-73]; EGYYGNYGVYA (SEQ ID NO:39) and C*YYGNC* (SEQ ID NO:97) where * indicates cyclization points; and modifications thereof [Thorsett et al., Inhibitors of leukocyte adhesion (1996) WO9602644]; 1-adamantaneacetyl-Cys-Gly-Arg-Gly-Asp-Ser-Pro-Cys (SEQ ID NO:41) [Cardarelli et al., J. Biol. Chem. (1994) 269(28): 18668-73]. Other exemplary peptides include snake disintegrins, which are exemplified by, but not limited to, EC3 from Echis carinatus, EC3B which is a subunit of EC3 and which has the sequence NSVHPCCDPVTCEPREGEHClSGPC-CRNCKFLNAGTICKRAMLDGLNDYCTGKSSD CPRN-RYKGKED (SEQ ID NO:42), MLDG (SEQ ID NO:43), a peptide fragment of EC3; and modifications thereof [Brando et al., Biochem. Biophys. Res. Commun. (2000) 267(1):413-417, and Marcinkiewicz et al., J. Biol. Chem. (1999) 274 (18):1 2468-73]; soluble VCAM [Rose et al. (2000) Blood 95:602-609]; soluble VCAM fragments [Dudgeon et al., Eur. J. Biochem. (1994) 226(2):517-23]; VCAM peptide sequences RTQIDSPLN (SEQ ID NO:44), TQIDSP (SEQ ID NO:45), QIDS (SEQ ID NO:46), IDSP (SEQ ID NO:47) and KLEK (SEQ ID NO:48) [Clements et al., J. Cell Sci. (1994) 107 (Pt 8): 2127-35].

Figure 10:
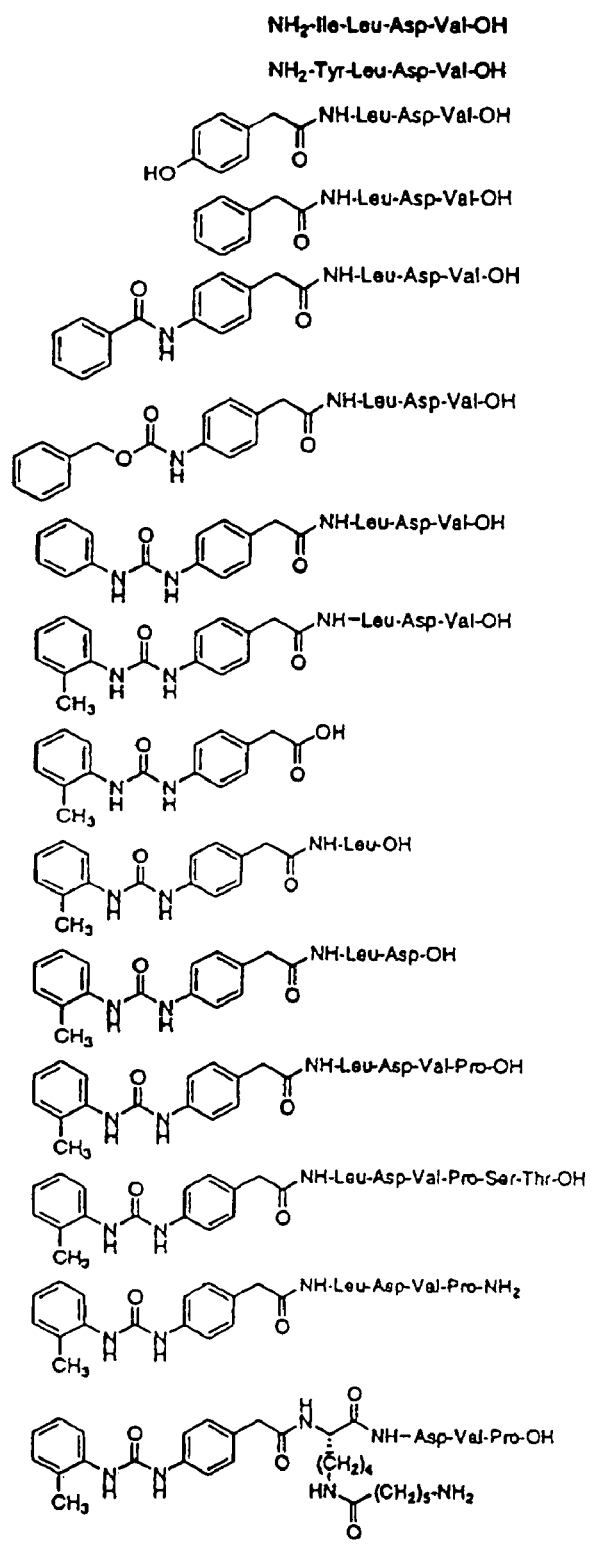
FIG. 10 shows exemplary agents which inhibit binding of integrin α4β1 to VCAM.
Figure 11:
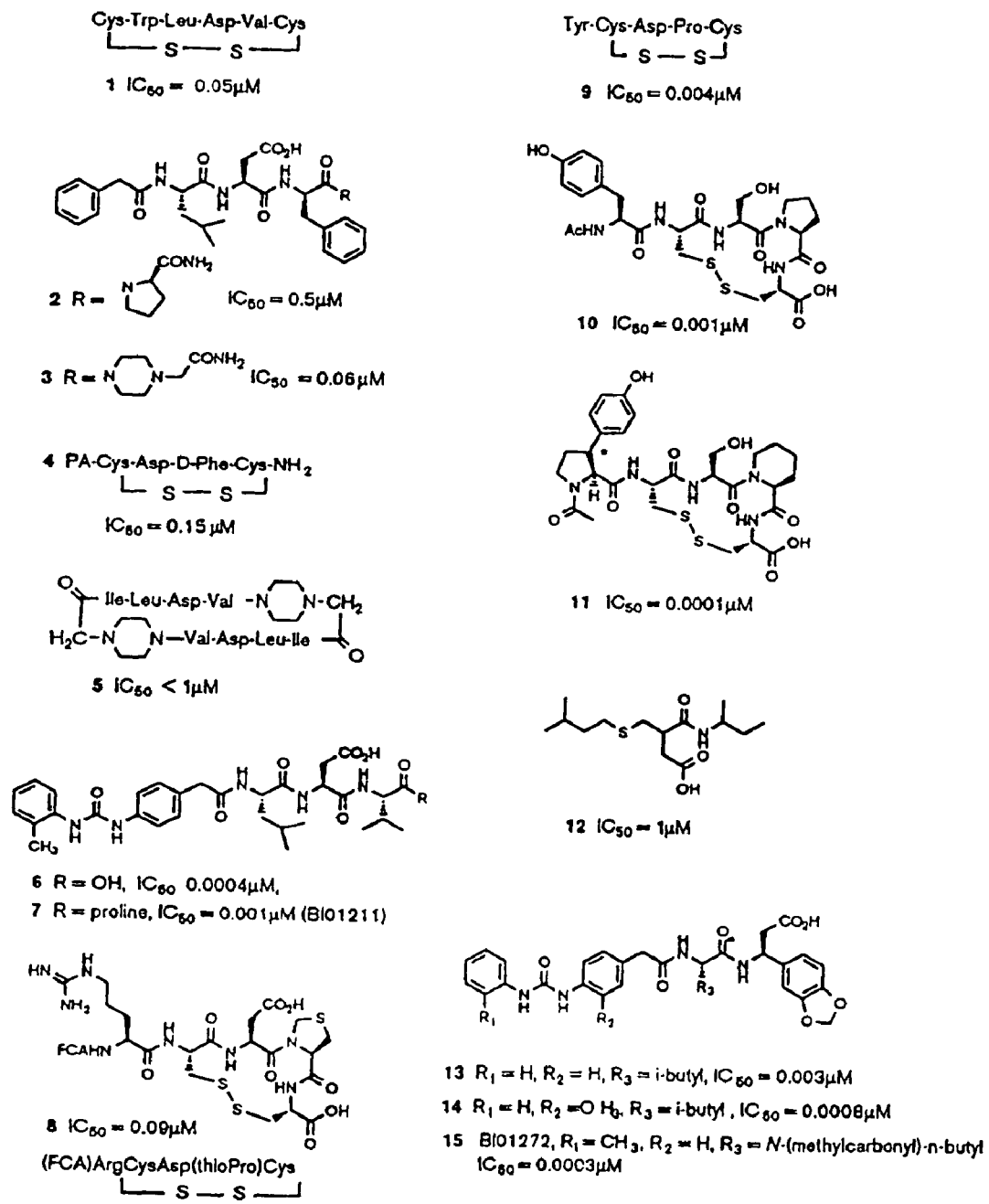
FIG. 11 shows exemplary agents which inhibit binding of integrin α4β1 to its ligands, with IC50 values based on direct binding assays. In this Figure, the abbreviations are as follows: FCA, 9-fluorenecarboxyl; IC, inhibition concentration; PA, phenylacetyl.
Figure 12:
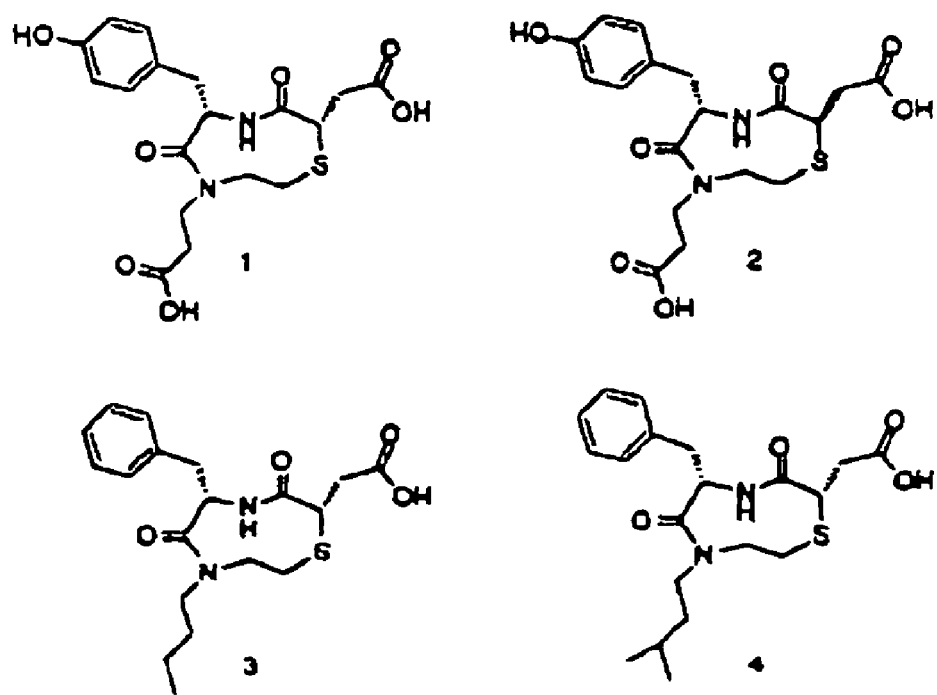
FIG. 12 shows exemplary β-turn mimetics which inhibit binding of integrin α4β1 to fibronectin.

Further exemplary modified peptides which inhibit the specific binding of integrin α4β1 to one or more of its ligands include a peptidomimetic (i.e., an organic molecules that mimics the structure of a peptide); or a peptoid such as a vinylogous peptoid. Examples of cyclic peptides and peptidomimetics which are within the scope of the invention include, without limitation, those which are based on the peptide structure GPEYLDVP (SEQ ID NO:49), such as the compound named TBC722 [Kogan et al., WO9600581], based on the peptide structure LDVP (SEQ ID NO:50) including phenylacetyl LDFp [Arrhenius et al., WO9515973; Arrhenius et al., WO9606108], based on the peptide structure ILDV (SEQ ID NO:51) [Dutta, WO9702289), BIO1211 [4-(2-methylphenylluriedo) phenylacetyl LDVP] BIO1272 [Lin et al., WO9200995; Lin et al., WO9622966], CY9652 a CS-1 peptidomimetic, TBC3342, ZD-7349 [Curley et al. (1999) Cell. Mol. Life Sci., 56:427-441]; and others [EP-842943-A2, WO9842656-A1, WO9620216-A1, WO9600581-A1, Souers et al. (1998) Bioorg. Med. Chem. Lett., 8:2297-2302]. Exemplary peptides and modified peptides are illustrated in FIG. 10 [see, Lin et al. (1999) J. Med. Chem., 42:920-934], FIG. 11 [See, Lin et al. (1998) Curr. Opin. Chem. Biol., 2:453-457], and FIG. 12 [See, Souers et al. (1998) Bioorg. Med. Chem. Lett., 8:2297-2302]. Methods for generating libraries of mimetics and for evaluating the library of mimetics for inhibiting the binding of receptors to their ligands are known in the art [Souers et al. (1998) supra].

Other peptides useful as α4β1 antagonists that reduce or inhibit angiogenesis can be purchased from commercial sources, and can be identified by screening libraries of peptides, which can be prepared using well known methods of chemical synthesis [Koivunen et al. J. Cell Biol., 124: 373-380 (1994)]. For example, peptide agonists of integrin α4β1 other than those specifically disclosed herein may be identified using methods known in the art, such as by panning phage-display peptide libraries as described in U.S. Pat. No. 5,780,426 to Palladino et al., the entire contents of which are herein incorporated by reference. For example, phage-display peptide libraries are panned with the integrin α4β1 receptor attached to a solid support, such as small diameter (1 μm) polystyrene latex beads. Phage selected by this method can then be tested for specific binding to integrin α4β1 via ELISA or other immunologically-based assays. Individual peptide sequences are then determined via sequencing of phage DNA. Further analysis of the minimal peptide sequence required for binding can be assessed via deletion and site-directed mutagenesis, followed by testing of the phage for binding to integrin α4β1 via ELISA. Since the identified peptide candidates are fused to the major phage coat protein, soluble peptides are then chemically synthesized and the activity of these free peptides are tested in various in vitro and in vivo assays for the ability to act as antagonists of the integrin α4β1 receptor.

3. Nucleic Acid Sequences

In an alternative embodiment, the agent that inhibits the specific binding of α4β1 to one or more of its ligands is a nucleic acid sequence. The terms "nucleic acid sequence" and "nucleotide sequence" as used herein refer to two or more nucleotides that are covalently linked to each other. Included within this definition are oligonucleotides, polynucleotide, and fragments or portions thereof, DNA or RNA of genomic or synthetic origin which may be single- or double-stranded, and represent the sense or antisense strand. Nucleic acid sequences that are particularly useful in the instant invention include, without limitation, antisense sequences and ribozymes. The nucleic acid sequences are contemplated to bind to genomic DNA sequences or RNA sequences that encode integrin α4β1 or one or more of its ligands, thereby inhibiting the binding of integrin α4β1 with one or more of its ligands. Antisense and ribozyme sequences may be delivered to cells by transfecting the cell with a vector that expresses the antisense nucleic acid or the ribozyme as an mRNA molecule. Alternatively, delivery may be accomplished by entrapping ribozymes and antisense sequences in liposomes.

a. Antisense Sequences

Antisense sequences have been successfully used to inhibit the expression of several genes [Markus-Sekura (1988) Anal. Biochem. 172:289-295; Hambor et al. (1988) J. Exp. Med. 168:1237-1245; and patent EP 140 308], including the gene encoding VCAM1, one of the integrin α4β1 ligands [U.S. Pat. No. 6,252,043, incorporated in its entirety by reference]. The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter that permits the synthesis of antisense RNA. The transcribed antisense RNA strand combines with natural mRNA produced by the cell to form duplexes. These duplexes then block either the further transcription of the mRNA or its translation, or promote its degradation.

Any antisense sequence is contemplated to be within the scope of this invention if it is capable of reducing the level of expression of integrin α4β1 and/or one or more of its ligands (e.g., VCAM and fibronectin) to a quantity which is less than the quantity of integrin α4β1 or integrin α4β1 ligand expression in a corresponding control tissue which is (a) not treated with the antisense integrin α4β1 or integrin α4β1 ligand sequence, (b) treated with a corresponding sense integrin α4β1 or integrin α4β1 ligand sequence, or (c) treated with a nonsense sequence.

The terms "reducing the level of expression of integrin α4β1 or integrin α4β1 ligand," "diminishing integrin α4β1 or integrin α4β1 ligand expression" and grammatical equivalents thereof, refer to reducing the level of integrin α4β1 or integrin α4β1 ligand expression to a quantity which is preferably 20% less than the quantity in a corresponding control tissue, more preferably is 50% less than the quantity in a corresponding control tissue, yet more preferably is 90% less than the quantity in a corresponding control tissue, and most preferably is at the background level of, or is undetectable by, a Western blot analysis of integrin α4β1 or integrin α4β1 ligand, by immunofluorescence for detection of integrin α4β1 or integrin α4β1 ligand, by reverse transcription polymerase chain (RT-PCR) reaction for detection of integrin α4β1 or integrin α4β1 ligand mRNA, or by in situ hybridization for detection of integrin α4β1 or integrin α4β1 ligand mRNA. When a background level or undetectable level of integrin α4β1 or integrin α4β1 ligand peptide or mRNA is measured, this may indicate that integrin α4β1 or integrin α4β1 ligand is not expressed. A reduced level of integrin α4β1 or integrin α4β1 ligand need not, although it may, mean an absolute absence of expression of integrin α4β1 or integrin α4β1 ligand. The invention does not require, and is not limited to, antisense integrin α4β1 or integrin α4β1 ligand sequences that eliminate expression of integrin α4β1 or integrin α4β1 ligand.

Antisense integrin α4β1 or integrin α4β1 ligand sequences capable of reducing the level of integrin α4β1 expression include, for example, sequences which are capable of hybridizing with at least a portion of integrin α4β1 cDNA or integrin α4β1 ligand cDNA under high stringency or low stringency conditions. Low stringency conditions when used in reference to nucleic acid hybridization comprise conditions equivalent to binding or hybridization at 68° C. in a solution consisting of 5×SSPE (43.8 g/l NaCl, 6.9 g/l NaH$_2$PO$_4$—H$_2$O and 1.85 g/l EDTA, pH adjusted to 7.4 with NaOH), 1% SDS, 5× Denhardt's reagent [50× Denhardt's contains the following per 500 ml: 5 g Ficoll (Type 400, Pharmacia), 5 g BSA (Fraction V; Sigma)] and 100 µg/ml denatured salmon sperm DNA followed by washing in a solution comprising 0.2× SSPE, and 0.1% SDS at room temperature when a DNA probe of about 100 to about 1000 nucleotides in length is employed. High stringency conditions when used in reference to nucleic acid hybridization comprise conditions equivalent to binding or hybridization at 68° C. in a solution consisting of 5×SSPE, 1% SDS, 5× Denhardt's reagent and 100 µg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

Antisense integrin α4β1 sequences and antisense integrin α4β1 ligand sequences within the scope of this invention may be designed using approaches known in the art. In a preferred embodiment, the antisense integrin α4β1 sequences and antisense integrin α4β1 ligand sequences are designed to be hybridizable to integrin α4β1 mRNA or to integrin α4β1 ligand mRNA which is encoded by the coding region of the integrin α4β1 gene and the integrin α4β1 ligand gene, respectively. Alternatively, antisense integrin α4β1 or integrin α4β1 ligand sequences may be designed to reduce transcription by hybridizing to upstream nontranslated sequences, thereby preventing promoter binding to transcription factors.

In a preferred embodiment, the antisense oligonucleotide sequences of the invention range in size from about 8 to about 100 nucleotide residues. In yet a more preferred embodiment, the oligonucleotide sequences range in size from about 8 to about 30 nucleotide residues. In a most preferred embodiment, the antisense sequences have 20 nucleotide residues.

However, the invention is not intended to be limited to the number of nucleotide residues in the oligonucleotide sequence disclosed herein. Any oligonucleotide sequence that is capable of reducing expression of integrin α4β1 or of integrin α4β1 ligand is contemplated to be within the scope of this invention. For example, oligonucleotide sequences may range in size from about 3 nucleotide residues to the entire integrin α4β1 or integrin α4β1 ligand cDNA sequence. The art skilled know that the degree of sequence uniqueness decreases with decreasing length, thereby reducing the specificity of the oligonucleotide for the integrin α4β1 mRNA, or integrin α4β1 ligand mRNA.

The antisense oligonucleotide sequences that are useful in the methods of the instant invention may comprise naturally occurring nucleotide residues as well as nucleotide analogs. Nucleotide analogs may include, for example, nucleotide residues that contain altered sugar moieties, altered intersugar linkages (e.g., substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures), or altered base units. Oligonucleotide analogs are desirable, for example, to increase the stability of the antisense oligonucleotide compositions under biologic conditions since natural phosphodiester bonds are not resistant to nuclease hydrolysis. Oligonucleotide analogs may also be desirable to improve incorporation efficiency of the oligonucleotides into liposomes, to enhance the ability of the compositions to penetrate into the cells where the nucleic acid sequence whose activity is to be modulated is located, in order to reduce the amount of antisense oligonucleotide needed for a therapeutic effect thereby also reducing the cost and possible side effects of treatment.

Antisense oligonucleotide sequences may be synthesized using any of a number of methods known in the art, as well as using commercially available services (e.g., Genta, Inc.). Synthesis of antisense oligonucleotides may be performed, for example, using a solid support and commercially available DNA synthesizers. Alternatively, antisense oligonucleotides may also be synthesized using standard phosphoramidate chemistry techniques. For example, it is known in the art that for the generation of phosphodiester linkages, the oxidation is mediated via iodine, while for the synthesis of phosphorothioates, the oxidation is mediated with 3H-1,2-benzodithiole-3-one,1,-dioxide in acetonitrile for the step-wise thioation of the phosphite linkages. The thioation step is followed by a capping step, cleavage from the solid support, and purification on HPLC, e.g., on a PRP-1 column and gradient of acetonitrile in triethylammonium acetate, pH 7.0.

In one embodiment, the antisense DNA sequence is an "integrin α4α1 antisense DNA sequence" (i.e., an antisense DNA sequence which is designed to bind with at least a portion of the integrin α4β1 genomic sequence or with integrin α4β1 mRNA). The design of integrin α4β1 antisense DNA sequences is facilitated by the availability of the sequences for the integrin α4 subunit cDNA (FIG. 13 and FIG. 14), and integrin G31 cDNA (FIG. 15). Particularly preferred antisense sequences are those which hybridize with genomic DNA or with RNA encoding a portion of integrin α4β1 which is involved in the specific binding with one or more of its ligands. Such integrin α4β1 portions are exemplified by, but not limited to, the sequences (see FIG. 6) which comprises the sequence IVTCGHRWKNIFYIKNEN-KLPTGGCYGVPPDLRTELSKRIAP-CYQDYVKKFGENFA ASCQAGISSFYTKDLIVM-GAPGSSYWTGSLFVYNITTNKYKAFLDKQNQVKF GSYL GYSVGAGHFRSQHTTEVVGGAPQHE-QIGKAYIFSIDEKELNILHEMKGKK (SEQ ID NO:10) (from amino acid 141 to amino acid 301), GHRWKN IFY-IKNENKLPTGG (SEQ ID NO:11) (from amino acid 145 to amino acid 164), YQDYVKKFGENFAS (SEQ ID NO:12) (from amino acid 184 to amino acid 197), SYWTGS (SEQ ID NO:13) (from amino acid 186 to amino acid 224), GGAPQHEQIGK (SEQ ID NO:14) (from amino acid 270 to amino acid 280), YNVDTES ALLYQGPHNT IFGYSVV-LHS HGANRWLLVG APTANWLANA SVINP (SEQ ID NO:54) (from amino acid 34 to amino acid 85), GRPYN-VDTESALLYQGPHNTLFGYSVVLHSHGANRWLLVG APTANWLANASVINPGAIYR (SEQ ID NO:55), GVPT-GRPYNVDTESAL LYQGPHNT LFGYSVVLHSHGANR-WLLVGAPTANWLANASVI NPGAIYRCRIGKNPGQT (SEQ ID NO:56), IVTCGHRWKNIFYIKNENKLPTG-GCYG (SEQ ID NO:57), GHRWKNIFYIKNENKLPTG-GCYGVPPDLRTELSK (SEQ ID NO:58), APCYQDYVKKFGENFAS (SEQ ID NO:59), CYQDYVKKFGENFASCQA GISSFYTKDL (SEQ ID NO:60), GSSYWTGSLFVYNI (SEQ ID NO:61), RSQHT-TEVVGGAPQHEQIGK (SEQ ID NO:62), GGAPQHE-QIGKAYIFSIDEKEL (SEQ ID NO:63), and/or GGAPQHE-QIGKA (SEQ ID NO:64).

In another embodiment, the antisense DNA sequence is a "vascular cell adhesion molecule antisense DNA sequence," i.e., and antisense DNA sequence which is designed to bind with at least a portion of the VCAM genomic sequence or with VCAM α4β1 mRNA. The selection and design of these antisense sequences is made possible by the availability of VCAM cDNA sequences (FIG. 16). Exemplary preferred antisense sequences are those which hybridize with genomic DNA or with RNA encoding a portion of VCAM which is involved in the specific binding of VCAM with integrin α4β1, such as the VCAM (FIG. 8A, GenBank Accession Nos. P19320) comprise the amino acid sequence RTQIDSPLNG (SEQ ID NO:15) (from amino acid 60 to amino acid 69); RTQIDSPLSG (SEQ ID NO:16) (from amino acid 348 to amino acid 357), KLEK (SEQ ID NO:17) (from amino acid 103 to amino acid 106, and from amino acid 391 to amino acid 394), RTQIDSPLNG (SEQ ID NO:15), RTQIDSPLSG (SEQ ID NO:16), KLEK (SEQ ID NO:17), WRTQIDSPLNGK (SEQ ID NO:65), SWRTQIDSPLNGKV (SEQ ID NO:66), SWRTQIDSPLNGKVT (SEQ ID NO:67), PFFSWRTQID-SPLNGKVTNE (SEQ ID NO:68), SRKLEKGI (SEQ ID NO:69), CESRKLEKGIQV (SEQ ID NO:70), ATCES-RKLEKGIQVEI (SEQ ID NO:71), LCTATCESRKLE-KGIQVEIYSFPKDPE (SEQ ID NO:72), GHKKLE-KGIQVEL (SEQ ID NO:73), VTCGHKKLEKGI (SEQ ID NO:74), TCGHKKLEKGIQVELYSFPRDPE (SEQ ID NO:75), PVSFENEHSYLCTVTCGHKKLEKG (SEQ ID NO:76), RTQIDSPLSGK (SEQ ID NO:77), FSWRTQID-SPLSGKVR (SEQ ID NO:78), and/or ESPSFWWRTQID-SPLSGK (SEQ ID NO:79).

In yet another embodiment, the antisense DNA sequence is a "fibronectin α4β1 antisense DNA sequence" (i.e., an antisense DNA sequence which is designed to bind with at least a portion of the fibronectin genomic sequence or with fibronectin α4β1 mRNA). The selection and design of these antisense sequences is made possible by the availability of the sequence for fibronectin cDNA (FIG. 17). Exemplary nucleic acid sequences which may be targeted are those which encode the following sequences shown in FIG. 9, the IIICS sequence (SEPLIGRKKTDELPQLVTLPHPNLHGPE ILDVP-STVQKTPFVTHPGYDTGNGIQLPGGTS-GQQPSVGQQMIFEEHGFRRTTPPTT ATPIRHRPRPYP-PNVGEEIQIGHIPREDVVDYHLYPHGPGLNPNAST) (SEQ ID NO:18) from amino acid 1982 to amino acid 2111, the CS-1 sequence which contains the amino acid sequence LDV (SEQ ID NO:19) (from amino acid 2011 to amino acid 2013), the CS-5 sequence which contains the amino acid sequence REDV (SEQ ID NO:20) (from amino acid 2091 to amino acid 2093), IDAPS (SEQ ID NO:21) (from amino acid 1903 to amino acid 1907), TAIDAPSNLRDAS (SEQ ID NO:80), TAIDAPSNLRFLATTP (SEQ ID NO:81), RSSPV-VIDASTAIDAPS (SEQ ID NO:82), IDAPSNLRFLATTP-NSLLV (SEQ ID NO:83), IDAPSNLRFLATTP-NSLLVSWQPPRARITGYIIKYE (SEQ ID NO:84), IDDVPST (SEQ ID NO:85), NLHGPEILDVPSTVQK (SEQ ID NO:86), PHPNLHGPEILDV (SEQ ID NO:87), ILDVP-STVQKTPFVTHPGYD (SEQ ID NO:88), VTLPHPNLHG-PEILDVP (SEQ ID NO:89), EILDV (SEQ ID NO:90), IPREDVDY (SEQ ID NO:91), GHIPRDDVD (SEQ ID NO:92), GHIPREDV (SEQ ID NO:93), LDVPSTVQKT-PFVTHPGYDTGNGIQLPGTSGQQPSVGQQMIFEEHG FRRTTPPTTATPIRHRPRPYPPNVGEEIQIGHIPREDV (SEQ ID NO:94), and/or PEILDVPSTVQKTPFVTHPGY- DTGNGIQLPGTSGQQPSVGQQMIFEEHGFRRTTPPT
TTATPIRHRPRPYPPNVGEEIQIGHIPREDVDY (SEQ ID NO:95).

b. Ribozyme

In some alternative embodiments, the agent that inhibits the specific binding of integrin α4β1 to its ligand is a ribozyme. Ribozyme sequences have been successfully used to inhibit the expression of several genes including the gene encoding VCAM1, which is one of the integrin α4β1 ligands [U.S. Pat. No. 6,252,043, incorporated in its entirety by reference].

The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred, in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences.

The ability of a ribozyme to cleave at a substrate cleavage site may readily be determined using methods known in the art. These methods include, but are not limited to, the detection (e.g., by Northern blot analysis as described herein, reverse-transcription polymerase chain reaction (RT-PCR), in situ hybridization and the like) of reduced in vitro or in vivo levels of RNA which contains a ribozyme substrate cleavage site for which the ribozyme is specific, compared to the level of RNA in controls (e.g., in the absence of ribozyme, or in the presence of a ribozyme sequence which contains a mutation in one or both unpaired nucleotide sequences which renders the ribozyme incapable of cleaving a substrate RNA).

Ribozymes contemplated to be within the scope of this invention include, but are not restricted to, hammerhead ribozymes [See e.g., Reddy et al., U.S. Pat. No. 5,246,921; Taira et al., U.S. Pat. No. 5,500,357, Goldberg et al., U.S. Pat. No. 5,225,347, the contents of each of which are herein incorporated by reference], Group I intron ribozyme [Kruger et al. (1982) Cell 31: 147-157], ribonuclease P [Guerrier-Takada et al. (1983) Cell 35: 849-857], hairpin ribozyme [Hampel et al., U.S. Pat. No. 5,527,895 incorporated by reference], and hepatitis delta virus ribozyme [Wu et al. (1989) Science 243:652-655].

A ribozyme may be designed to cleave at a substrate cleavage site in any substrate RNA so long as the substrate RNA contains one or more substrate cleavage sequences, and the sequences flanking the substrate cleavage site are known. In effect, expression in vivo of such ribozymes and the resulting cleavage of RNA transcripts of a gene of interest reduces or ablates expression of the corresponding gene.

For example, where the ribozyme is a hammerhead ribozyme, the basic principle of a hammerhead ribozyme design involves selection of a region in the substrate RNA which contains a substrate cleavage sequence, creation of two stretches of antisense oligonucleotides (i.e., the binding regions) which hybridize to sequences flanking the substrate cleavage sequence, and placing a sequence which forms a hammerhead catalytic region between the two binding regions.

In order to select a region in the substrate RNA which contains candidate substrate cleavage sites, the sequence of the substrate RNA needs to be determined. The sequence of RNA encoded by a genomic sequence of interest is readily determined using methods known in the art. For example, the sequence of an RNA transcript may be arrived at either manually, or using available computer programs (e.g., GENEWORKS,.from IntelliGenetic Inc., or RNADRAW available from the internet), by changing the T in the DNA sequence encoding the RNA transcript to a U.

Substrate cleavage sequences in the target RNA may be located by searching the RNA sequence using available computer programs. For example, where the ribozyme is a hammerhead ribozyme, it is known in the art that the catalytic region of the hammerhead ribozyme cleaves only at a substrate cleavage site which contains a NUH, where N is any nucleotide, U is a uridine, and H is a cytosine (C), uridine (U), or adenine (A) but not a guanine (G). The U-H doublet in the NUH cleavage site does not include a U-G doublet since a G would pair with the adjacent C in the ribozyme and prevent ribozymne cleavage. Typically, N is a G and H is a C. Consequently, GUC has been found to be the most efficient substrate cleavage site for hammerhead ribozymes, although ribozyme cleavage at CUC is also efficient.

In a preferred embodiment, the substrate cleavage sequence is located in a loop structure or in an unpaired region of the substrate RNA. Computer programs for the prediction of RNA secondary structure formation are known in the art and include, for example, "RNADRAW", "RNAFOLD", "DNASIS" (Hitachi), and The Vienna RNA Package.

In addition to the desirability of selecting substrate cleavage sequences which are located in a loop structure or an unpaired region of the substrate RNA, it is also desirable, though not required, that the substrate cleavage sequence be located downstream (i.e., at the 3'-end) of the translation start codon (AUG or GUG) such that the translated truncated polypeptide is not biologically functional.

In a preferred embodiment, the ribozyme is an "integrin α4β1 ribozyme" (i.e., a ribozyme whose substrate cleavage sequence is designed to hybridize with a portion of integrin α4β1 that is involved in the specific binding of integrin α4β1 with one or more of its ligands). Such integrin α4β1 portions are exemplified by, but not limited to, the sequences (see FIG. 6) which comprises the sequence IVTCGHRWKNIFY-IKNENKLPTGGCYGVPPDLRTELSKRI-APCYQDYVKKFGENFA ASCQAGISSFYTKDLIVM-GAPGSSYWTGSLFVYNITTNKYKAFLDKQNQ
VFGSYL GYSVGAGHFRSQHTTEVVGGAPQHE-QIGKAYIFSIDEKELNILHEMKGKK (SEQ ID NO:10) (from amino acid 141 to amino acid 301), GHRWKN IFY-IKNENKLPTGG (SEQ ID NO:11) (from amino acid 145 to amino acid 164), YQDYVKKFGENFAS (SEQ ID NO:12) (from amino acid 184 to amino acid 197), SYWTGS (SEQ ID NO:13) (from amino acid 186 to amino acid 224), GGAPQHEQIGK (SEQ ID NO:14) (from amino acid 270 to amino acid 280), YNVDTES ALLYQGPHNT IFGYSVVLHS HGANRWLLVG APTANWLANA SVINP (SEQ ID NO:54) (from amino acid 34 to amino acid 85), GRPYNVDTESALLYQGPHNTLFGYSVVLHSHGANRWLLVG APTANWLANASVINPGAIYR (SEQ ID NO:55), GVPTGRPYNVDTESAL LYQGPHNT LFGYSVVLHSHGANRWLLVGAPTANWLANASVI NPGAIYRCRIGKNPGQT (SEQ ID NO:56), IVTCGHRWKNIFYIKNENKLPTGGCYG (SEQ ID NO:57), GHRWKNIFYIKNENKLPTGGCYGVPPDLRTELSK (SEQ ID NO:58), APCYQDYVKKFGENFAS (SEQ ID NO:59), CYQDYVKKFGENFASCQA GISSFYTKDL (SEQ ID NO:60), GSSYWTGSLFVYNI (SEQ ID NO:61), RSQHTTEVVGGAPQHEQIGK (SEQ ID NO:62), GGAPQHEQIGKAYIFSIDEKEL (SEQ ID NO:63), and/or GGAPQHEQIGKA (SEQ ID NO:64).

In an alternative embodiment, the substrate cleavage sequence is designed to hybridize with a portion of an integrin $\alpha 4\beta 1$ ligand, wherein the portion is involved in the specific binding of the ligand with integrin $\alpha 4\beta 1$.

In a more preferred embodiment, the ribozyme is a "vascular cell adhesion molecule ribozyme" (i.e., a ribozyme whose substrate cleavage sequence is designed to hybridize with a portion of VCAM that is involved in the specific binding of VCAM with integrin $\alpha 4\beta 1$). Exemplary portions of the ligand VCAM (FIG. 8A, GenBank Accession Nos. P19320) comprise the amino acid sequence RTQIDSPLNG (SEQ ID NO:15) (from amino acid 60 to amino acid 69); RTQIDSPLSG (SEQ ID NO:16) (from amino acid 348 to amino acid 357), KLEK (SEQ ID NO:17) (from amino acid 103 to amino acid 106, and from amino acid 391 to amino acid 394), RTQIDSPLNG (SEQ ID NO:15), RTQIDSPLSG (SEQ ID NO:16), KLEK (SEQ ID NO:17), WRTQIDSPLNGK (SEQ ID NO:65), SWRTQIDSPLNGKV (SEQ ID NO:66), SWRTQIDSPLNGKVT (SEQ ID NO:67), PFFSWRTQIDSPLNGKVTNE (SEQ ID NO:68), SRKLEKGI (SEQ ID NO:69), CESRKLEKGIQV (SEQ ID NO:70), ATCESRKLEKGIQVEI (SEQ ID NO:71), LCTATCESRKLEKGIQVEIYSFPKDPE (SEQ ID NO:72), GHKKLEKGIQVEL (SEQ ID NO:73), VTCGHKKLEKGI (SEQ ID NO:74), TCGHKKLEKGIQVELYSFPRDPE (SEQ ID NO:75), PVSFENEHSYLCTVTCGHKKLEKG (SEQ ID NO:76), RTQIDSPLSGK (SEQ ID NO:77), FSWRTQIDSPLSGKVR (SEQ ID NO:78), and/or ESPSFWWRTQIDSPLSGK (SEQ ID NO:79).

In an alternative preferred embodiment, the ribozyme is a "fibronectin ribozyme" (i.e., a ribozyme whose substrate cleavage sequence is designed to hybridize with a portion of fibronectin that is involved in the specific binding of fibronectin with integrin $\alpha 4\beta 1$). Exemplary portions of the ligand fibronectin comprise the following sequences shown in FIG. 9, the IIICS sequence (SEPLIGRKKTDELPQLVTLP HPNLHGPEILDVPSTVQKTPFVTHPGYDTGNGIQLPGGTSGQQPSVGQQMIFEEHGF RRTTPPTTATPIRHRPRPYPPNVGEEIQIGHIPREDVVDYHLYP HGPGLNPN AST) (SEQ ID NO:18) from amino acid 1982 to amino acid 2111, the CS-1 sequence which contains the amino acid sequence LDV (SEQ ID NO:19) (from amino acid 2011 to amino acid 2013), the CS-5 sequence which contains the amino acid sequence REDV (SEQ ID NO:20) (from amino acid 2091 to amino acid 2093), IDAPS (SEQ ID NO:21) (from amino acid 1903 to amino acid 1907), TAIDAPSNLRDAS (SEQ ID NO:80), TAIDAPSNLRFLATTP (SEQ ID NO:81), RSSPVVIDASTAIDAPS (SEQ ID NO:82), IDAPSNLRFLATTPNSLLV (SEQ ID NO:83), IDAPSNLRFLATTPNSLLVSWQPPRARITGYIIKYE (SEQ ID NO:84), IDDVPST (SEQ ID NO:85), NLHGPEILDVPSTVQK (SEQ ID NO:86), PHPNLHGPEILDV (SEQ ID NO:87), ILDVPSTVQKTPFVTHPGYD (SEQ ID NO:88), VTLPHPNLHGPEILDVP (SEQ ID NO:89), EILDV (SEQ ID NO:90), IPREDVDY (SEQ ID NO:91), GHIPRDDVD (SEQ ID NO:92), GHIPREDV (SEQ ID NO:93), LDVPSTVQKTPFVTHPGYDTGNGIQLPGTSGQQPSVGQQMIFEEHG FRRTTPPTTATPIRHRPRPYPPNVGEEIQIGHIPREDV (SEQ ID NO:94), and/or PEILDVPSTVQKTPFVTHPGYDTGNGIQLPGTSGQQPSVGQQMIFEEHGFRRTTPPT TTATPIRHRPRPYPPNVGEEIQIGHIPREDVDY (SEQ ID NO:95).

It is known in the art that the specificity of ribozyme cleavage for a substrate RNA molecule is determined by the sequence of nucleotides which flank the substrate cleavage site and which hybridize with the ribozyme binding regions. Thus, ribozymes can be designed to cleave at different locations within a substrate RNA molecule by altering the sequence of the binding regions that surround the ribozyme catalytic region of the ribozyme such that the binding regions hybridize with any known sequence on the substrate RNA.

In addition to varying the sequence of the binding regions to effect binding to different locations on the RNA substrate, the number of nucleotides in each of the ribozyme binding regions may also be altered in order to change the specificity of the ribozyme for a given location on the RNA substrate. The number of nucleotides in a binding region is preferably between about 5 and about 25 nucleotides, more preferably between about 11 and about 15 nucleotides, yet more preferably between about 7 nucleotides and about 10 nucleotides.

One of skill in the art appreciates that it is not necessary that the two binding regions that flank the ribozyme catalytic region be of equal length. Binding regions that contain any number of nucleotides are contemplated to be within the scope of this invention so long as the desirable specificity of the ribozyme for the RNA substrate and the desirable cleavage rate of the RNA substrate are achieved. One of skill in the art knows that binding regions of longer nucleotide sequence, while increasing the specificity for a particular substrate RNA sequence, may reduce the ability of the ribozyme to dissociate from the substrate RNA following cleavage to bind with another substrate RNA molecule, thus reducing the rate of cleavage. On the other hand, though binding regions with shorter nucleotide sequences may have a higher rate of dissociation and cleavage, specificity for a substrate cleavage site may be compromised.

It is well within the skill of the art to determine an optimal length for the binding regions of a ribozyme such that a desirable specificity and rate of cleavage are achieved. Both the specificity of a ribozyme for a substrate RNA and the rate of cleavage of a substrate RNA by a ribozyme may be determined by, for example, kinetic studies in combination with Northern blot analysis or nuclease protection assays.

In a preferred embodiment, the complementarity between the ribozyme binding regions and the substrate RNA is complete. However, the invention is not limited to ribozyme sequences in which the binding regions show complete complementarity with the substrate RNA. Complementarity may be partial, so long as the desired specificity of the ribozyme for a substrate cleavage site and the rate of cleavage of the substrate RNA are achieved. Thus, base changes may be made in one or both of the ribozyme binding regions as long as substantial base pairing with the substrate RNA in the regions flanking the substrate cleavage sequence is maintained and base pairing with the substrate cleavage sequence is minimized. The term "substantial base pairing" means that greater than about 65%, more preferably greater than about 75%, and yet more preferably greater than about 90% of the bases of the hybridized sequences are base-paired.

It may be desirable to increase the intracellular stability of ribozymes expressed by an expression vector. This is achieved by designing the expressed ribozyme such that it contains a secondary structure (e.g., stem-loop structures) within the ribozyme molecule. Secondary structures which are suitable for stabilizing ribozymes include, but are not limited to, stem-loop structures formed by intra-strand base pairs. An alternative to the use of a stem-loop structure to protect ribozymes against ribonuclease degradation is by the insertion of a stem loop at each end of the ribozyme sequence [Sioud and Drlica (1991) Proc. Natl. Acad. Sci. USA 88:7303-7307]. Other secondary structures which are useful in reducing the susceptibility of a ribozyme to ribonuclease degradation include hairpin, bulge loop, interior loop, multi-branched loop, and pseudoknot structure as described in "Molecular and Cellular Biology," Stephen L. Wolfe (Ed.), Wadsworth Publishing Company (1993) p. 575. Additionally, circularization of the ribozyme molecule protects against ribonuclease degradation since exonuclease degradation is initiated at either the 5'-end or 3'-end of the RNA. Methods of expressing a circularized RNA are known in the art [see, e.g., Puttaraju et al. (1993) Nucl. Acids Res. 21:4253-4258].

Once a ribozyme with desirable binding regions, a catalytic region and nuclease stability has been designed, the ribozyme may be produced by any known means including chemical synthesis. Chemically synthesized ribozymes may be introduced into a cell by, for example, microinjection electroporation, lipofection, etc. In a preferred embodiment, ribozymes are produced by expression from an expression vector that contains a gene encoding the designed ribozyme sequence.

4. Other Agents

While the present invention is illustrated herein using antibody, peptide, and nucleic acid sequences which inhibit the specific binding of integrin $\alpha 4\beta 1$ to one or more of its ligands, the invention expressly contemplates within its scope other agents (e.g., organic molecules, inorganic molecules, etc.) so long as the agent is capable of inhibiting the specific binding of integrin $\alpha 4\beta 1$ to one or more of its ligands. Such agents may be identified by screening libraries of test compounds using a competitive binding assay or a cell adhesion assay. In a competitive binding assay, for example, integrin $\alpha 4\beta 1$ is coated on plastic microtiter plates and contacted with a labeled known integrin $\alpha 4\beta 1$ ligand (e.g., CS-1 fibronectin or VCAM). The test compounds are tested for their ability to inhibit binding of the labeled ligand to integrin $\alpha 4\beta 1$. Compounds that inhibit such binding are identified as agents that are capable of inhibiting the specific binding of integrin $\alpha 4\beta 1$ to the ligand.

Alternatively, in a cell adhesion assay, a labeled known integrin $\alpha 4\beta 1$ ligand (e.g., CS-1 fibronectin or VCAM) is coated on culture plates, and cells which express integrin $\alpha 4\beta 1$ are allowed to adhere to the ligand for 20-30 minutes in the presence of libraries of test compounds. Compounds that inhibit the binding of the integrin $\alpha 4\beta 1$-expressing cells to the coating of integrin $\alpha 4\beta 1$ ligand are identified as agents that inhibit the specific binding of integrin $\alpha 4\beta 31$ to the ligand.

iii. Inhibiting Angiogenesis in a Subject

The invention provides methods for inhibiting undesirable angiogenesis in a subject by inhibiting the binding of $\alpha 4\beta 1$ to one or more of its ligands (e.g., fibronectin and VCAM) in the tissue in the subject.

Undesirable angiogenesis includes normal angiogenesis processes (e.g., scar formation during wound healing or during fertility), and angiogenesis, which is associated with a pathological condition, such as that which occurs in ocular tissue (e.g., retina, macular or cornea), in skin such as occurs with psoriasis, in synovial tissue, in bone, in intestinal tissue, or in a tumor. Preferably, inhibiting angiogenesis results in reducing the severity of the undesirable angiogenesis and/or pathological condition that is associated with angiogenesis.

An advantage of the methods of the present invention is that inhibition of angiogenesis in a subject is inherently less toxic using the methods of the present invention, as compared with currently available treatments. This is because the methods of the present invention specifically target those cells that are involved in angiogenesis in the disease site, thus sparing healthy tissues from deleterious side effects. In addition, inhibition of angiogenesis offers a therapeutic approach to the treatment of diseases such as rheumatoid arthritis, neovascular eye disease, and psoriasis, for which no effective therapy exits.

The terms "pathological condition" and "angiogenic disease" are used broadly herein to mean any abnormal physical or physiological condition characterized, at least in part, by angiogenesis associated with $\alpha 4\beta 1$ integrin expression on newly forming blood vessels in a tissue. Such pathological conditions are exemplified by, but not limited to, neoplasms, ocular diseases such as diabetic retinopathy and macular degeneration associated with neovascularization, skin diseases such as psoriasis and hemangiomas, gingivitis, arthritic conditions such as rheumatoid arthritis and osteoarthritis, and inflammatory bowel diseases.

The terms "neoplasm" and "tumor" refer to a tissue growth that is characterized, in part, by angiogenesis. Neoplasms may be benign and are exemplified, but not limited to, a hemangioma, glioma, teratoma, and the like. Neoplasms may alternatively be malignant, for example, a carcinoma, sarcoma, glioblastoma, astrocytoma, neuroblastoma, retinoblastoma, and the like.

The terms "malignant neoplasm" and "malignant tumor" refer to a neoplasm that contains at least one cancer cell. A "cancer cell" refers to a cell undergoing early, intermediate or advanced stages of multi-step neoplastic progression as previously described [H. C. Pitot (1978) in "Fundamentals of Oncology," Marcel Dekker (Ed.), New York pp 15-28]. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid, but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive (i.e., they either invade adjacent tissues, or are shed from the primary site and circulate through the blood and lymph) to other locations in the body where they initiate one or more secondary cancers (i.e., "metastases"). Thus, the term "cancer" is used herein to refer to a malignant neoplasm, which may or may not be metastatic. Malignant neoplasms that can be diagnosed using a method of the invention include, for example, carcinomas such as lung cancer, breast cancer, prostate cancer, cervical cancer, pancreatic cancer, colon cancer, ovarian cancer; stomach cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (e.g., synovium cancer), glioblastoma, lymphoma, and leukemia. Malignant neoplasms are further exemplified by sarcomas (such as osteosarcoma and Kaposi's sarcoma). The invention expressly contemplates within its scope any malignant neoplasm, so long as the neoplasm is characterized, at least in part, by angiogenesis associated with $\alpha4\beta1$ expression by the newly forming blood vessels.

The terms "reducing the severity of a pathological condition," "diminishing the severity of a pathological condition, and "reducing symptoms associated with a pathological condition" mean that adverse clinical signs or symptoms associated with the pathological condition are reduced, delayed, or eliminated, as compared to the level of the pathological condition in the absence of treatment with the particular composition or method. The effects of diminishing the severity of a pathological condition may be determined by methods routine to those skilled in the art including, but not limited to, angiography, ultrasonic evaluation, fluoroscopic imaging, fiber optic endoscopic examination, biopsy and histology, blood tests, which can be used to determine relevant enzyme levels or circulating antigen or antibody, imaging tests which can be used to detect a decrease in the growth rate or size of a neoplasm, or an ophthalmic procedure which can be used to identify a reduction in the number of blood vessels in the retina of a diabetic patient. Such clinical tests are selected based on the particular pathological condition being treated. For example, it is contemplated that the methods of the invention result in a "reduction in tumor tissue" (e.g., a decrease in the size, weight, and/or volume of the tumor tissue) as compared to a control tumor tissue (e.g., the same tumor prior to treatment with the invention's methods, or a different tumor in a control subject). A reduction in the severity of a pathological condition also can be detected based on comments made by the patient being treated, for example, that a patient suffering from arthritis feels less pain or has greater joint mobility, or that a patient with diabetic retinopathy or with macular degeneration due to neovascularization can see more clearly, or the like.

Pathological conditions that are amenable to prevention and/or treatment with the invention's methods include any pathological condition whose development or progression in a tissue involves angiogenesis. The invention's methods offer a therapeutic approach to the management of these exemplary diseases and other diseases which are associated with angiogenesis that is controlled by integrin $\alpha4\beta1$.

Exemplary pathological conditions include, for example, solid tumor cancers, solid tumor metastases, angiofibromas, skin cancer, retrolental fibroplasia, Kaposi's sarcoma, childhood hemangiomas, diabetic retinopathy, neovascular glaucoma, age related macular degeneration, psoriasis, gingivitis, rheumatoid arthritis, osteoarthritis, ulcerative colitis, Crohn's disease, inflammatory bowel disease, and atheroscrelotic plaques.

Other pathological conditions include those that entail injury to tissue. The term "injured" in reference to a tissue refers to tissue in which the cellular organization of the tissue has been altered as compared to the cellular organization in normal tissue. Such injury may result, for example, from a breaking of the skin tissue (e.g., a cut, slash, laceration) such as accidental cuts or cuts associated with planned surgery, burns, etc. Injured tissues include those any tissue which undergoes angiogenesis as a result of injury, such as lung, breast, prostate, cervical, pancreatic, colon, ovarian, stomach, esophagus cancer, mouth cancer, tongue cancer, gum, muscle, etc. In particular, skin injury that is associated with undesirable angiogenesis and the formation of scar tissue is particularly amenable to the invention's therapeutic approaches.

Disclosed herein are methods for inhibiting angiogenesis, tumors and metastases in a mouse model (Example 11), a nude mouse model (Examples 6 and 10), a SCID mouse model (Example 7), and a chick CAM model (Example 9). Also disclosed herein are methods for inhibiting angiogenesis in arthritis disease using mouse and rabbit models (Example 13), and in ocular disease using mouse and rabbit models (Example 14).

An agent useful for detecting or inhibiting angiogenesis associated with $\alpha4\beta1$ integrin expression, or a pharmaceutical composition thereof containing the agent, can be used for treating any pathological condition that is characterized, at least in part, by such angiogenesis. One skilled in the art would know that the agent can be administered by various routes including, for example, orally, intranasally, or parenterally, including intravenously, intramuscularly, subcutaneously, intraorbitally, intracapsularly, intrasynovially, intraperitoneally, intracisternally or by passive or facilitated absorption through the skin using, for example, a skin patch or transdermal iontophoresis. Furthermore, the agent can be administered by injection, intubation, via a suppository, orally or topically, the latter of which can be passive, for example, by direct application of an ointment or powder containing the agent, or active, for example, using a nasal spray or inhalant. The agent can also be administered as a topical spray, if desired, in which case one component of the composition is an appropriate propellant. The pharmaceutical composition also can be incorporated, if desired, into liposomes, microspheres or other polymer matrices [Gregoriadis, "Liposome Technology," Vol. 1, CRC Press, Boca Raton, Fla. 1984]. Liposomes, for example, which consist of phospholipids or other lipids, are nontoxic, physiologically acceptable and metabolizable carriers that are relatively simple to make and administer. Liposomes are lipid-containing vesicles having a lipid bilayer as well as other lipid carrier particles that can entrap chemical agents. Liposomes may be made of one or more phospholipids, optionally including other materials such as sterols. Suitable phospholipids include phosphatidyl cholines, phosphatidyl serines, and many others that are well known in the art. Liposomes can be unilamellar, multilamellar or have an undefined lamellar structure.

For example, where angiogenesis associated with integrin $\alpha4\beta1$ expression is localized to the retina, the agent can be formulated in a pharmaceutical composition convenient for use as eye drops, which can be administered directly to the eye. In comparison, in an individual suffering from a metastatic carcinoma, the agent in a pharmaceutical composition can be administered intravenously, orally or by another method that distributes the agent systemically.

Agents that inhibit the specific binding of integrin $\alpha4\beta1$ to one or more of its ligands may be administered in conjunction with other therapies. For example, in the case of cancer therapy, the agent may be administered in conjunction with conventional drug therapy and/or chemotherapy that is directed against solid tumors and for control of establishment of metastases. In one embodiment, the agent is administered during or after chemotherapy. In a more preferred embodiment, the agent is administered after chemotherapy, at a time when the tumor tissue will be responding to the toxic assault. The tumor will attempt to induce angiogenesis to recover by the provision of a blood supply and nutrients to the tumor tissue. Such recovery will be thwarted by the administration of agents which inhibit angiogenesis by inhibiting the specific binding of integrin $\alpha 4\beta 1$ to one or more of its ligands. In an alternative embodiment, the agent may be administered after surgery in which solid tumors have been removed as a prophylaxis against future metastases.

An agent is administered in a "therapeutic amount" (i.e., in an amount which is sufficient to achieve a desired result). In particular, a therapeutic amount is that amount which inhibits the specific binding of $\alpha 4\beta 1$ integrin to its specific ligand in a tissue of a subject, and which results in the reduction, delay, or elimination of undesirable pathologic effects in the subject. One of ordinary skill recognizes that a "therapeutically effective" amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

A therapeutic amount may be determined using in vitro and in vivo assays known in the art and disclosed herein. These are exemplified, without limitation, to administering different amounts of the agent to determine inhibition of angiogenesis using the CAM assay (Examples 4 and 8), inhibition of angiogenesis by intravenous administration of the agent into chicks (Example 4), inhibition of angiogenesis in mice or rabbits (Examples 5, 13 and 14), inhibition of tumor growth in nude mice (Example 6) or in SCID mice (Example 7), inhibition of tumor and metastasis growth using the CAM assay (Examples 8 and 9), in nude mouse (Example 10), or in mice which spontaneously develop tumors (Example 11). Generally, an agent antagonist is administered in a dose of about 0.0001 to 100 mg/kg body weight.

The "subject" to whom the agents are administered includes any animal which is capable of developing angiogenesis in a tissue, including, without limitation, human and non-human animals such simians, rodents, ovines, bovines, ruminants, lagomorphs, porcines, caprines, equines, canines, felines, aves, etc. Preferred non-human animals are members of the Order Rodentia (e.g., mouse and rat). Thus, the compounds of the invention may be administered by human health professionals as well as veterinarians.

The agents which inhibit angiogenesis may be applied to any tissue which is capable of developing angiogenesis including, for example, skin, ocular tissue (e.g., retina, macular or cornea), skin, synovial tissue, bone, intestinal tissue, muscle tissue, gut tissue, connective tissue, blood vessels, tumor tissue (including benign and cancer tissue), etc.

B. Inhibiting Endothelial Cell Adhesion and Endothelial Cell Migration

The invention further provides methods for inhibiting endothelial cell adhesion and/or for inhibiting endothelial cell migration by employing an agent that inhibits the specific binding of integrin $\alpha 4\beta 1$ to its ligand. Data provided herein demonstrates that endothelial cell adhesion to, and migration across, CS-1 fibronectin was inhibited using anti-integrin $\alpha 4\beta 1$ antibody (Example 3).

Endothelial cell adhesion and migration are known to regulate endothelial cell survival, proliferation, and motility during new blood vessel growth in normal and pathologic conditions that involve angiogenesis. Thus, the invention's methods for inhibiting endothelial cell adhesion and/or for inhibiting endothelial cell migration are useful in determining the mechanisms that underlie desirable and undesirable angiogenesis, and in inhibiting undesirable angiogenesis in normal angiogenesis processes or in pathologic conditions that are associated with angiogenesis.

The term "endothelial cell adhesion" as used herein refers to the adhesion of an endothelial cell to one or more components of the extracellular matrix (e.g., fibronectin, collagens I-XVIII, laminin, vitronectin, fibrinogen, osteopontin, Del 1, tenascin, von Willebrands's factor, etc.), to a ligand which is expressed on the cell surface (e.g., VCAM, ICAM, LI-CAM, VE-cadherin, integrin a2, integrin a3, etc.) and/or to another cell (e.g., another endothelial cell, to a fibroblast cell, stromal cell, tumor cell, etc.) The terms "inhibiting endothelial cell adhesion" and "reducing endothelial cell adhesion" refer to reducing the level of adhesion of an endothelial cell to one or more components of the extracellular matrix (e.g., fibronectin, collagens I-XVIII, laminin, vitronectin, fibrinogen, osteopontin, Del 1, tenascin, von Willebrands's factor, etc.), and/or to another cell (e.g., another endothelial cell, fibroblast cell, stromal cell, tumor cell, etc.) to a quantity which is preferably 10% less than, more preferably 50% less than, yet more preferably 75% than, even more preferably 90% less than, the quantity in a corresponding control endothelial cell, and most preferably is at the same level which is observed in a control endothelial cell. A reduced level of endothelial cell adhesion need not, although it may, mean an absolute absence of cell adhesion. The invention does not require, and is not limited to, methods that wholly eliminate cell adhesion. The level of endothelial cells adhesion may be determined using methods well known in the art, including those disclosed herein (Example 3).

The term "endothelial cell migration" as used herein refers to the translocation of an endothelial cell across one or more components of the extracellular matrix (e.g., fibronectin, collagens I-XVIII, laminin, vitronectin, fibrinogen, osteopontin, Del 1, tenascin, von Willebrands's factor, etc.), or along the surface of another cell (e.g., another endothelial cell, fibroblast cell, stromal cell, tumor cell, etc.).

The terms "inhibiting endothelial cell migration" and "reducing endothelial cell migration" refer to reducing the level of migration of an endothelial cell to a quantity which is preferably 10% less than, more preferably 50% less than, yet more preferably 75% less than, and even more preferably 90% less than, the quantity in a corresponding control endothelial cells, and most preferably is at the same level which is observed in a control endothelial cell. A reduced level of endothelial cell migration need not, although it may, mean an absolute absence of cell migration. The invention does not require, and is not limited to, methods that wholly eliminate cell migration. The level of endothelial cells migration may be determined using methods well known in the art, such as time lapse video microscopy, scratch type wound assay, and methods disclosed herein (Example 3).

C. Detecting Angiogenesis

The invention additionally provides methods for detecting angiogenesis which involve the use of an agent which specifically binds to integrin $\alpha 4\beta 1$ polypeptides or to integrin α4β1 mRNA. Such a method is useful for identifying the presence of angiogenesis in various tissues, including, for example, normal tissues such as embryonic tissue or placental tissue, granulation tissue, and a tissue involved in a pathological condition. As such, the invention further provides methods of diagnosing a pathological condition characterized by angiogenesis associated with integrin α4β1 expression in a tissue in an individual.

Data provided herein demonstrate using immunohistochemical analysis that human melanoma cells are characterized by expression of integrin α4β1 (Example 2). However, the invention is not restricted to the detection of melanoma cells. Rather, any pathological condition, which is characterized by angiogenesis associated with integrin α4β1 expression, can be identified by the invention's methods. For example, angiognesis in a tissue may be detected by detecting the presence of integrin α4β1 polypeptide using Western blot analysis or immunofluorescence. Alternatively, angiognesis in a tissue may be detected by detecting the presence of integrin α4β1 mRNA using reverse transcription polymerase chain (RT-PCR), or in situ hybridization. These methods are well known and well within the ordinary skill of those in the art.

In one embodiment, the agent which is used in detecting the presence of integrin α4β1 polypeptide and/or mRNA can be detectably labeled, for example, by linking the agent to a moiety, which is selected based, for example, on whether specific binding of the agent is to be detected in vivo or whether a tissue to which the agent is suspected of binding is to be removed (e.g., by biopsy) and examined ex vivo.

A moiety useful for labeling an agent antagonist can be a radionuclide, a paramagnetic material, an X-ray attenuating material, a fluorescent, chemiluminescent or luminescent molecule, a molecule such as biotin, or a molecule that can be visualized upon reaction with a particular reagent, for example, a substrate for an enzyme or an epitope for an antibody. The moiety can be linked to an agent using well known methods, which are selected, in part, based on the chemical nature of the agent and the moiety. For example, where the moiety is an amino acid sequence such as a hexahistidine (His6) sequence, and the agent is a peptide, the His6 sequence can be synthesized as part of the peptide, and the His6-labeled agent can be identified by the binding of a nickel ion reagent to the His6 moiety.

Methods for chemically linking a moiety to an agent also can be utilized. For example, methods for conjugating polysaccharides to peptides are exemplified by, but not limited to coupling via alpha- or epsilon-amino groups to NaIO$_4$-activated oligosaccharide, using squaric acid diester (1,2-diethoxycyclobutene-3,4-dione) as a coupling reagent, coupling via a peptide linker wherein the polysaccharide has a reducing terminal and is free of carboxyl groups (U.S. Pat. No. 5,342,770), coupling with a synthetic peptide carrier derived from human heat shock protein hsp65 (U.S. Pat. No. 5,736,146), and using the methods of U.S. Pat. No. 4,639,512. Methods for conjugating proteins to proteins include coupling with a synthetic peptide carrier derived from human heat shock protein hsp65 (U.S. Pat. No. 5,736,146), the methods used to conjugate peptides to antibodies (U.S. Pat. Nos. 5,194,254; 4,950,480), the methods used to conjugate peptides to insulin fragments (U.S. Pat. No. 5,442,043), the methods of U.S. Pat. No. 4,639,512, and the method of conjugating the cyclic decapeptide polymyxin B antibiotic to and IgG carrier using EDAC [1-ethyl-3-(3-dimethylaminopropyl)carbodiimide]-mediated amide formation [Drabick et al. (1998) Antimicrob. Agents Chemother. 42:583-588]. Approaches to conjugate nucleic acids to proteins are also known in the art, such as those described in U.S. Pat. Nos. 5,574,142; 6,117,631; 6,110,687; each of is incorporated in its entirety by reference. Methods for conjugating lipids to peptides have been described in the art including, but not limited to, the use of reductive amination and an ether linkage which contains a secondary or tertiary amine (U.S. Pat. No. 6,071,532), the methods of U.S. Pat. No. 4,639,512, the methods used for covalently coupling peptides to unilamellar liposomes [Friede et al. (1994) Vaccine 12:791-797], of coupling human serum albumin to liposomes using the hetero-bifunctional reagent N-succinimidyl-S-acetylthioacetate (SATA) [Kamps et al. (1996) Biochim. Biophys. Acta 1278:183-190], of coupling antibody Fab' fragments to liposomes using a phospholipid-poly(ethylene glycol)-maleimide anchor [Shahinian et al. (1995) Biochim. Biophys. Acta 1239:157-167], and of coupling *Plasmodium* CTL epitope to palmitic acid via cysteine-serine spacer amino acids [Verheul et al. (1995) J. Immunol. Methods 182:219-226].

A specifically bound agent can be detected in an individual using an in vivo imaging method, such as a radionuclide imaging, positron emission tomography, computerized axial tomography, X-ray or magnetic resonance imaging method, or can be detected using an ex vivo method, wherein, following administration, a sample of the tissue is obtained from the individual, and specific binding of the agent in the sample is detected (e.g., by immunohistochemical analysis; Example 3).

An agent that is specifically bound to α4β1 integrin in a sample can be detected directly by detecting the agent, or indirectly by detecting the presence of a moiety such as by detecting radioactivity emitted by a radionuclide moiety. Specifically bound agent also can be detected indirectly by further contacting it with a reagent that specifically interacts with the agent, or with a moiety linked to the agent, and detecting interaction of the reagent with the agent or label. For example, the moiety can be detected by contacting it with an antibody that specifically binds the moiety, particularly when the moiety is linked to the agent. The moiety also can be, for example, a substrate, which is contacted by an enzyme that interacts with and changes the moiety such that its presence can be detected. Such indirect detection systems, which include the use of enzymes such as alkaline phosphatase, horseradish peroxidase, beta-galactosidase and the like, are well known in the art and commercially available, as are the methods for incorporating or, linking the particular moiety to a particular type of agent.

D. Screening Compounds

The invention further provides methods for identifying compounds which are capable of inhibiting angiogenesis, inhibiting endothelial cells adhesion, and/or inhibiting endothelial cell migration.

A screening assay of the invention can be performed by contacting a tissue exhibiting angiogenesis associated with integrin α4β1 expression with a test compound, and detecting inhibition of angiogenesis in the tissue, thereby identifying the compound as inhibiting angiogenesis associated with α4β1 integrin expression. A tissue can be contacted with the agent in vivo or ex vivo (see, for example, U.S. Pat. No. 5,622,699, incorporated by reference). Where a screening method of the invention is performed using an in vitro format, it can be adapted to automated procedure, thus allowing high throughput screening assays for examining libraries of molecules to identify potential α4β1 antagonists, which can reduce or inhibit angiogenesis associated with α4β1 expression. The tissue can be any tissue that undergoes angiogenesis associated with α4β1 integrin expression, for example, malignant tumor tissue.

Alternatively, a screening assays is carried out by contacting endothelial cells with a test compound, and detecting inhibition of endothelial cell adhesion and/or of endothelial cell migration, thereby identifying the compound a inhibiting endothelial cell adhesion and/or endothelial cell migration.

Methods for preparing libraries of molecules, which can be screened using a method of the invention to identify α4β1 antagonists that inhibit angiogenesis, endothelial cells adhesion and/or endothelial cell migration processes which are associated with α4β1 expression, are known in the art. These are exemplified by methods for preparing oligonucleotide libraries (Gold et al., U.S. Pat. No. 5,270,163, incorporated by reference); peptide libraries (Koivunen et al., supra, 1993, 1994); peptidomimetic libraries (Blondelle et al., Trends Anal. Chem. 14:83-92 (1995)) oligosaccharide libraries (York et al., Carb. Res. 285:99-128 (1996); Liang et al., Science 274:1520-1522 (1996); and Ding et al., Adv. Expt. Med. Biol. 376:261-269 (1995)); lipoprotein libraries (de Kruif et al., FEBS Lett., 399:232-236 (1996)); glycoprotein or glycolipid libraries (Karaoglu et al., J. Cell Biol. 130:567-577 (1995)); or chemical libraries containing, for example, drugs or other pharmaceutical agents (Gordon et al., J. Med. Chem. 37:1385-1401 (1994); Ecker and Crook, Bio/Technology 13:351-360 (1995), U.S. Pat. No. 5,760,029, incorporated by reference). Libraries of diverse molecules also can be obtained from commercial sources.

E. Isolating Endothelial Cell Progenitors

The invention further provides a method for isolating endothelial cell progenitors from a tissue by treating a tissue which contains endothelial cell progenitors with an agent capable of binding to integrin α4β1 and isolating endothelial cell progenitors to which the agent binds. These methods are based, in part, on the inventor's discovery that endothelial cells which are involved in angiogenesis express integrin α4β1.

The term "endothelial cell progenitor" as used herein refers to an endothelial cell which expresses cell surface markers that are characteristic of these cells as understood in the art. For example, human endothelial cell progenitors express the surface molecules CD34, flk-1, and/or tie-2 [Isner et al., U.S. Pat. No. 5,980,887, the entire contents of which are herein incorporated by reference]. Mouse endothelial cell progenitors express the TM gene, tie-2 gene, and/or fgf3 gene, and/or stain with the GSL I B4 lectin [Hatzopoulos et al. (1998) Development 125:1457-1468].

Endothelial cell progenitors that are isolated in accordance with the invention's methods are useful in regulating angiogenesis [Isner et al., U.S. Pat. No. 5,980,887, incorporated by reference]. Heterologous, homologous, and autologous endothelial cell progenitor grafts incorporate in vivo into sites of active angiogenesis or blood vessel injury (i.e., they selectively migrate to such locations [Isner et al., U.S. Pat. No. 5,980,887]).

Thus, in one embodiment, the endothelial cell progenitors can be used to enhance angiogenesis or to deliver an angiogenesis modulator (e.g., anti- or pro-angiogenic agents, respectively), to sites of pathologic or utilitarian angiogenesis. Additionally, in another embodiment, endothelial cell progenitors can be used to induce re-endothelialization of an injured blood vessel, and thus reduce restenosis by indirectly inhibiting smooth muscle cell proliferation [Isner et al., U.S. Pat. No. 5,980,887].

In one preferred embodiment, the endothelial cells can be used alone to potentiate a patient for angiogenesis. Some patient populations, typically elderly patients, may have either a limited number of endothelial cells or a limited number of functional endothelial cells. Thus, if one desires to promote angiogenesis, for example, to stimulate vascularization by using a potent angiogenesis such as VEGF, such vascularization can be limited by the lack of endothelial cells. However, by administering the endothelial cell progenitors one can potentiate the vascularization in those patients.

Because endothelial cell progenitors home to foci of angiogenesis, these cells are also useful as autologous vectors for gene therapy and diagnosis of ischemia or vascular injury. For example, these cells can be utilized to inhibit as well as augment angiogenesis. For anti-neoplastic therapies, for example, endothelial cell progenitors can be transfected with or coupled to cytotoxic agents, cytokines or co-stimulatory molecules to stimulate an immune reaction, other anti-tumor drugs, or angiogenesis inhibitors. For treatment of regional ischemia, angiogenesis could be amplified by prior transfection of endothelial cell progenitors to achieve constitutive expression of angiogenic cytokines and/or selected matrix proteins. In addition, the endothelial cell progenitors may be labeled (e.g., radiolabeled), administered to a patient and used in the detection of ischemic tissue or vascular injury.

Autologous endothelial cell progenitor transplants have been successfully used, and endothelial cell progenitors have been shown to be easily manipulated and expanded ex vivo [Isner et al., U.S. Pat. No. 5,980,887; U.S. Pat. No. 5,199,942, the disclosure of which is incorporated by reference].

Endothelial cell progenitors are present in a number of tissues including, for example, peripheral blood, bone marrow, and umbilical cord blood. Endothelial cell progenitors may be isolated in accordance with the invention's methods by treating a tissue (e.g., peripheral blood, bone marrow, umbilical cord blood, etc.) which contains endothelial cell progenitors with an antibody which is capable of specific binding to at least a portion of integrin α4β1 polypeptide, followed by isolating cells which bind to the antibody. The endothelial cell progenitor nature of the isolated cells may be confirmed by determining the presence of endothelial cell progenitor-specific antigens (e.g., CD34, flk-1, and/or tie-2) on the surface of the isolated cells using commercially available antibodies to these antigens. It may be desirable, but not necessary, to expand endothelial cell progenitors in vivo prior to treating the tissue that contains endothelial cell progenitors by administration of recruitment growth factors (e.g., GM-CSF and IL-3) to the patient.

Once isolated in accordance with the invention's methods, these compositions may be administered to a patient to treat a number of conditions including, for example, unregulated angiogenesis or blood vessel injury. The cells may also be stored in cryogenic conditions. Optionally, the cells may be expanded ex vivo using, for example, the method disclosed by U.S. Pat. No. 5,541,103, the disclosure of which is incorporated by reference.

The endothelial cell progenitors are administered to the patient by any suitable means, including, for example, intravenous infusion, bolus injection, and site directed delivery via a catheter. Preferably, the progenitor cells obtained from the patient are readministered. Generally, from about $10^6$ to about $10^{18}$ progenitor cells are administered to the patient for transplantation.

In one embodiment, various genetic material may be delivered to the endothelial cell progenitors. The genetic material that is delivered to the endothelial cell progenitors may be genes, for example, those that encode a variety of proteins including anticancer agents. Such genes include those encoding various hormones, growth factors, enzymes, cytokines, receptors, MHC molecules and the like. The term "genes" includes nucleic acid sequences both exogenous and endogenous to cells into which a virus vector, for example, a pox virus such as swine pox containing the human TNF gene may be introduced. Additionally, it is of interest to use genes encoding polypeptides for secretion from the endothelial cell progenitors so as to provide for a systemic effect by the protein encoded by the gene. Specific genes of interest include those encoding TNF, TGF-α, TGF-β, hemoglobin, interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, factor VIII, factor IX, PDGF, EGF, NGF, EPO, β-globin, endothelial cell mitogens and the like, as well as biologically active modifications of these proteins. The gene may further encode a product that regulates expression of another gene product or blocks one or more steps in a biological pathway. In addition, the gene may encode a toxin fused to a polypeptide (e.g., a receptor ligand), or an antibody that directs the toxin to a target, such as a tumor cell. Similarly, the gene may encode a therapeutic protein fused to a targeting polypeptide, to deliver a therapeutic effect to a diseased tissue or organ.

In another embodiment, the endothelial cell progenitors can also be used to deliver genes to enhance the ability of the immune system to fight a particular disease or tumor. For example, the cells can be used to deliver one or more cytokines (e.g., IL-2) to boost the immune system and/or one or more antigens.

In yet another embodiment, the endothelial cell progenitors may also be used to selectively administer drugs, such as an antiangiogenesis compound such as O-chloroacetyl carbamoyl fumagillol (TNP-470). Preferably, the drug would be incorporated into the cell in a vehicle such as a liposome, a timed released capsule, etc. The endothelial cell progenitor would then selectively target a site of active angiogenesis such as a rapidly growing tumor where the compound would be released. By this method, one can reduce undesired side effects at other locations.

In a further embodiment, the endothelial cell progenitors may be used to enhance blood vessel formation in ischemic tissue (i.e., a tissue having a deficiency in blood as the result of an ischemic disease). Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia. Methods for inducing the formation of new blood vessels in ischemic tissue are disclosed in Isner et al., U.S. Pat. No. 5,980,887, herein incorporated by reference.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); A1 (microliters); cm (centimeters); mm (millimeters); μm (micrometers); nm (nanometers); ° C. (degrees Centigrade); U (units), mU (milliunits); min. (minutes); sec. (seconds); % (percent); FITC (fluorescein isothiocyanate); H & E (haematoxylin and eosin); and (Ig) immunoglobulin.

Example 1

Inhibition of Angiogenesis by Anti-Fibronectin Antibody

Angiogenesis was stimulated on the surface of the chick chorioallantoic membrane ("CAM") by applying a 5 mm filter disk on the CAM saturated with basic fibroblast growth factor ("bFGF"), vascular endothelial growth factor ("VEGF"), interleukin 8 ("IL-8"), tumor necrosis factor alpha ("TNF-α") or saline. Twenty four hours after angiogenesis had been stimulated saline, 25 μg control IgG, 25 μg of an antibody directed against the cell binding peptide of fibronectin (Anti-CPB), 25 μg of an antibody directed against the fibronectin C-terminus (Anti-CT), 25 lag of an antibody directed against the cell binding peptide of fibronectin (Anti-CBP) or 25 μg of an antibody directed against vitronectin (Anti-VN) were applied to the CAM of eight to ten eggs each in a volume of 25 μl. Forty eight hours after this, CAMs were excised from the egg and the number of blood vessels in each filter disk were counted. The results are shown in FIG. 1A. These results demonstrate that antibody directed against the fibronectin C-terminus (Anti-CT) inhibited angiogenesis.

In another experiment, twenty four hours after angiogenesis had been stimulated, saline 25 μg control IgG, of 25 μg of monoclonal antibodies directed against the C-terminal CS-1 or heparin binding regions of fibronectin were applied. Forty eight hours after this, CAMs were excised from the egg and the number of blood vessels in each filter disk were counted. Each experiment was performed at least three times. The results are shown in FIG. 1B. These results demonstrate that antibodies directed against the C-terminal CS-1 or heparin binding regions of fibronectin inhibited angiogenesis.

These initial studies of the role of fibronectin in angiogenesis revealed that the C-terminus of fibronectin was critical for angiogenesis. Antibody inhibitors of the C-terminus of fibronectin showed that this region of fibronectin plays a role in angiogenesis. As this region of fibronectin interacts with integrin α4β1, the inventor hypothesized that this integrin regulated angiogenesis (FIG. 1A). In addition, antibodies that bind to secondary integrin α4β1 binding sites in the C-terminus of fibronectin and antibodies that bind to nearby heparin binding sites in the C-terminus of fibronectin also blocked angiogenesis (FIG. 1B), confirming the inventor's hypothesis.

Example 2

Immunohistochemical Analysis of Integrin α4β1 Expression in Normal and Tumor Tissue Five micron frozen sections of human normal thymus (FIG. 2A) and melanoma (FIG. 2B) were fixed for 2 minutes in acetone, air dried and rehydrated for 5 minutes in phosphate buffered saline. Sections were then blocked for 2 hours in a 2% bovine serum albumin in phosphate buffered saline and incubated with 5 μg/ml anti-α4β1 monoclonal antibody and anti-von Willebrand Factor (a marker of endothelial cells used by pathologists to identify blood vessels) polyclonal antibody for one hour room temperature. Sections were washed in PBS and incubated in 1:400 dilution of goat anti-rabbit-FITC and in goat anti-mouse-rhodamine for 1 hour at room temperature. Slides were well washed, and coverslips were mounted in one drop of Fluoromount, prior to photography under fluorescent illumination. Blood vessels positive vWF (von Willebrand Factor) only are green, cells positive for integrin α4β1 only are red and blood vessels positive for both are yellow.

The results in FIG. 2 demonstrate that integrin α4β1 expression is minimal on blood vessels present in normal human tissues (FIG. 2A) or in unstimulated CAM tissues (results not shown). Integrin α4β1 is expressed on the lymphocytes in lymph nodes, as is well accepted. Integrin α4β1 expression is dramatically upregulated on blood vessels in tumor tissues such as in malignant melanoma (FIG. 2B) and in CAM tissue in response to angiogenic growth factors such as basic fibroblast growth factor (results not shown).

Example 3

Inhibition of Human Neonatal Cell Adhesion to, and Migration of Human Vascular Endothelial Cells on, CS-1 Fibronectin by Anti-Integrin α4β1 Antibody 1. Endothelial Cell Adhesion:

The wells of 48 well culture dishes were coated with 10 μg/ml CS-1 fibronectin for one hour at 37° C. and blocked with 2% bovine serum albumin in phosphate buffered saline for one hour. Fifty thousand cells in 250 μl of adhesion buffer were added in triplicate to wells containing 250 μl of a solution of 50 μg/ml of an anti-α4β1 blocking antibody in adhesion buffer, 50 μg/ml of control antibody in adhesion buffer or adhesion buffer (Hepes buffered Hanks balanced salt solution, HBSS). Human neonatal umbilical vein endothelial cells were allowed to adhere to dishes for ten to twenty minutes at 37° C. Nonadherent cells were removed by washing each well four times with 500 μl of adhesion buffer. Adherent cells were then fixed for 15 minutes with 3.7% paraformaldehyde in phosphate buffered saline and stained with a 2% crystal violet solution. After extensive water washing to remove excess crystal violet, plates were dried overnight. Crystal violet was extracted by incubation for 15 minutes in 10% acetic acid and absorbance at 650 nm determined as an indicator of number of cells bound. The results are shown in FIG. 3A.

These results demonstrate that inhibitors of integrin α4β1 blocked the adhesion of proliferating human neonatal umbilical vein endothelial cells to CS-1 fibronectin (FIG. 3).

2. Endothelial Cell Migration:

The lower side of 8 μm pore transwell inserts were coated with 5 μg/ml of CS-1 fibronectin (B) for one hour and were blocked with 2% bovine serum albumin in phosphate buffered saline for one hour. The inserts were then placed into 24 culture dishes containing 500 μl migration buffer in the lower chamber. Twenty-five thousand human vascular endothelial cells (HUVECS) in 50 μl of migration buffer were added to the upper chamber of duplicate inserts containing 50 μl of a solution of 50 μg/ml of an anti-α4β1 function blocking antibody in migration buffer, 50 μg/ml of control antibodies or migration buffer alone. Cells were allowed to migrate from the upper to the lower chamber for four hours at 37° C. Nonmigratory cells were removed from the upper surface by wiping the upper side with an absorbent tip. Cells which had migrated to the lower side of the transwell insert were then fixed for 15 minutes with 3.7% paraformaldehyde in phosphate buffered saline and stained with a 2% crystal violet solution. After extensive water washing to remove excess crystal violet, the number of cells that had migrated was counted in three representative high power fields per insert. The results are shown in FIG. 3B.

These results demonstrate that inhibitors of integrin α4β1 blocked the migration of human vascular endothelial cells to CS-1 fibronectin (FIG. 3B).

Example 4

Inhibition of Angiogenesis In Ovo in Chick Chorioallantoic Membrane, and In Vivo in Chicks, by Anti-Integrin α4β1 Antibody 1. Chick Chorioallantoic Membrane Model Angiogenesis was stimulated on the surface of the chick chorioallantoic membrane (CAM) by applying a 5 mm filter disc saturated with basic fibroblast growth factor (FIG. 4A), vascular endothelial growth factor (FIG. 4B), interleukin 8 (FIG. 4C), tumor necrosis alpha (FIG. 4D) or saline saturated filter disk on the CAM. Twenty-four hours after angiogenesis had been stimulated saline, 10 μg control IgG, and 10 μg anti-α4β1 monoclonal antibody with reactivity against chick cells were applied to the CAM of eight to ten eggs each in a volume of 25 μl. Forty-eight hours after this, CAMs were excised from the egg and the number of blood vessel branch points within the 5 mm area were counted.

Figure 4:
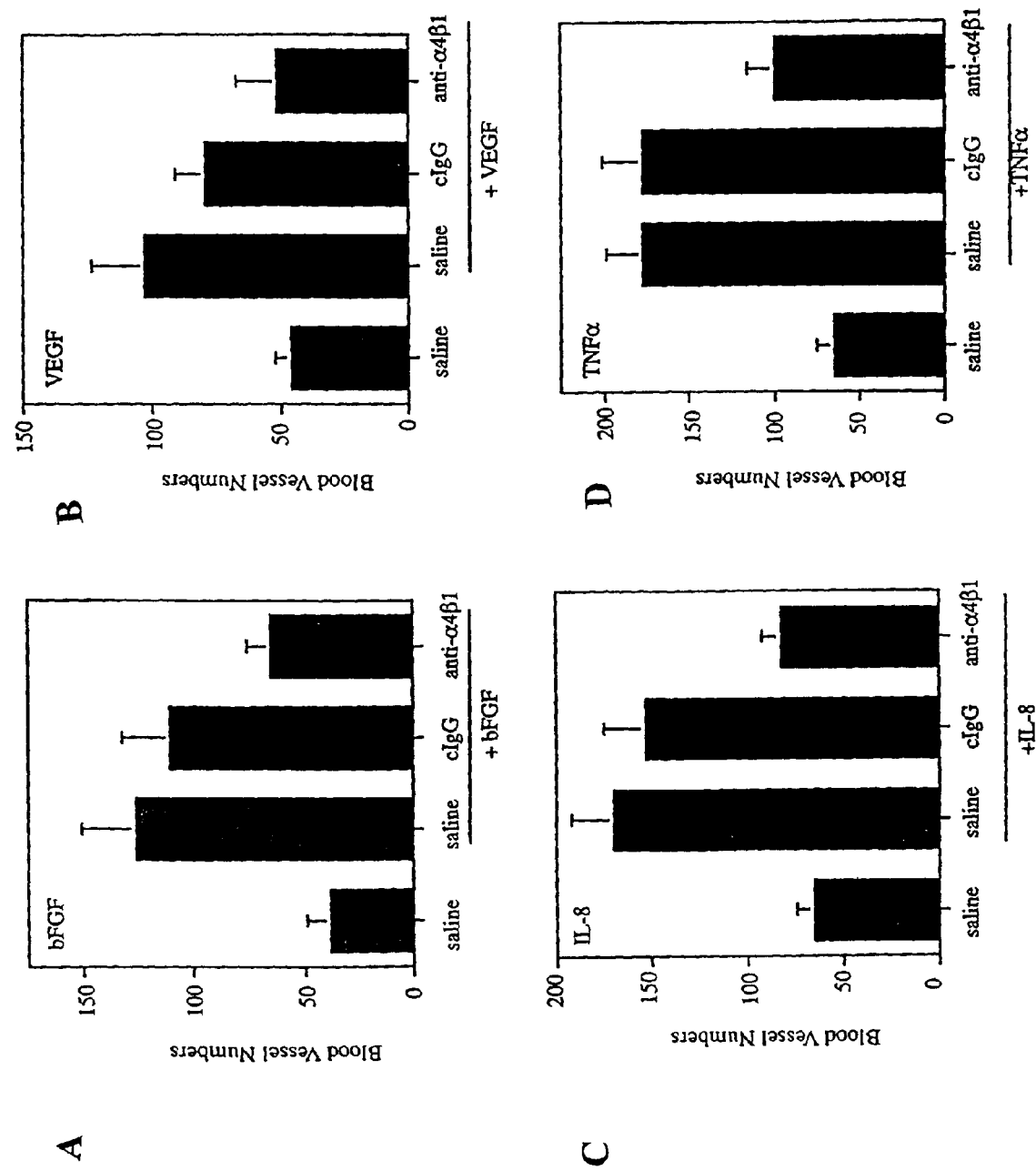
FIG. 4 shows inhibition of angiogenesis by anti-integrin α4 antibody antagonists in chick chorioallantoic membrane (CAM) treated with basic fibroblast growth factor (A), vascular endothelial growth factor (B), interleukin 8 (C), or tumor necrosis alpha (D).

The data in FIG. 4 demonstrates the inhibition of angiogenesis in chick chorioallantoic membrane (CAM) by anti-integrin α4 antibody. Furthermore, inhibition was dose-dependent (data not shown).

2. In Vivo Inhibition in Chicks

The inventor subsequently tested anti-integrin α4β1 monoclonal antibody, saline, and control IgG for their abilities to inhibit angiogenesis by intravenous injection into the chick vasculature using this same cytokine stimulated filter disk model. Indeed, when injected into the bloodstream, these reagents inhibited angiogenesis, demonstrating that the integrin α4β1 is directly present on the vasculature.

Example 5

Inhibition of Murine Angiogenesis by Antibody and Peptide Agonists to Integrin α4β1

Angiogenesis was induced by subcutaneous injection of 400 μl of growth factor depleted matrigel supplemented 0.4 μg/ml bFGF and saline, 25 μg/ml function blocking anti-α4β1 antibodies or control antibodies. Alternatively, mice were injected with matrigel containing bFGF and 1 mM of the sequence EILDVPST (SEQ ID NO:52) or the control sequence EILEVPST (SEQ ID NO:53). After 72 hours, mice were injected with Bandiera Simplicifolia lectin-FITC conjugate. After 15 minutes, matrigel plugs were excised and homogenized. Fluorescence intensity within the lysed plug was determined and correlated with degree of angiogenesis as determined by standard immunohistochemical analyses. The results are shown in FIG. 5.

FIG. 5 demonstrates that growth factor-stimulated angiogenesis in the mouse model is selectively and specifically inhibited both by anti-integrin α4β1 antibody and by the peptide sequence EILDVPST, and not by control antibodies and peptides. This demonstrates that inhibition of integrin α4β1 function using antagonists of integrin α4β1 ligand binding results in the suppression of angiogenesis.

Example 6

Inhibition of Angiogenesis and Tumor Growth in vivo using a Nude Mouse Tumor Model

Integrin α4β1 inhibitors can be used to inhibit tumor growth, as in immunocompromised mouse tumor growth models. In this model, tumor cells (such as carcinomas of any tissue of origin, melanomas, sarcomas or lymphomas) are injected subcutaneously in nude mice. Mice are then treated (e.g., daily, every other day, weekly, monthly, etc.) by intravenous, intraperitoneal or subcutaneous injection of integrin α4β1 inhibitors such as 200 μg rat anti-mouse α4β1, peptide or small molecule antagonists, control immunoglobulin or saline. Tumor growth is monitored by measurement with calipers every weekday. The experiment is continued for four to eight weeks. Tumors are excised and weighed. Representative tumors are photographed using a stereo microscope. Tumors are fixed in neutral buffered formalin, sectioned and H&E stained. Other tumors are flash frozen and sectioned for immunohistochemical detection and quantification of blood vessels. Integrin α4β1 inhibitors are expected to inhibit tumor growth in this model while control substances are not expected to inhibit tumor growth. All data are analyzed for statistical significance using Student's T-test and Wilcox rank mean sum analyses.

Example 7

Inhibition of Angiogenesis and Tumor Growth in vivo Using a SCID Mouse Tumor Model

Six-week old Balb/c SCID mice are anesthetized, shaved and swabbed with alcohol. An 8 mm by 13 mm section of dorsal skin is removed down to the fascia. A similar-sized piece of full thickness neonatal foreskin is placed on the wound bed and sutured into place. The transplantation site is covered with an adhesive bandage and allowed to heal for four weeks. After four weeks, the human skin is inoculated intradermally with human tumor cells or with growth factor-depleted Matrigel containing angiogenic growth factors. Animals are then injected (e.g., daily, every other day, weekly, monthly, etc.) intravenously or intraperitoneally with α4β1 antagonists, such as 200 μg mouse anti-human integrin α4β1 antibody, peptide or small molecule antagonists, control substances or saline. Animals bearing tumors are treated for up to four weeks. Tumor size is monitored throughout the period. Tumor mass data is analyzed for statistical significance using Student's T-test and Wilcox Rank mean sum analyses. Representative tumors are analyzed for induction of angiogenesis by immunohistochemical methods after preparation of frozen sections. Vascular density is assessed on all sections by staining for expression of the endothelial marker CD31 in a blinded fashion. Tumors are also be evaluated by hematoxylin and eosin staining and by Ki67 and apoptag staining to determine the impact of treatments on tumor cell fate. All data are analyzed for statistical significance using Student's T-test and Wilcox rank mean sum analyses.

Example 8

Inhibition of Angiogenesis and Tumor Growth Using an In Ovo Chick Chorioallantoic Membrane Tumor Model

Integrin α4β1 inhibitors can also be used to inhibit tumor growth on the chick chorioallantoic membrane. 50 mg fragments of human tumors are placed on chick chorioallantoic membranes. Eggs are then injected with integrin-α4β1 inhibitors, with saline or control substances. Tumors grow for one week, then tumors are excised and weighed. Representative tumors are photographed using a stereo microscope. Tumors are fixed in neutral buffered formalin, sectioned and H&E stained. Other tumors are flash frozen and sectioned for immunohistochemical detection and quantification of blood vessels. Integrin α4β1 inhibitors are expected to inhibit tumor growth in this model while control substances are not expected to inhibit tumor growth. All data are analyzed for statistical significance using Student's T-test and Wilcox rank mean sum analyses.

Example 9

Inhibition of Metastases Using an In Ovo Chick Chorioallantoic Membrane Tumor Model

Fifty mg fragments of tumors are placed on fresh CAMS. Eggs are then injected with integrin-α4β1 inhibitors, with saline or control substances. Original tumor weights are determined after 7 days. Tumor metastases to the embryonic lung and other tissues are quantified after 7 days by preparing a single cell suspension of the lung and other tissues. Flow cytometry analysis with antibodies specific for human cell surface markers, such as W6/32, are performed to quantify tumor metastasis.

Example 10

Inhibition of Metastases Using an In Vivo Nude Mouse Tumor Model

Tumor cells are inoculated intravenously, subcutaneously, or orthotopically (i.e., in the appropriate tissue of origin) in nude mice. Mice are treated with integrin-α4β1 inhibitors, with saline or control substances. Primary tumors are removed after three weeks of growth to allow metastases to grow for an additional five. The numbers and sizes of metastases to lung and liver are assessed at this end point. All data are analyzed for statistical significance using student's t-test, Wilcox rank mean sum and power analyses.

Example 11

Inhibition of Spontaneous Tumors and Metastases in an In Vivo Mouse Tumor Model

Tumors arise spontaneously in several strains of mice. Integrin α4β1 inhibitors are used to inhibit tumor growth in many of these. Mtag and APC mice are excellent models of spontaneous tumor growth and metastasis. MTAG female mice carrying the polyoma middle T-oncogene (PyV+/−) transgene bear detectable mammary carcinoma tumors measuring 2-4 mm in all mammary glands. APC mice develop multiple colon polyps. Up to ten mice per group will be enrolled in this study. Mice receive intravenous or intraperitoneal injections of putative antibody, peptide and small molecule antagonists of integrin α4β1 or fibronectin. In each experiment the compounds consist of at least one putative angiogenesis inhibitor and one matched control compound and are administered in a blinded fashion. Tumor dimensions and tumor number are measured every other day where palpable. Mouse weight is measure daily. After up to 30 days of treatment, mice are euthanized, photographed if necessary and tumors surgically resected. In addition, lungs and liver are surgically resected. Tumors are weighed. Metastatic nodules on lungs and liver are counted. Portions of representative tumors or lungs are frozen. Frozen sections are stained with antibodies directed CD31 and Factor VIII related antigen to obtain an indication of angiogenic index.

Example 12

Inhibition of Endothelial Progenitor Cell Migration in In Vivo Mouse and Rat Animal Models Integrin α4β1 inhibitors can be used to prevent endothelial cell precursors from exiting the blood stream and entering sites of neovascularization. Angiogenesis assay are performed in mouse or nude rats transplanted with murine Tie2-LacZ bone marrow by injecting matrigel, a viscous extracellular matrix that solidifies at body temperature, containing angiogenic growth factors. Mice are treated by intravenous injection with anti-murine α4β1 and control antibodies or other inhibitors of α4β1. α4β1 inhibitors are anticipated to block LacZ staining cells from incorporating into blood vessels, indicating that α4β1 regulates endothelial precursor cell egress from the circulation. Frozen sections of the matrigel are stained with antibodies directed CD31 and Factor VIII related antigen to obtain an indication of angiogenic index.

Example 13

Inhibition of Angiogenesis In Vivo in a Rabbit and Mouse Animal Models of Arthritis Antigen induced arthritis is induced in rabbits or mice by multiple subcutaneous injections of ovalbumin in Freund's complete adjuvant, followed by booster injections in Freund's incomplete adjuvant two weeks later. Arthritis is induced one week later by intra-articular injection of ovalbumin with basic fibroblast growth factor. After arthritis induction, animals are treated intra-articularly or systemically with anti-murine α4β1 and control antibodies or other inhibitors of α4β1. Frozen sections of joints are stained with antibodies directed CD31 and Factor VIII related antigen to obtain an indication of angiogenic index.

Example 14

Inhibition of Angiogenesis In Vivo in Rabbit and Mouse Animal Models of Ocular Angiogenesis Hydron pellets containing Carafate-stabilized growth factors such as bFGF or VEGF and integrin α4β1 inhibitors or control substances are surgically implanted into rabbit or mouse corneas and observed daily for 10-15 days. Photographs are taken periodically after implantation. Angiogenesis is quantified by determining the mean area of neovascularization.

Example 15

Antagonists of α4β1 Block Murine bFGF and VEGF Induced Angiogenesis

Figure 18:
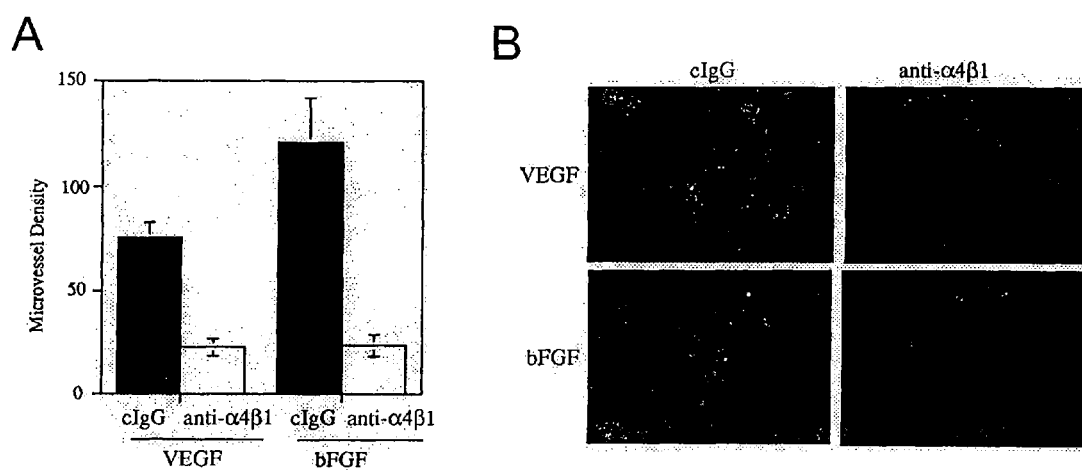
FIG. 18 shows a graph of microvessel density versus antibody treatments (Panel A) and photographs of immunostained cryosections of excised matrigel plugs (Panel B).

Murine angiogenesis was induced by subcutaneous injection 400 μl of growth factor depleted matrigel containing 400 ng/ml bFGF or VEGF into the rear dorsal flanks of inbred mice of the strain FVB/N. Animals were treated on day 0 and day 3 by intravenous injection of 200 μg in 100 μg of endotoxin-free rat anti-murine α4β1 antibody (PS-2) or control isotype matched rat anti-murine integrin b2 antibody on days 1 and 4 (n=10). After 5 days, matrigel plugs were excised, embedded in OCT, frozen and sectioned. Thin sections (5 μm) were immunostained with rat anti-murine CD31 followed by Alexa 565-conjugated goat anti-rat immunoglobulin and then counterstained with DAPI. CD31 positive vessel density per 200×microscopic field was determined in 5 fields per matrigel plug. Mean vessel density per field+/−SEM was determined in five randomly selected microscopic fields for each plug in each treatment group and graphed versus treatment condition (n=8) (FIG. 18A). Photographs were taken of representative fields, with red indicating CD31 positive blood vessels and blue representing nuclei of all cells (FIG. 18B).

Antibody antagonists of integrin α4β1 (anti-α4β1) inhibited the ability of either bFGF or VEGF, two pro-angiogenic factors, to induce the growth of new blood vessels. Numerous new blood vessels stimulated by VEGF or bFGF were identified in tissue sections by their reactivity with anti-CD31, a specific marker of endothelial cells that line blood vessels. Few CD31 positive vessels could be identified in tissue sections from anti-α4β1 treated mice, while many blood vessels were observed in tissue sections from control antibody treated mice (cIgG). Quantification of the number of vessels induced in the presence of anti-α4β1 or control antibodies indicated that anti-α4β1 inhibited angiogenesis.

Example 16

Antagonists of α4β1 Block Murine Corneal Angiogenesis

Polymerized pellets containing 400 ng/ml VEGF were implanted into the corneas of inbred mice of the strain FVB/N. Animals were treated by intravenous injection of 200 μg in 100 μl of endotoxin free rat anti-murine α4β1 antibody (PS-2) or control isotype matched antibody (n=3) on days 1 and 4. Mice were perfused on day 5 with FITC-Bandeira simplicifolia, a lectin that selectively binds to all endothelium. Mice were sacrificed, corneas excised and cryopreseved. Thin cryosections sections were the photographed and mean area of fluorescence in the cornea was determined.

Figure 19:
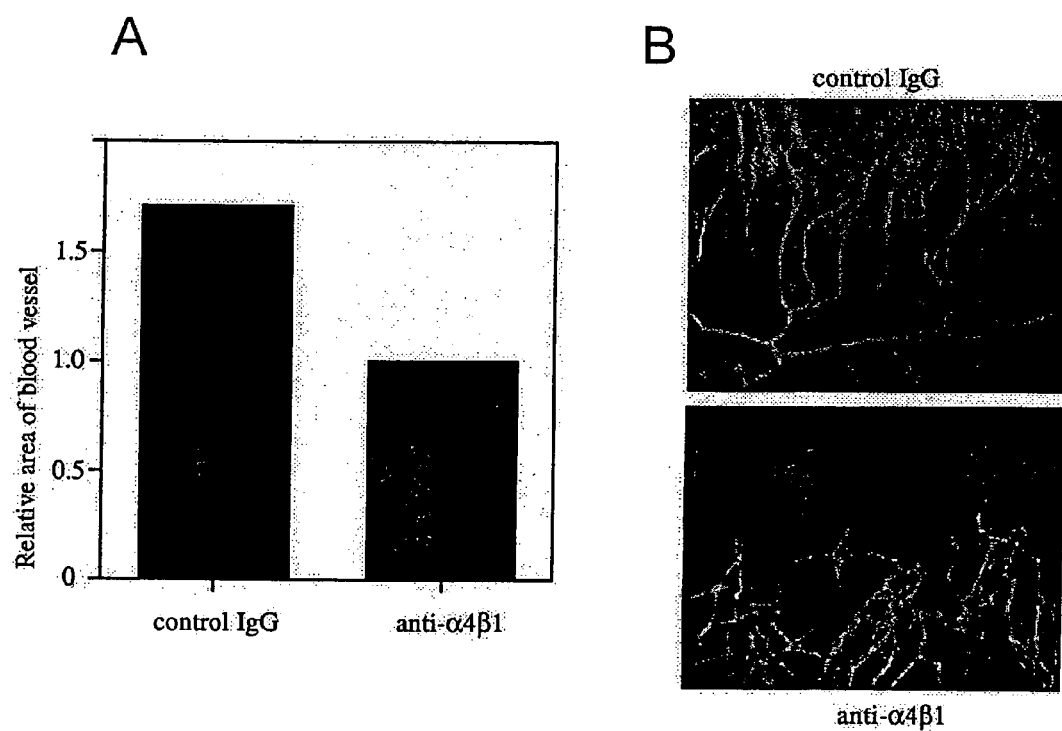
FIG. 19 shows a graph of relative area of blood vessel versus antibody treatment (Panel A) and photographs of FITC labeled blood vessels in cryosections of cornea (Panel B).

Antibody antagonists of integrin α4β1 (anti-α4β1) inhibited the ability of VEGF to induce the growth of new blood vessels in the cornea. Microvessel density was determined as a function of involved area for each treatment group (FIG. 19A). Numerous FITC-labeled new blood vessels stimulated by VEGF could be seen in tissue sections in control treated animals (FIG. 19B). Fewer fluorescent vessels were observed in anti-α4β1 treated mice (FIG. 19B). Quantification of the area invaded by blood vessels (green fluorescent area) indicated that anti-α4β1 inhibited corneal angiogenesis.

Example 17

Endothelial Progenitor Cells (EPC) Express Integrin α4β1

Figure 20:
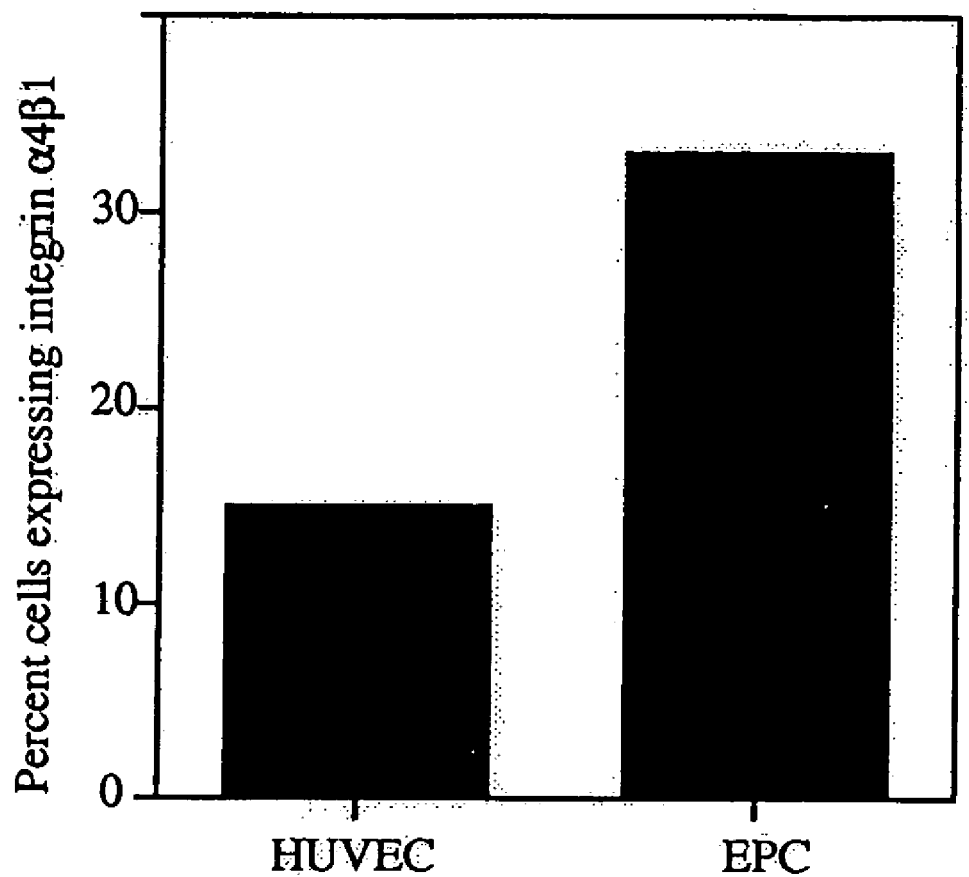
FIG. 20 shows a graph of percent cells expressing integrin α4β1 versus HUVEC and EPC.

Purified human umbilical vein endothelial cells ("HUVECS") (Clonetics, San Diego, Calif.) and endothelial progenitor cells ("EPCs") cultured on fibronectin from circulating CD34+ stem cells [see Asahara et al., Science, 275:964-967, (1997)], were incubated with mouse anti-human integrin α4β1 antibodies for 60 minutes on ice, washed twice with PBS and then incubated for 30 minutes on ice in rhodamine-labeled goat anti-mouse IgG. Cells were washed twice with cold PBS then analyzed on a FACSCAN analyzer for expression of integrin α4β1. The percent cells expressing this integrin was determined and plotted according to cell type (FIG. 20).

Thirty-three percent of endothelial progenitor cells were positive for integrin α4β1 expression while only 12% of HUVECS were positive. These results showed that the inhibitory effect of α4β1 antagonists in angiogenesis result from an inhibition of the participation of endothelial progenitor cells in angiogenesis.

Figure 21:
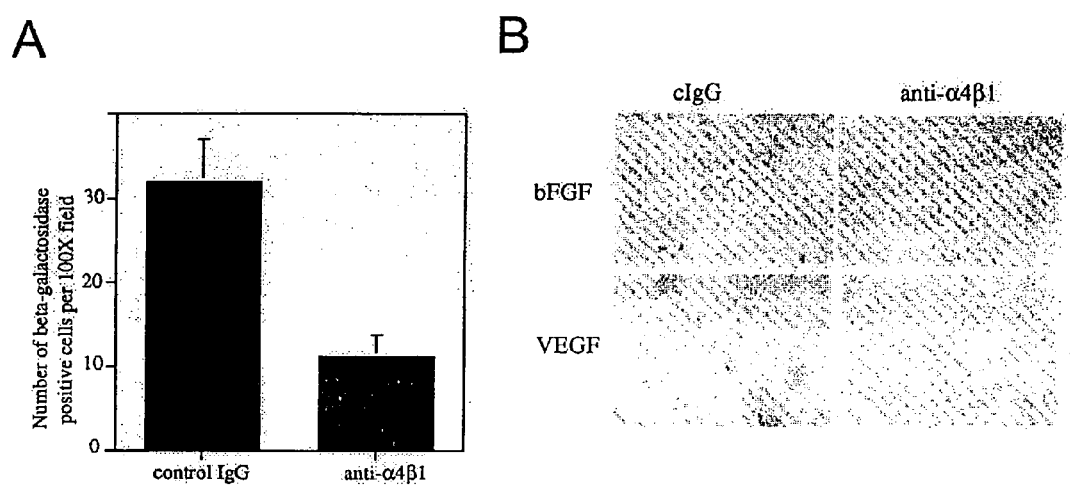
FIG. 21 shows a graph of number of beta-galactosidase positive cells per 100×field versus antibody treatments (Panel A) and photographs of immunostained cryosections of excised matrigel plugs (Panel B).

Example 18

α4β1 Antagonists Block Endothelial Stem Cell Contribution to Angiogenesis Murine angiogenesis was induced by subcutaneous injection 400 µl of growth factor depleted matrigel containing 400 ng/ml bFGF or VEGF into the rear dorsal flanks of inbred mice of the strain FVB/N or into FVB/N mice that had been irradiated and transplanted with bone marrow from Tie2LacZ mice. Animals were treated by intravenous injection on day 0 and day 3 with 200 µg of endotoxin free rat anti-murine α4β1 antibody (PS-2) in 100 µl or control isotype matched rat anti-murine integrin beta 2 antibody on days 1 and 4 (n=10). After 5 days, matrigel plugs were excised, embedded in OCT, frozen and sectioned. Thin sections (5 µm) were immunostained with rat anti-murine CD31 followed by Alexa 565-conjugated goat anti-rat immunoglobulin. CD31 positive vessel density per 200×microscopic field was determined in 5 fields per matrigel plug. Mean vessel density per field+/−SEM was graphed versus treatment condition. Photographs were taken of representative fields of control IgG and anti-α4β1 treated bFGF or VEGF containing plugs stained for beta galactosidase expression, with red indicating CD31 positive blood vessels and blue representing nuclei of all cells (FIG. 21B). Sections from Tie2/LacZ transplanted mice were analyzed for presence of bone marrow derived endothelial cells by staining sections for expression of beta galactosidase using a kit from Life Technologies. Blue cells in the plugs that arose from the transplanted bone marrow were counted (FIG. 21A) with bFGF stimulating angiogenesis.

Antagonists of integrin α4β1 prevent the participation of endothelial progenitor cells in angiogenesis. Beta galactosidase expressing endothelial cells derive from bone marrow because these mice were irradiated to kill their own bone marrow prior to transplantation with bone marrow from mice that express LacZ under an endothelial specific promoter, the Tie2 promoter. Thus, endothelial cells that arise from bone marrow will turn blue in tissues incubated in a substrate for beta galactosidase. These data showed that fewer blue endothelial cells were induced by growth factors in mice treated with anti-α4β1 than in mice treated with control antibodies. Therefore, anti-α4β1 inhibited the participation in angiogenesis of endothelial progenitors derived from bone marrow.

Example 19

Antagonists of α4β1 Inhibit Tumor Growth

Seven-week-old Balb/c nu/nu mice were inoculated subcutaneously with 2 million integrin-a4β1 negative HT29 colon carcinoma cells in DMEM culture medium. When tumors were approximately 50 cubic mm in size (2 weeks later), treatment began with intravenous injection twice weekly with saline or three concentrations of rat anti-mouse α4β1 antibody (PS-2). The doses were 200, 400 or 600 µg of antibody per injection. Ten mice were included in each treatment group. Tumor dimensions were measured every other day and tumor volumes were calculated. See FIG. 22A. After four weeks of treatment, tumors were excised and mass were determined. Mean tumor volumes per group were plotted versus time for the entire growth period. Mean tumor mass was plotted per group. See FIG. 22B.

Integrin α4β1 antagonists inhibited growth of integrin α4β1 negative tumors. As these antagonists inhibit angiogenesis, these studies showed that integrin α4β1 antagonists block tumor angiogenesis.

From the above, it is clear that the invention provides methods and compositions for detecting and inhibiting angiogenesis, endothelial cell adhesion, and endothelial cell migration. In some preferred embodiments, the present invention utilizes agents that inhibit the specific binding of integrin α4β1 to one or more of its ligands. The invention further provides methods and compositions for screening test compounds for their ability to inhibit angiogenesis, endothelial cell adhesion, and/or endothelial cell migration, by employing agents which inhibit the specific binding of integrin α4β1 to one or more of its ligands. The invention additionally provides methods and compositions for isolating endothelial cells which express integrin α4β1. The methods of the invention are useful in, for example, diagnosing and inhibiting pathological conditions that are associated with angiogenesis, endothelial cell adhesion, and/or endothelial cell migration. The methods and compositions of the present invention are also useful in isolating endothelial progenitor cells, and in determining the mechanisms that underlie angiogenesis, development, wound healing, and the function of the female reproductive system.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiment, it should be understood that the invention as claimed should not be unduly limited to such specific embodiment. Indeed, various modifications of the described modes for carrying out the invention which are obvious to those skilled in the art and in fields related thereto are intended to be within the scope of the following claims.

I claim:

1. A method for inhibiting angiogenesis in colon tissue, comprising:
   a) providing: i) angiogenic colon tissue comprising endothelial cells that express integrin α4β1; and ii) an agent which inhibits specific binding of integrin α4β1 to an integrin α4β1 ligand; and
   b) inhibiting angiogenesis in said colon tissue by treating said tissue with said agent under conditions that inhibit specific binding of said integrin α4β1 that is expressed by said endothelial cells to said integrin α4β1 ligand.

2. The method of claim 1, wherein said colon tissue is in a subject.

3. The method of claim 2, wherein said colon tissue comprises a tumor.

4. The method of claim 3, wherein said tumor is malignant.

5. The method of claim 4, wherein said malignant tumor is metastatic.

6. The method of claim 1, wherein said agent comprises a peptide.

7. The method of claim 1, wherein said agent comprises an antibody.

8. The method of claim 7, wherein said antibody is an anti-integrin α4β1 antibody.

9. The method of claim 7, wherein said antibody is an anti-vascular cell adhesion molecule antibody.

10. The method of claim 7, wherein said antibody is an anti-fibronectin antibody.

11. The method of claim 1, wherein said ligand is vascular cell adhesion molecule.

12. The method of claim 1, wherein said ligand is fibronectin.

* * * * *